US012731679B2

(12) United States Patent
Gray et al.

(10) Patent No.: US 12,731,679 B2
(45) Date of Patent: Sep. 8, 2026

(54) PRIVACY ENABLED SYSTEM AND METHOD FOR MANAGING LOGISTICS FOR CLINICAL STUDY PARTICIPANTS

(71) Applicant: Gray Consulting, Inc., Philadelphia, PA (US)

(72) Inventors: Scott Gray, Fort Lauderdale, FL (US); William Wing, San Francisco, CA (US); Trevor Smith, Salt Lake City, UT (US); Brent Snyder, Souderton, PA (US); Donna Brumback, Raleigh, NC (US)

( * ) Notice: Subject to any disclaimer, the term of this patent is extended or adjusted under 35 U.S.C. 154(b) by 0 days.

(21) Appl. No.: 18/278,198

(22) PCT Filed: Mar. 22, 2022

(86) PCT No.: PCT/US2022/021443
§ 371 (c)(1),
(2) Date: Aug. 22, 2023

(87) PCT Pub. No.: WO2023/091176
PCT Pub. Date: May 25, 2023

(65) Prior Publication Data

US 2024/0135267 A1 Apr. 25, 2024
US 2024/0233925 A9 Jul. 11, 2024

Related U.S. Application Data

(60) Provisional application No. 63/281,046, filed on Nov. 18, 2021.

(51) Int. Cl.
*G16H 40/20* (2018.01)
*G06F 21/62* (2013.01)
(Continued)

(52) U.S. Cl.
CPC ......... *G16H 40/20* (2018.01); *G06F 21/6245* (2013.01); *G06Q 10/02* (2013.01); *G06Q 10/1093* (2013.01); *G16H 10/20* (2018.01)

(58) Field of Classification Search
CPC ............... G06Q 10/02; G06Q 10/1095; G06Q 10/1093; G06Q 10/10; G06Q 50/14; G06F 21/6245; G16H 10/20; G16H 40/20
See application file for complete search history.

(56) References Cited

U.S. PATENT DOCUMENTS 8,160,614 B2 4/2012 Shaffer et al.
8,719,049 B2 5/2014 Samar et al.
(Continued)

FOREIGN PATENT DOCUMENTS

WO WO199835311 A1 8/1998
WO WO2021222431 A1 11/2021
WO WO2022011380 A1 1/2022

OTHER PUBLICATIONS

Krishnankutty B, Bellary S, Kumar NB, Moodahadu LS. Data management in clinical research: An overview. Indian J Pharmacol. Mar. 2012;44(2):168-72. doi: 10.4103/0253-7613.93842. PMID: 22529469; PMCID: PMC3326906 (available at: https://www.ncbi.nlm.nih.gov/pmc/articles/PMC3326906/) (Year: 2012).*
(Continued)

*Primary Examiner* — Rupangini Singh
*Assistant Examiner* — Stephanie S. Wallick
(74) *Attorney, Agent, or Firm* — Stoyanov Law PLLC; Roy L. Chan

(57) ABSTRACT

A privacy enabled system for managing clinical study participant travel has a database (stores data: clinical study, participant, clinical site and trip data sets) and a graphical user interface that has a Travel Planning Interface and is in data communication with an input device and the database. The data sets include a Study Travel Policy, a Study Visit
(Continued)

11

Schedule (appointment procedure, appointment schedule), a traveler profile, traveler personal data (traveler contact information), a site appointment location associated with the appointment procedure, and site contact information. The travel planning interface receives the trip data set (trip segment data) from the database and the input device. The travel planning interface transmits the trip segment data to and receives booked travel data from a travel booking module, generates an itinerary that has booked travel and trip segment data, and transmits the itinerary according to the traveler contact information and the site contact information.

6 Claims, 41 Drawing Sheets

(51) Int. Cl.

| | |
|---|---|
| ***G06Q 10/02*** | (2012.01) |
| ***G06Q 10/1093*** | (2023.01) |
| ***G16H 10/20*** | (2018.01) |

(56) References Cited

U.S. PATENT DOCUMENTS

| | | | | |
|---|---|---|---|---|
| 8,793,145 | B2 | 7/2014 | Kahn et al. | |
| 10,417,584 | B2 | 9/2019 | Jaffe et al. | |
| 10,460,350 | B2 | 10/2019 | Polo et al. | |
| 10,957,452 | B2 | 3/2021 | Stevens et al. | |
| 11,107,559 | B1 * | 8/2021 | Wynden | G16H 10/40 |
| 2004/0006553 | A1 * | 1/2004 | de Vries | G16H 80/00 |
| 2006/0047539 | A1 | 3/2006 | Huang | |
| 2006/0122872 | A1 | 6/2006 | Stevens et al. | |
| 2008/0046298 | A1 * | 2/2008 | Ben-Yehuda | G06Q 10/109 705/6 |
| 2008/0288275 | A1 | 11/2008 | Houriet, Jr. et al. | |
| 2009/0210262 | A1 * | 8/2009 | Rines | G06Q 10/06 705/5 |
| 2011/0046985 | A1 * | 2/2011 | Raheman | G06Q 40/08 705/4 |
| 2011/0110568 | A1 | 5/2011 | Vesper et al. | |
| 2011/0213787 | A1 * | 9/2011 | Cerny | G06Q 10/02 707/E17.014 |
| 2012/0004926 | A1 * | 1/2012 | Samar | G06Q 10/10 705/2 |
| 2012/0101837 | A1 | 4/2012 | McCorkle et al. | |
| 2012/0185793 | A1 | 7/2012 | Binsztok | |
| 2013/0290009 | A1 * | 10/2013 | Rosenblum | G16H 10/20 705/2 |
| 2014/0019176 | A1 * | 1/2014 | Mandelbaum | G06Q 10/025 705/6 |
| 2014/0039921 | A1 | 2/2014 | Broverman et al. | |
| 2014/0316793 | A1 | 10/2014 | Pruit et al. | |
| 2014/0379362 | A1 | 12/2014 | Bachenheimer et al. | |
| 2015/0046187 | A1 * | 2/2015 | Johnson | G06Q 50/40 705/3 |
| 2015/0154361 | A1 | 6/2015 | Barsoum et al. | |
| 2015/0254432 | A1 | 9/2015 | Stumm et al. | |
| 2016/0147963 | A1 * | 5/2016 | Bouhnik | G16H 40/63 705/2 |
| 2016/0317077 | A1 | 11/2016 | Sillay | |
| 2017/0154389 | A1 | 6/2017 | Bashvitz et al. | |
| 2017/0213015 | A1 | 7/2017 | Jodi | |
| 2018/0182055 | A1 * | 6/2018 | Jepson | G06Q 20/102 |
| 2019/0066240 | A1 * | 2/2019 | Goldstein | G06Q 50/14 |
| 2019/0206521 | A1 | 7/2019 | Walpole et al. | |
| 2019/0311787 | A1 | 10/2019 | Graiver et al. | |
| 2019/0370907 | A1 | 12/2019 | Cunningham et al. | |
| 2019/0371475 | A1 | 12/2019 | Oliveira et al. | |
| 2020/0020422 | A1 | 1/2020 | Cox et al. | |
| 2020/0193055 | A1 | 6/2020 | Naveed | |
| 2020/0381086 | A1 | 12/2020 | Atreja et al. | |
| 2021/0390209 | A1 * | 12/2021 | Lee | G06F 21/64 |
| 2022/0005554 | A1 | 1/2022 | Malfait et al. | |
| 2022/0237526 | A1 * | 7/2022 | Carpanzano | G06Q 40/12 |
| 2023/0315875 | A1 * | 10/2023 | Hansen | G06F 21/6218 726/26 |
| 2023/0385450 | A1 * | 11/2023 | Bessette | G16H 10/20 |

OTHER PUBLICATIONS

Dunstall et al., An Automated Itinerary Planning System for Holiday Travel, CSIRO Mathematical and Information Sciences, Information Technology & Tourism, V6 pp. 195-210 (2004).

* cited by examiner

Figure 26:
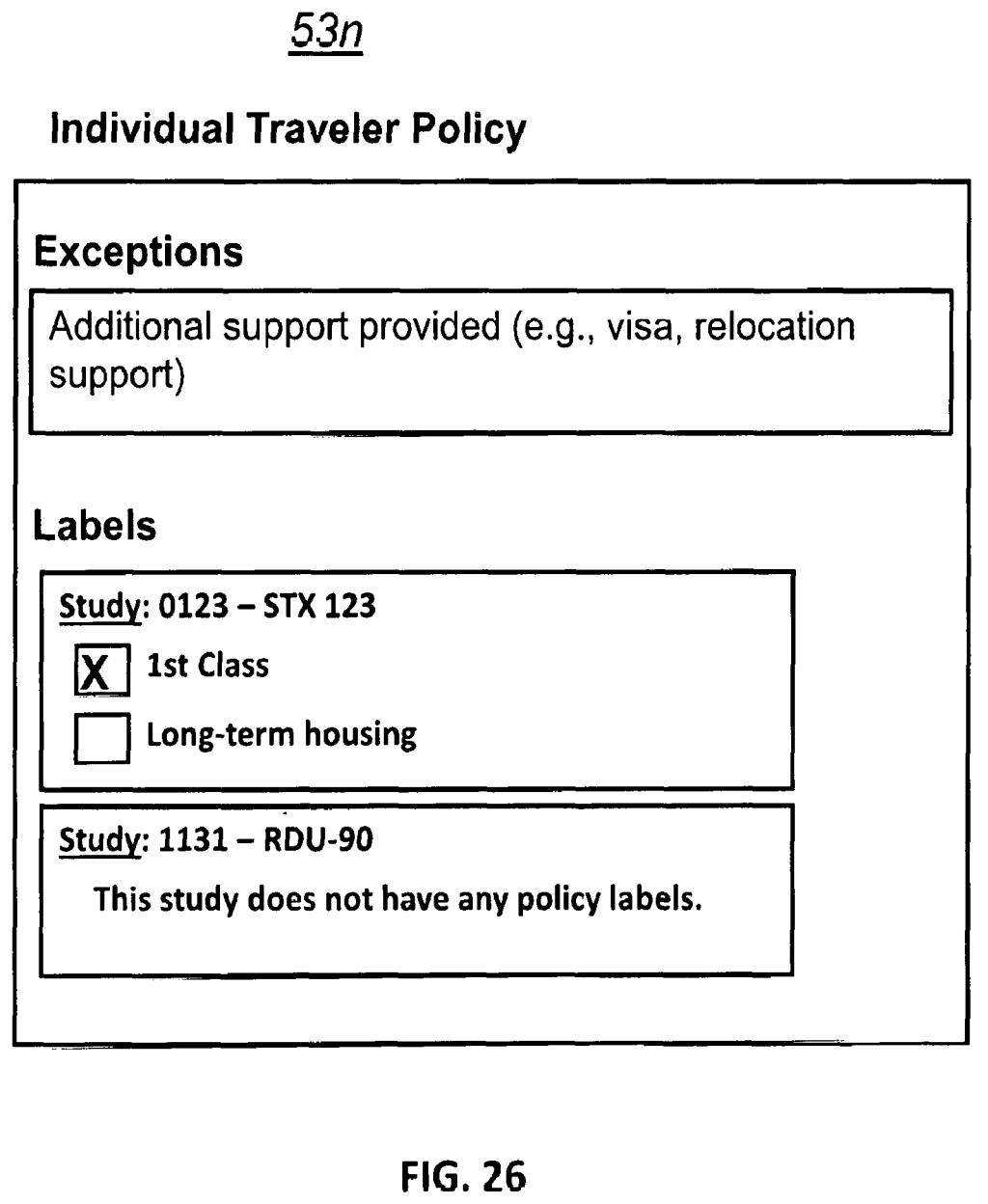

53n

Individual Traveler Policy

Exceptions

Additional support provided (e.g., visa, relocation support)

Labels

Study: 0123 – STX 123

[X] 1st Class

[ ] Long-term housing

Study: 1131 – RDU-90

This study does not have any policy labels.

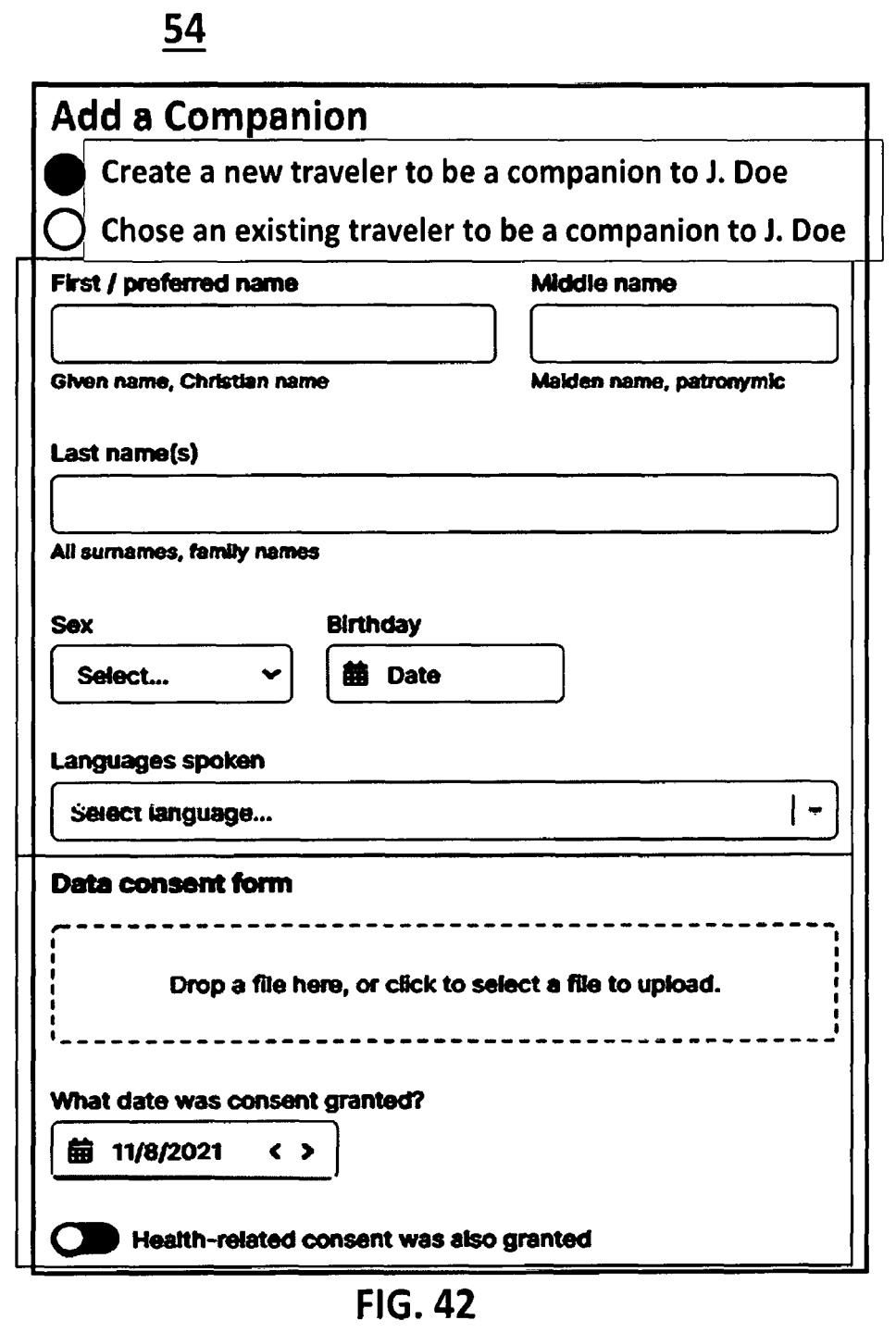

Add a Companion

Create a new traveler to be a companion to J. Doe

Chose an existing traveler to be a companion to J. Doe

First / preferred name

Given name, Christian name

Middle name

Maiden name, patronymic

Last name(s)

All surnames, family names

Sex

Select...

Birthday

Date

Languages spoken

Select language...

Data consent form

Drop a file here, or click to select a file to upload.

What date was consent granted?

11/8/2021

Health-related consent was also granted

FIG. 42

PRIVACY ENABLED SYSTEM AND METHOD FOR MANAGING LOGISTICS FOR CLINICAL STUDY PARTICIPANTS

CROSS-REFERENCE TO RELATED APPLICATIONS

This application claims the benefit of U.S. Provisional Patent Application 63/281,046, filed Nov. 18, 2021, which is hereby incorporated by reference in its entirety.
Not Applicable

STATEMENT REGARDING FEDERALLY SPONSORED RESEARCH OR DEVELOPMENT

Not Applicable

REFERENCE TO SEQUENCE LISTING, A TABLE, OR A COMPUTER PROGRAM LISTING COMPACT DISC APPENDIX

Not Applicable

BACKGROUND OF THE INVENTION

The present invention relates to a system for managing participants in a clinical study. Clinical studies may be organized, funded, or sponsored by various entities (e.g., medical or pharmaceutical companies, government agencies, hospitals, doctors, health care providers, and others), usually referred to as sponsors. Sponsors may set various requirements for the study, including for example, the time, length, schedules, and goals of the study; the drugs or medications to be studied and their dosages; the treatments or procedures to be studied and their duration; the locations where to perform procedures and tests; the types and numbers of study participants, rules and policies for the management and recruitment of study participant, and various other rules and requirements. Sponsors may also establish the study budgets and financial rules.

Clinical studies can be expensive, with substantial budgets for identification, recruitment, and management of volunteer study participants. When participants drop out of a study, it may lead to substantial additional costs, for example, to replace participants and perform the study procedures on the replacements to generate study data, to accommodate delays associated with high participant drop-out rate, and various other costs. Therefore, reducing the number of participants who drop out of a clinical study may lead to a reduction, or more efficient use, of study budgets.

Participants may drop out of studies for various reasons, including difficulties traveling to study locations, financial challenges, scheduling interference with work or family commitments, and others. Often the participants are patients (participant and patient are used interchangeably below) who enroll in a clinical study due to health conditions that may constrain the patient's abilities and availability. It is therefore desirable to provide a way of assisting study participants to unburden them and alleviate their participation challenges. One such way may be by providing participants with streamlined means (e.g., app, software, website, call center, etc.) that participants can use at their convenience to perform various participation related tasks, such as booking travel, expenses reimbursement, and others. Such solutions that may allow participants to, for example, arrange their own travel, still demand time and effort from participants. Also, for privacy, security, consistency, simplicity, and various other reasons, participant-facing systems usually would need to enforce the same study-wide travel and financial policies for all participants who book their own travel. Accordingly, it may be difficult or impossible for participants to reserve by themselves travel with individualized accommodations. Embodiments of the present invention enable an efficient and automated concierge type service for participants allowing individualized accommodations, as well as minimizing the time participants need to spend managing the logistics of their participation in the clinical study.

In addition, any system that collects, stores, processes, accesses, or displays, personal information or protected health information must implement strict privacy, data security, and auditing measures consistent with various privacy and data security laws and regulations. The issue becomes even more complex when participants are from multiple international jurisdictions. Implementing appropriate security measures while providing individualizing functionality in participant-facing systems could become complex, considering that such systems, e.g., a mobile app, may be accessed by thousands of individuals, in multiple international jurisdictions, over public networks, and in insecure locations, to name a few potential risks.

Various privacy and data security, national and international laws and regulations (e.g., HIPAA, HITECH, GDPR, UK, Russia, Turkey, Canada, Australia, and others) ("Privacy Laws") establish complex standards intended to protect the security and privacy of various information related to individuals, including Personal Information (PI), personally identifiable information (PII), personal data (PD), protected health information (PHI), and others. The GDPR also includes a category of "special" "Data concerning health" or "Health Records."

For consistency and ease of reference, below "Personal Information" or "PI" are used to refer to all types of sensitive personal information, including PII, PD, Health Records and PHI, that may be regulated by data privacy law or regulation in any jurisdiction. Privacy Laws impose requirements related to the use and disclosure of data containing Personal Information, appropriate safeguards to protect it, and establish individual rights, and administrative responsibilities with respect to Personal Information.

For example, the U.S. Department of Health and Human Services provides guidance for data encryption by "the use of an algorithmic process to transform data into a form in which there is a low probability of assigning meaning without use of a confidential process or key" (45 CFR 164.304 definition of encryption) and such confidential process or key that might enable decryption has not been breached. To avoid a breach of the confidential process or key, these decryption tools should be stored on a device or at a location separate from the data they are used to encrypt or decrypt. In another example, the General Data Protection Regulation (GDPR) in the European Union ("EU"), which became enforceable on May 25, 2018, applies to all processing of personal data either by organizations that have an establishment in the EU, or to organizations that process personal data of EU residents when offering goods or services to individuals in the EU or monitoring the behavior of EU residents in the EU. Personal data may be any information relating to an identified or identifiable natural person. Under the GDPR organizations must demonstrate the security of the data they are processing and their compliance with the GDPR on a continual basis, by implementing and regularly reviewing technical and organizational measures, as well as compliance policies applicable to the processing of personal data.

The various Privacy Laws provide recommendations, and/or requirements related to the types of security actions, including, by way of example i) employing pseudonymization and de-identification, ii) regularly testing, assessing, and evaluating the effectiveness of technical and organizational measures to ensure the security of data processing and the ability to send breach notifications in a timely manner; and iii) employing processes to ensure the ongoing confidentiality, integrity, availability and resilience of data processing systems and services. By pseudonymization and de-identification herein we refer to data management techniques and procedures that replace certain data, such as Personal Information data, with artificial identifiers, or pseudonyms thereby reducing privacy breach risks.

Various Privacy Laws also may require the implementation of auditing capabilities to allow examination of detailed activity logs or reports showing who had access to Personal Information data, from what IP addresses, what data were accessed, and other information Embodiments of the present invention are related to privacy enabled systems for facilitating the provision of concierge-like services for participants in clinical studies. In an embodiment of the present invention, a privacy enabled system for managing clinical study participant travel comprises a database storing data related to a clinical study and a Graphical User Interface in data communication with an input device and the database. The data are encrypted and comprise a clinical study data set, a participant data set, a clinical site data set, and a trip data set. The Graphical User Interface comprises a travel planning interface. The clinical study data set comprises a Study Travel Policy and a Study Visit Schedule. The Study Visit Schedule comprises an appointment procedure and an appointment schedule. The participant data set comprises a traveler profile and traveler personal data. The traveler personal data comprise traveler contact information. The clinical site data set comprises a site appointment location associated with the appointment procedure and a site contact. The travel planning interface is configured to receive the trip data set from the database and the input device. The trip data set comprises trip segment data that are based upon one or more of the appointment schedule, the site appointment location, the traveler profile, and the Study Travel Policy. The trip segment data are selected from the group consisting of appointment segment data, flight segment data, ambulance segment data, bus segment data, car rental segment data, car service segment data, train segment data, ferry segment data, lodging segment data, and combinations thereof. The travel planning interface is configured to transmit the trip segment data to a travel booking module. The travel planning interface is configured to receive booked travel data from the travel booking module. The travel planning interface is configured to generate an itinerary. The itinerary comprises the booked travel data and the trip segment data. The travel planning interface is configured to transmit the itinerary according to one or more of the traveler contact information and the site contact.

In another embodiment of the present invention, a privacy enabled system for managing clinical study participant travel comprises a database storing data related to a clinical study and a Graphical User Interface in data communication with an input device and the database. The data are encrypted and comprise a clinical study data set, a participant data set, a clinical site data set, and a trip data set. The Graphical User Interface comprises a travel planning interface. The clinical study data set comprises a Study Travel Policy and a Study Visit Schedule. The Study Visit Schedule comprises an appointment procedure and an appointment schedule. The participant data set comprises a traveler profile and traveler personal data. The traveler personal data comprise traveler contact information. The clinical site data set comprises a site appointment location associated with the appointment procedure and a site contact. The travel planning interface is configured to receive the trip data set from the database and the input device. The trip data set comprises first trip segment data and second trip segment data. The first trip segment data are based upon one or more of the appointment schedule, the site appointment location, the traveler profile, the Study Travel Policy, and the second trip segment data. The second trip segment data are based upon one or more of the appointment schedule, the site appointment location, the traveler profile, the Study Travel Policy, and the first trip segment data. The first trip segment data are selected from the group consisting of appointment segment data, flight segment data, ambulance segment data, bus segment data, car rental segment data, car service segment data, train segment data, ferry segment data, and lodging segment data. The second trip segment data are selected from the group consisting of appointment segment data, flight segment data, ambulance segment data, bus segment data, car rental segment data, car service segment data, train segment data, ferry segment data, and lodging segment data. The travel planning interface is configured to transmit one or more of the first trip segment data and the second trip segment data to a travel booking module. The travel planning interface is configured to receive booked travel data from the travel booking module. The travel planning interface is configured to generate an itinerary. The itinerary comprises the booked travel data. The itinerary comprises information from the first trip segment data and the second trip segment data. The travel planning interface is configured to transmit the itinerary according to one or more of the traveler contact information and the site contact.

In yet another embodiment of the present invention, a privacy enabled system for managing clinical study participant travel comprises a database storing data related to a clinical study and a Graphical User Interface in data communication with an input device and the database. The data are encrypted and comprise a clinical study data set, a participant data set, a clinical site data set, and a trip data set. The Graphical User Interface comprises a travel planning interface. The clinical study data set comprises a Study Travel Policy and a Study Visit Schedule. The Study Visit Schedule comprises an appointment procedure and an appointment schedule. The participant data set comprises a traveler profile and traveler personal data. The traveler personal data comprise traveler contact information. The clinical site data set comprises a site appointment location associated with the appointment procedure, and a site contact. The travel planning interface is configured to receive the trip data set from the database and the input device. The trip data set comprises first trip segment data, second trip segment data, and an appointment segment data. The first trip segment data are based upon one or more of the traveler profile, the Study Travel Policy, and the appointment segment data. The second trip segment data are based upon one or more of the appointment segment data, the traveler profile, the Study Travel Policy, and the first trip segment data. The first trip segment data are selected from the group consisting of flight segment data, ambulance segment data, bus segment data, car rental segment data, car service segment data, train segment data, ferry segment data, lodging segment data. The second trip segment data are selected from the group consisting of flight segment data, ambulance segment data, bus segment data, car rental segment data, car service segment data, train segment data, ferry segment data, lodging segment data. The appointment segment data comprise the appointment schedule and the site appointment location. The travel planning interface is configured to transmit booking request data to a travel booking module. The travel planning interface is configured to receive booked travel data from the travel booking module. The booking request data comprise information from one or more of the first trip segment data, the second trip segment data, and the appointment segment data. The travel planning interface is configured to generate an itinerary. The itinerary comprises the booked travel data. The itinerary comprises information from the first trip segment data, the second trip segment data, and the appointment segment data. The travel planning interface is configured to transmit the itinerary according to one or more of the traveler contact information and the site contact.

BRIEF DESCRIPTION OF THE SEVERAL VIEWS OF THE DRAWING

The advantages and features of the present invention will be better understood as the following description is read in conjunction with the accompanying drawings, wherein:

FIGS. 13-29 are diagrams illustrating embodiments of travel profiles of a clinical study participant in an embodiment of the present invention.

FIG. 42 is a diagram of an embodiment of a graphical user interface in an embodiment of the present invention.

Figure 1:
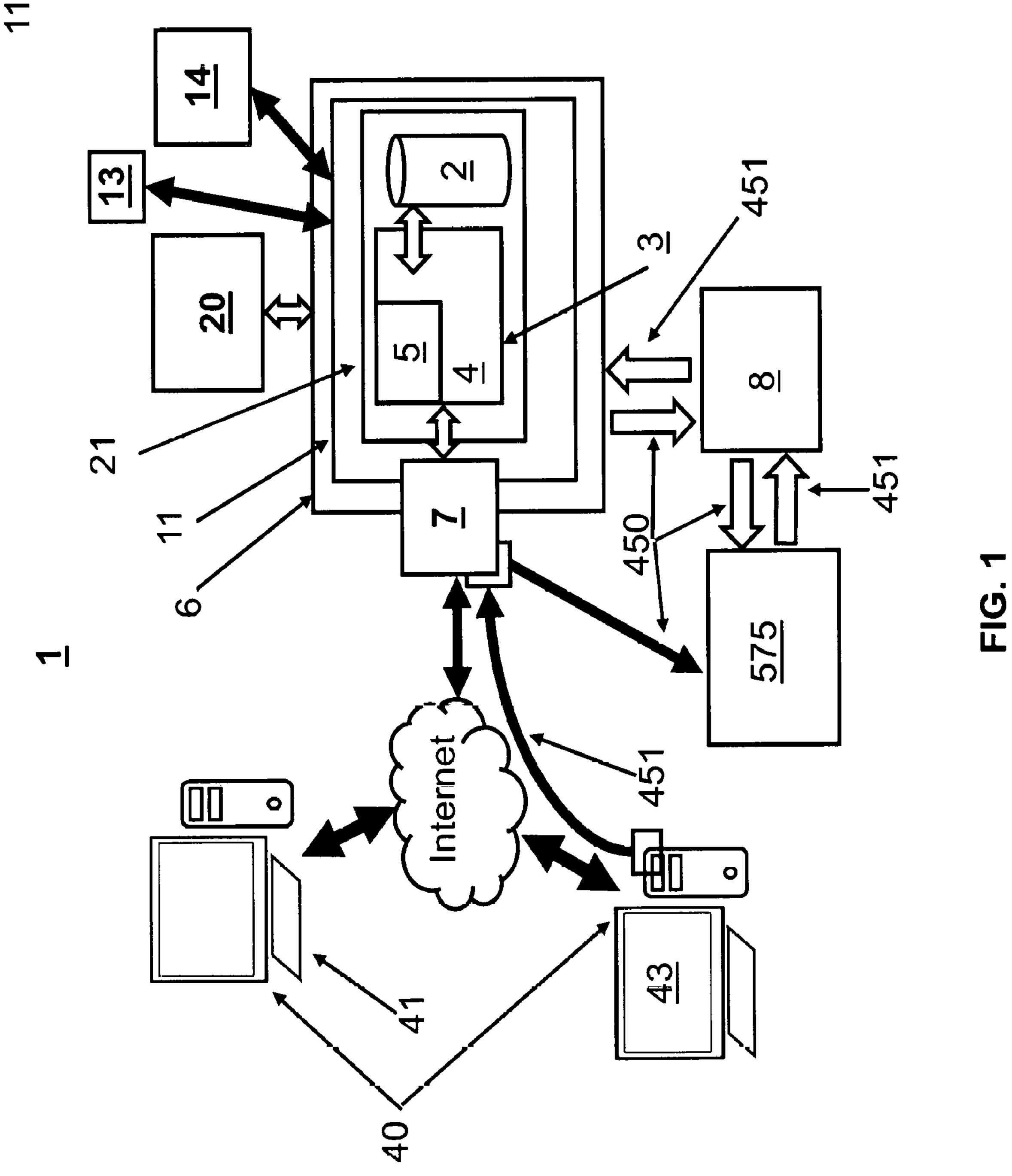
FIG. 1 is a diagram illustrating an embodiment of the present invention.

For clarity all reference numerals may not be included in every figure.

The present invention is related to the management of individuals participating in a broad range of experimental or observational medical, health, sociological, and other scientific research or studies, collectively referred below as Clinical Study 25, involving individual subjects who need to share Personal Information. While the present disclosure refers to clinical studies to illustrate embodiments of the invention, the invention should not be understood to be limited to only clinical studies.

FIG. 1 illustrates a system according to a preferred embodiment of the present invention, which may be implemented as a distributed, networked, system 1 utilizing a database 2, server 3, private cloud 6, and user workstations 40. System 1 may further utilize an internet gateway 7, monitoring tools 20, and data encryption tools 11.

Database 2 may be a SQL, Non-SQL, relational, or non-relational database (e.g., MySQL, Oracle, Mongo, Cassandra, ElasticSearch, Neo4J, and others) or any other datastore or repository for persistently storing and managing collections of data according to the invention. Preferably, Database 2 is secured within the Private Cloud 6, and may be further secured by isolating it in a private subnet within the private cloud 6, effectively preventing anyone outside the private cloud from gaining access to Database 2. All data stored in Database 2 preferably are encrypted while at rest (e.g., when stored in Database 2) using encryption tools 11.

Data 10 stored in Database 2 preferably are further protected, and/or obfuscated, for example by associating data records with unique randomly generated unique identifiers 12 (e.g., UUID, GUID, others) and using the unique identifiers 12 to query, access, and/or reference records or portions of Data 10. Unique identifiers 12 allow data 10 to be de-identified or pseudonymized. For example, in a SQL Database 2, unique identifier 12 may be used as a primary table key, or in a lookup (e.g., cross reference) table associating unique identifier 12 with a data record or even with an individual datum, or unique identifier 12 may be utilized in various other ways. For Non-SQL/non-relational database 2, the unique identifier may be used in an analogous manner to access records or values in, for example as a key or document identifier in key-value or document type Non-SQL Database (e.g., Mongo, key-value). In embodiments using Non-SQL Graph Databases, unique identifier 12 may be used within nodes/vertices, or for various key-value pairs for graph properties, thereby avoiding referencing the actual record values. Other methods of using unique identifier 12 and other methods of protecting data in relational and non-relational databases are well known.

Servers 3 may be web servers 4, application servers 5, or both, and may use dedicated or shared computing resources. Servers 3 preferably are secured within private cloud 6.

Workstation 40 may use display 42 to display data received from Database 2 or from input device 41. Workstation 40 may comprise a Graphical User Interface (GUI) 43 that visualizes and facilitates the input and manipulation of data by a user using workstation 40 and input device 41. User as used herein refers to any person associated with a study, such as staff affiliated with study sponsors, CROs, clinical sites, institutions, vendors, participants, and in general any person who is authorized to access a system according to the present invention using Workstation 40. Workstation 40 may be any computing device such as a personal computer, laptop, tablet, mobile device, thin client, or any other device capable of displaying the GUI and connecting to a network (e.g., the Internet, internal networks, other public or private networks). Input device 41 may be a mouse, keyboard, microphone, voice, optical input, camera, tape, and other known devices or methods for inputting data.

Display 42 may be any display or monitor comprising a display (e.g., monitor, screen, projector, e-ink, holographic, etc.) and a display controller (e.g., display hardware and software controlling the display), as well as any other hardware or software instrumentality, or interface used or known to properly operate Display 42. In a preferred embodiment, the display 42 may be part of workstation 40. Workstation 40 may display the GUI 43 using client (client here, as opposed to server, e.g., front end) software or program capable of visualizing information received over a network and/or input device 41, and of securely transmitting the information over a network. By way of example, the client software may be a browser capable of utilizing network protocols (e.g., HTTP, HTTPS, AS2, AS3, AS4, RTP, UDP, etc.) to send and receive data over networks and of displaying data using markup (e.g., HTML, XML, SGML, etc.) or other visualization techniques. In an embodiment with more than one workstation 40, each workstation/Display may display different data, and different aspects and/or views of GUI 43 permitting different users to simultaneously perform different actions.

Figure 5:
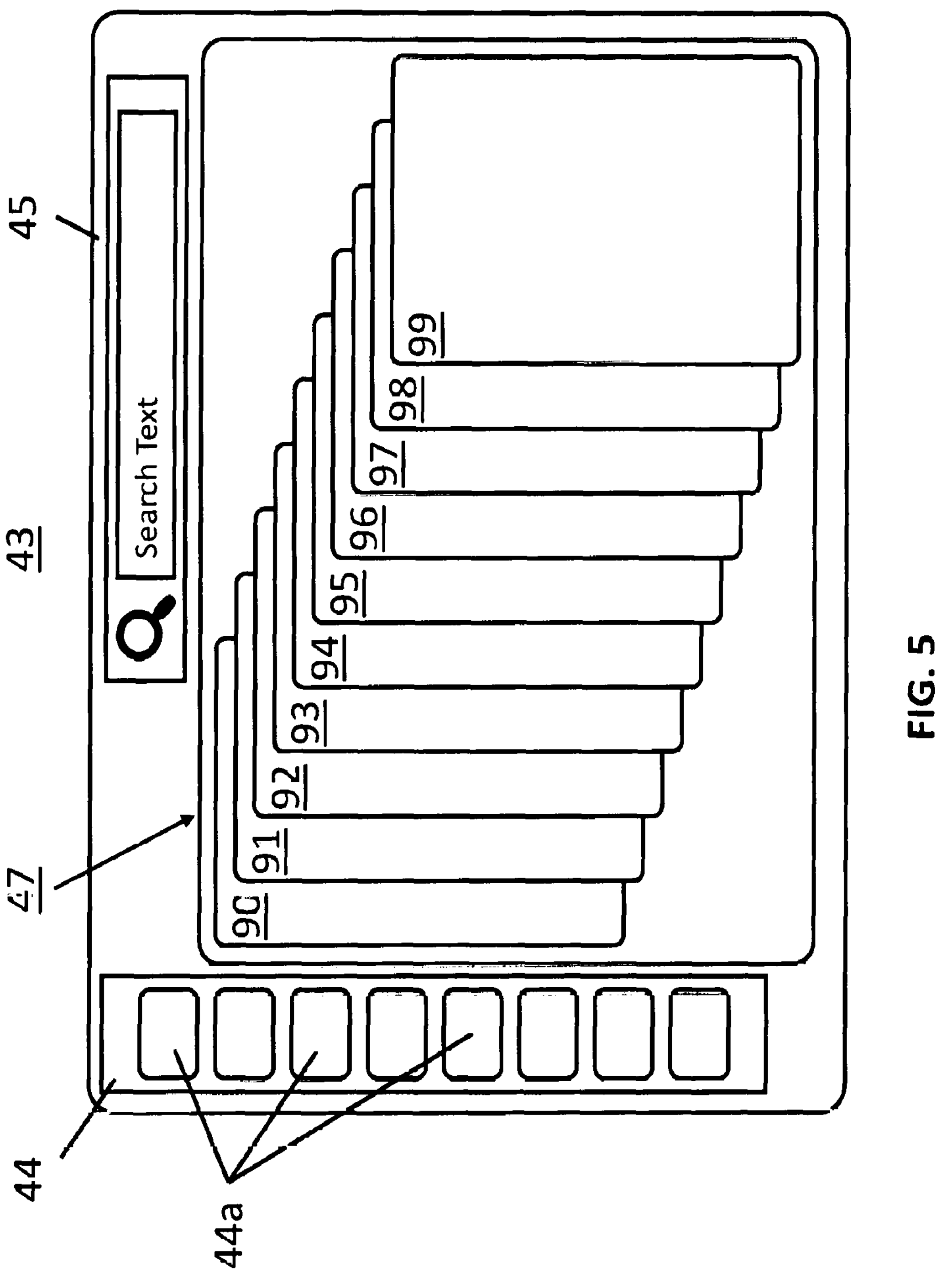
FIG. 5 is a diagram of an embodiment of a graphical user interface of an embodiment of the present invention.
Figure 6:
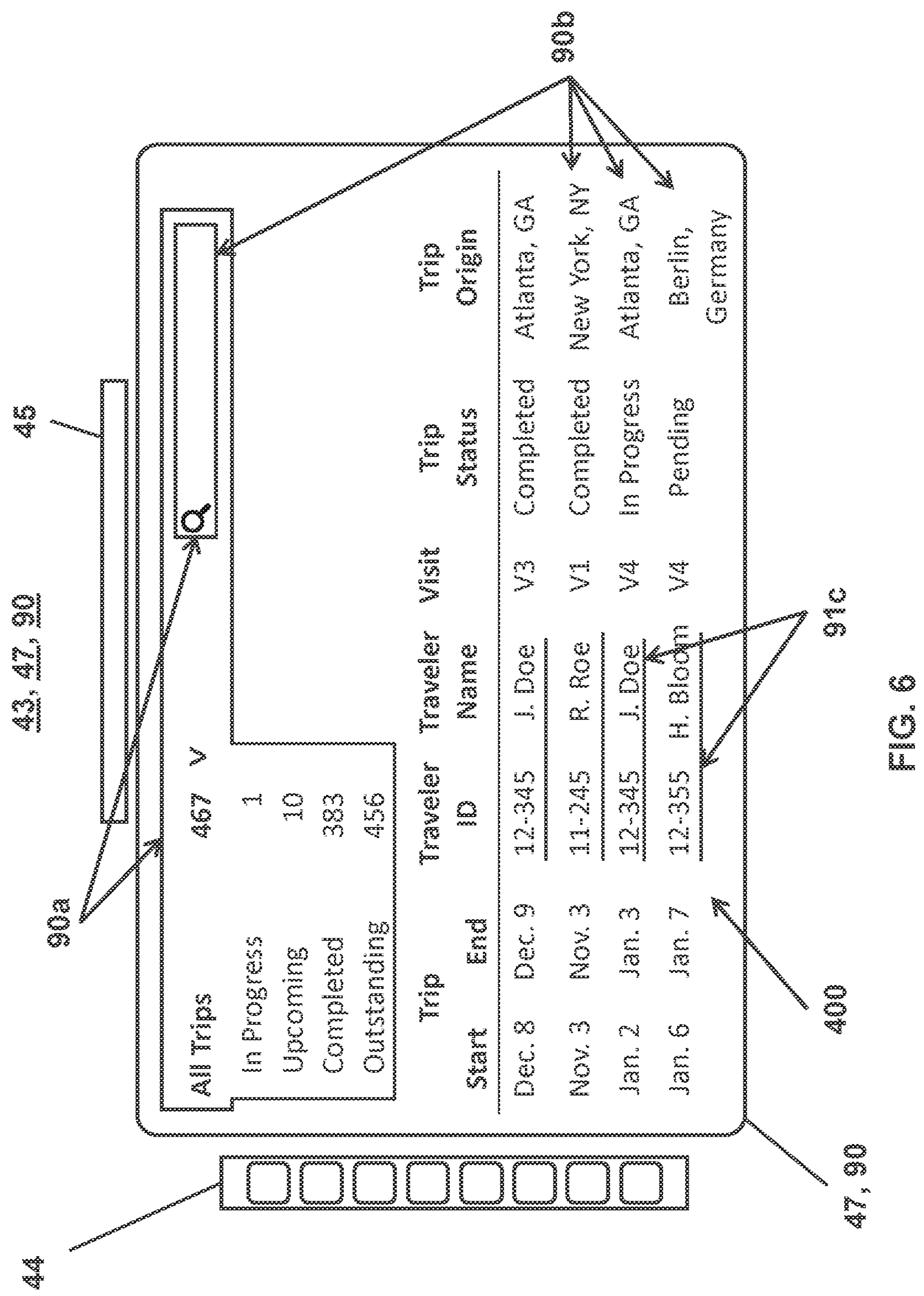
FIG. 6 is a diagram of an embodiment of a clinical study graphical user interface in an embodiment of the present invention.
Figure 7:
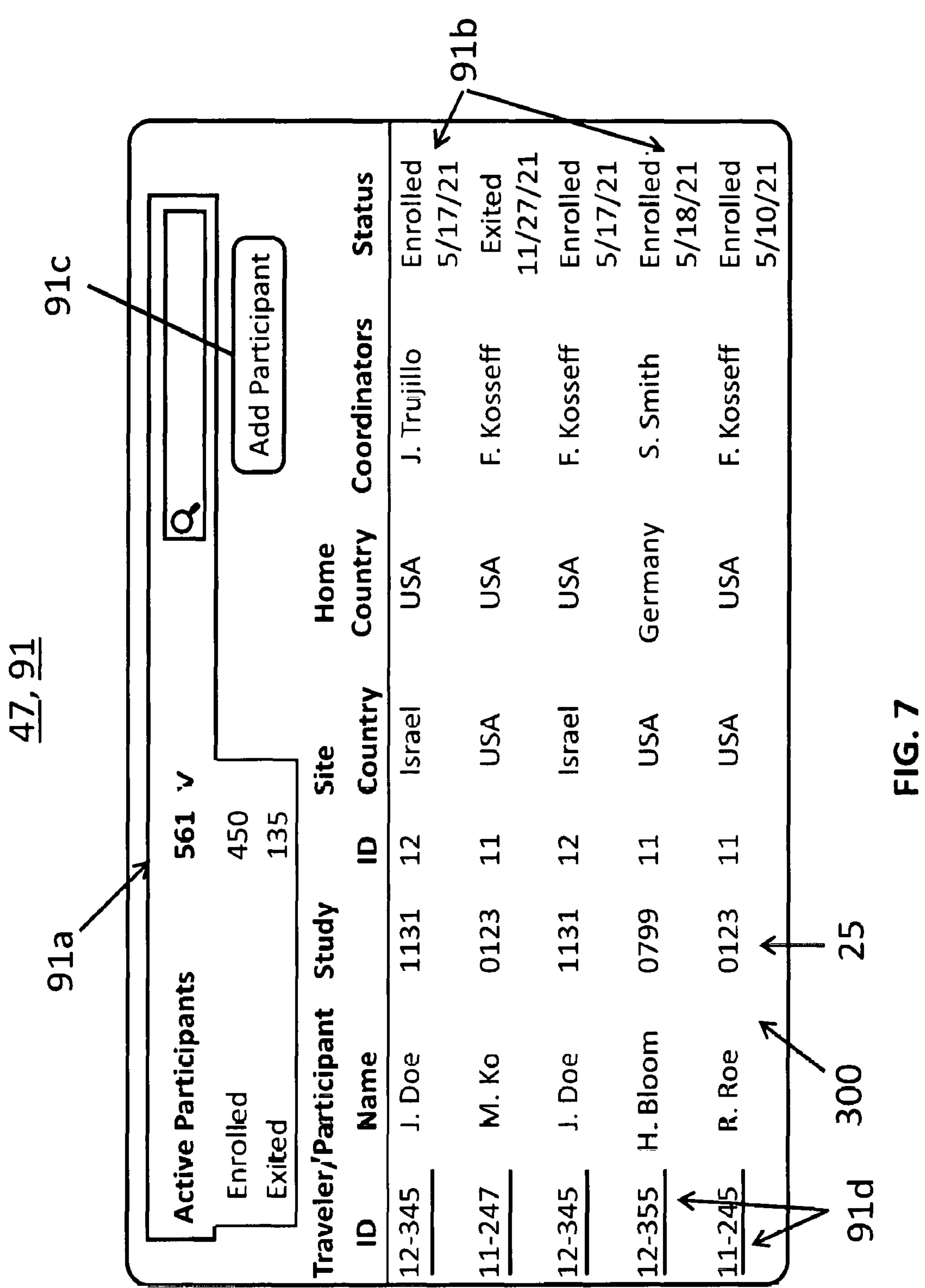
FIG. 7 is a diagram of an embodiment of a clinical study graphical user interface in an embodiment of the present invention.
Figure 8:
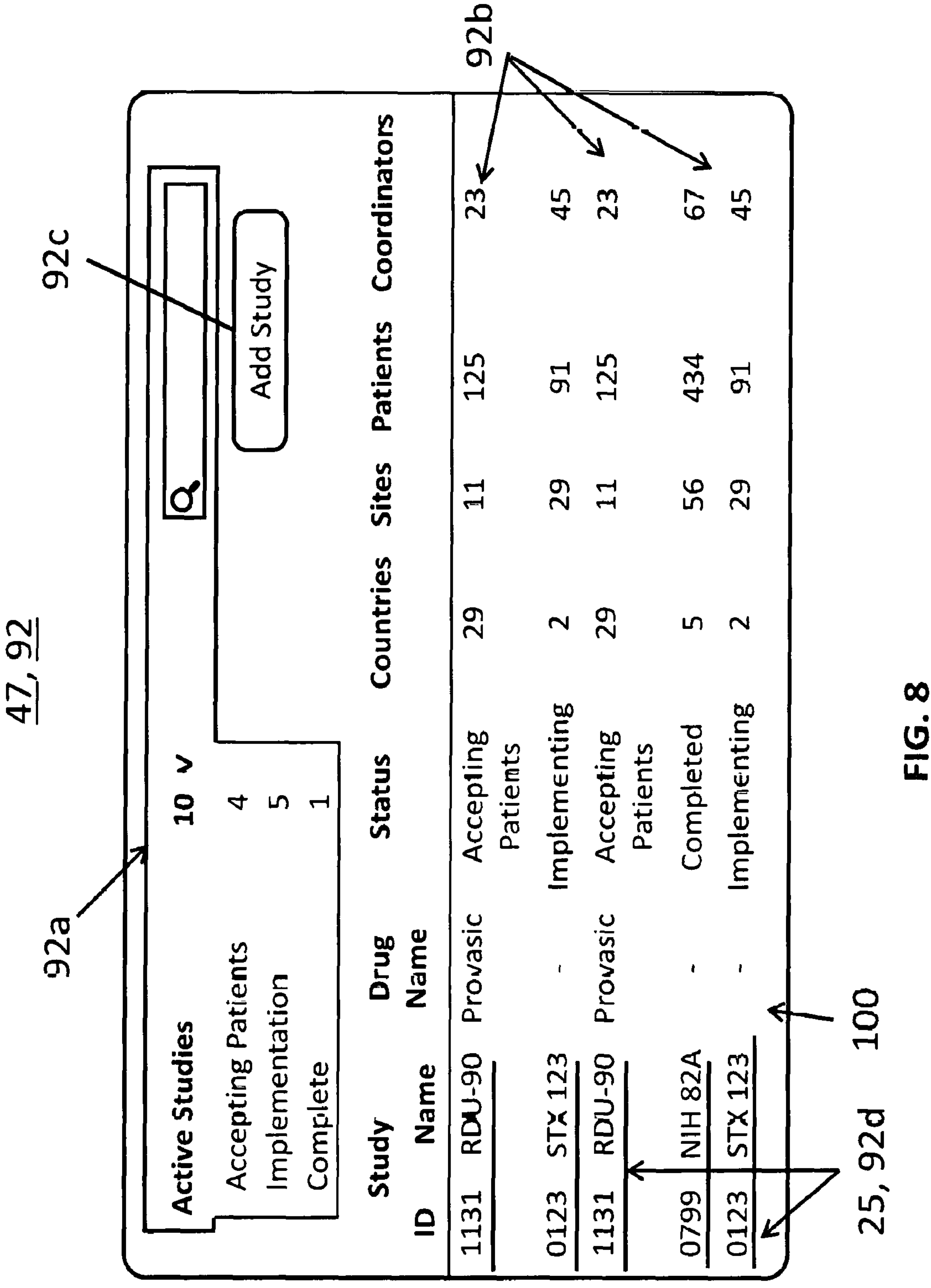
FIG. 8 is a diagram of an embodiment of a clinical study graphical user interface in an embodiment of the present invention.
Figure 9:
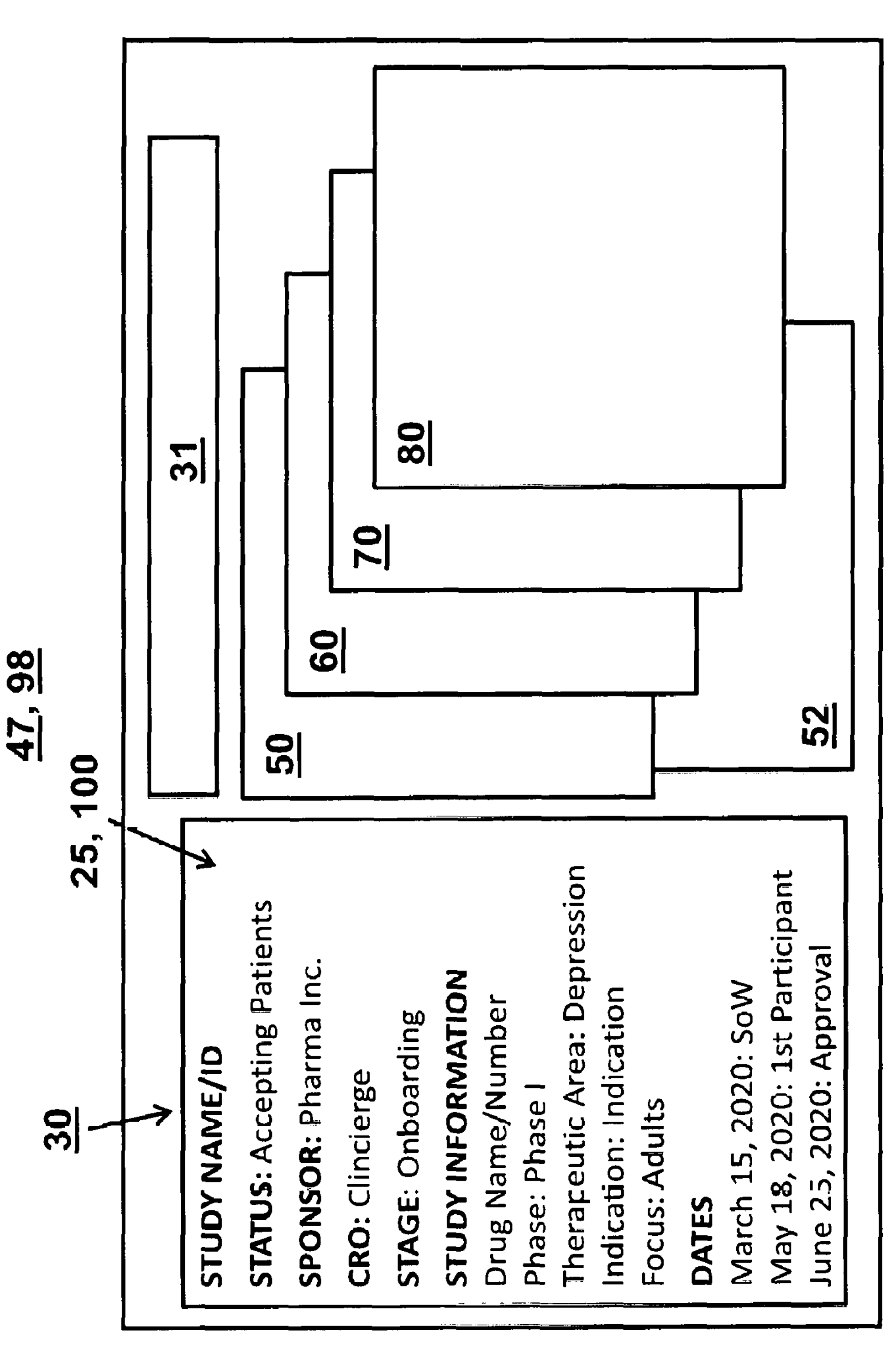
FIG. 9 is a diagram of an embodiment of a clinical study graphical user interface in an embodiment of the present invention.
Figure 10:
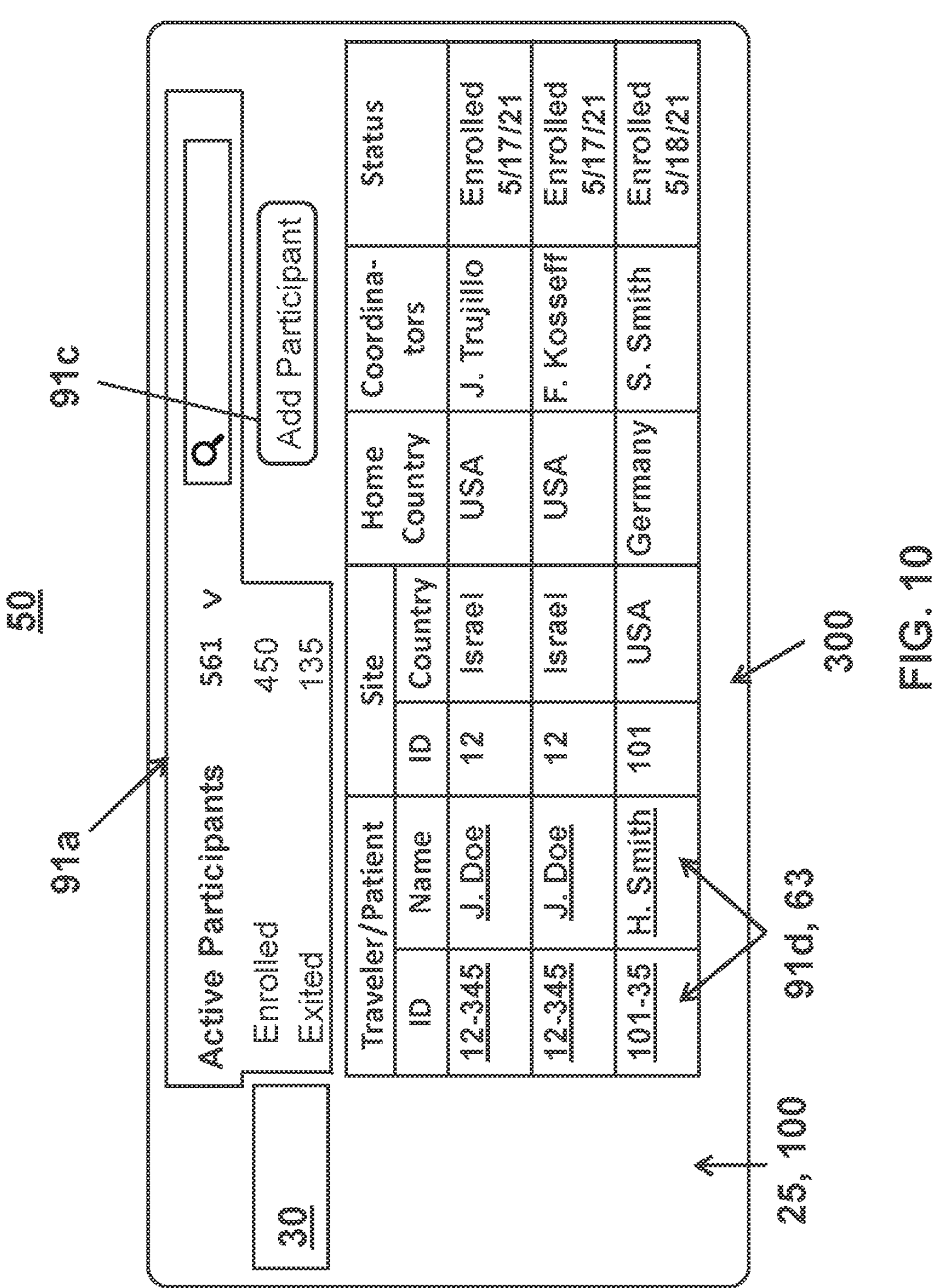
FIG. 10 is a diagram of an embodiment of a clinical study participant graphical user interface in an embodiment of the present invention.
Figure 11:
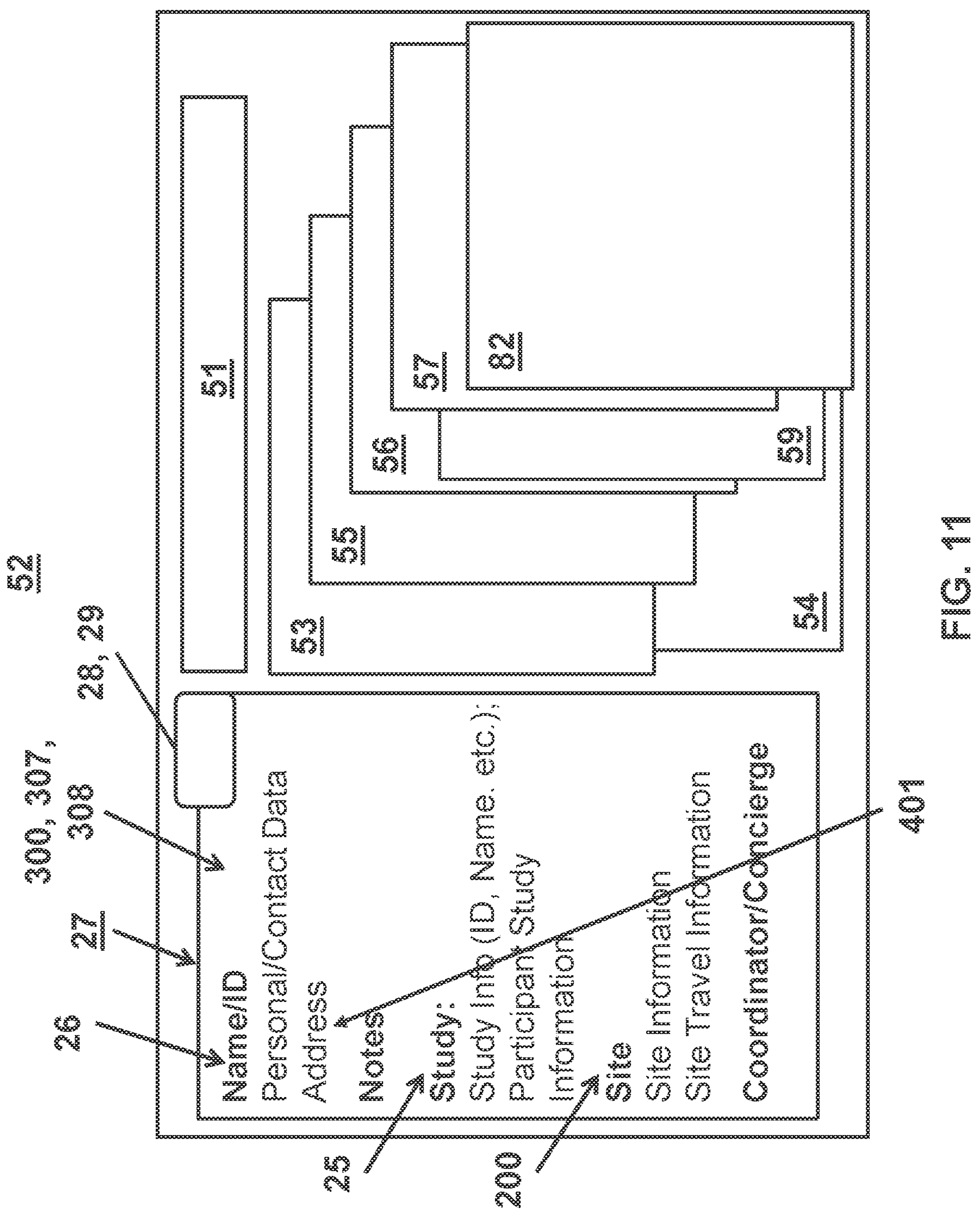
FIG. 11 is a diagram of an embodiment of a clinical study participant graphical user interface in an embodiment of the present invention.
Figure 12:
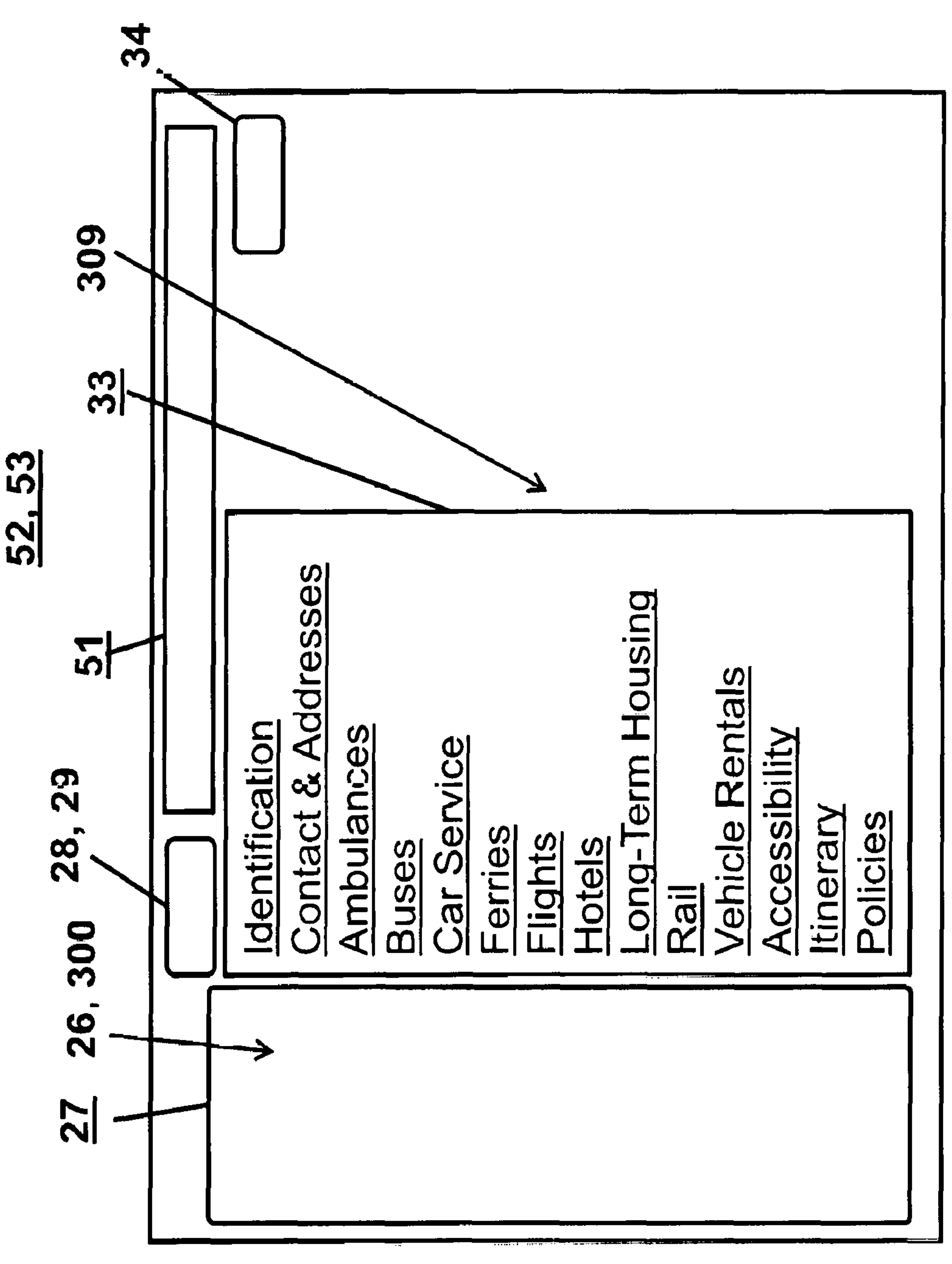
FIG. 12 is a diagram of an embodiment of a clinical study participant travel profile graphical user interface in an embodiment of the present invention.
Figure 13:
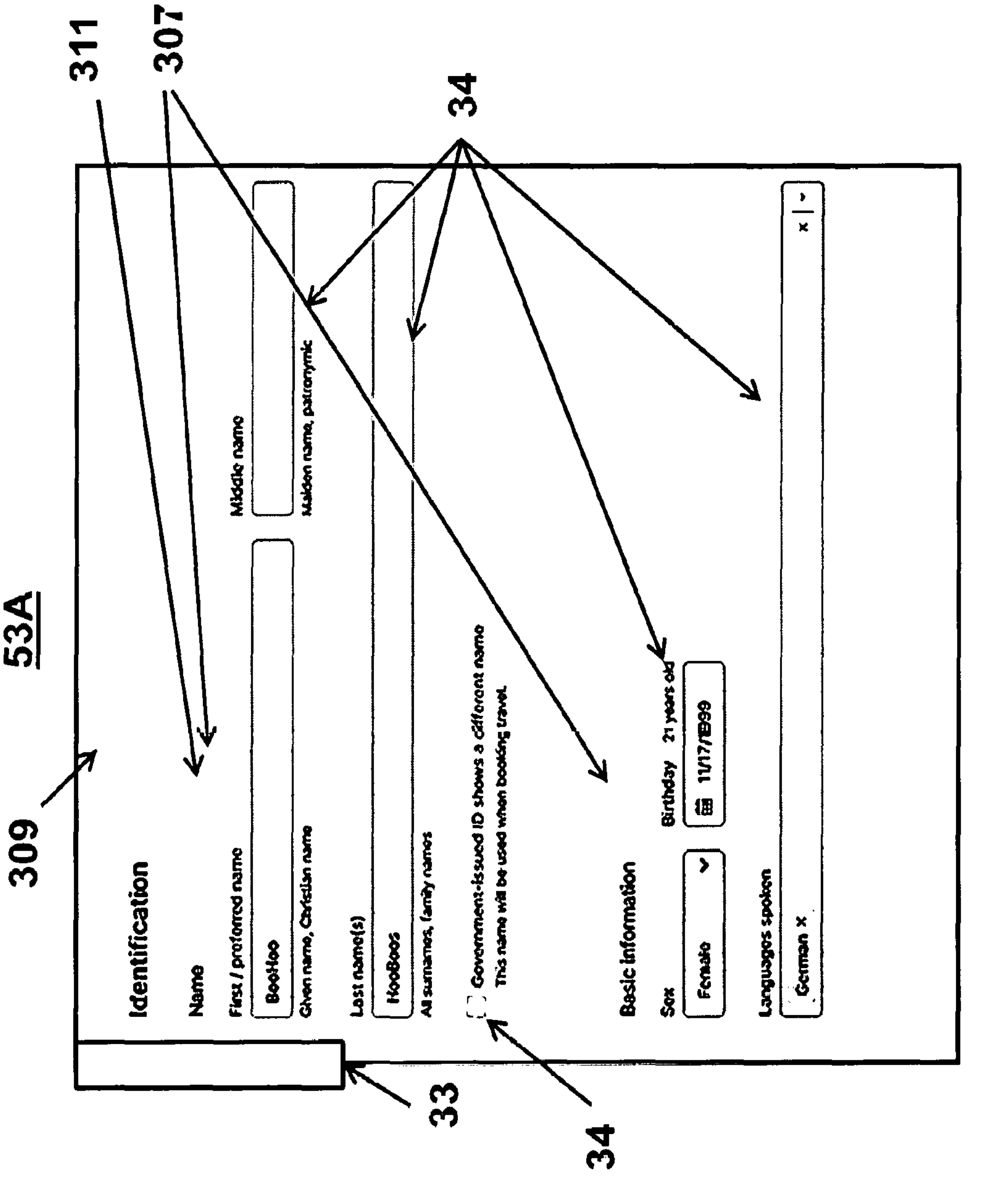
Figure 14:
Figure 14:
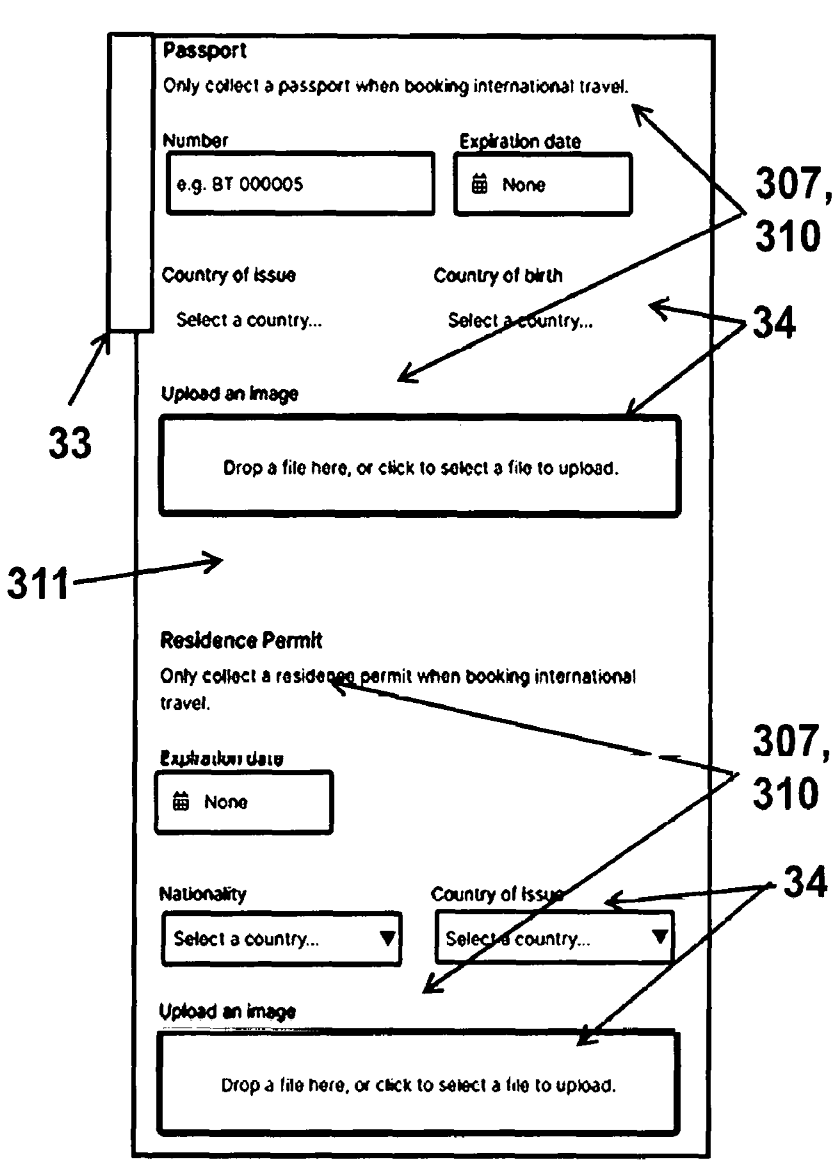
Figure 15:
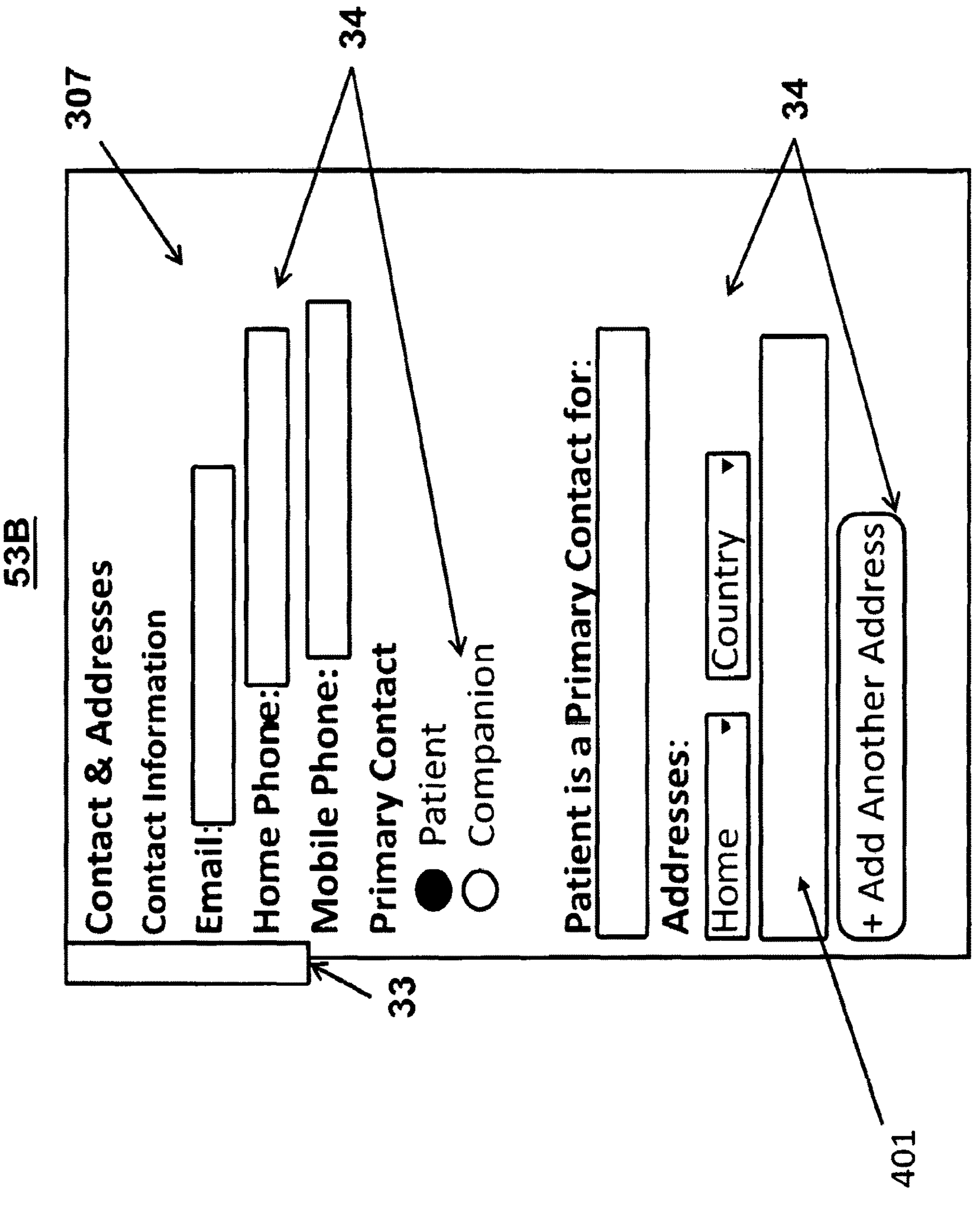
Figures 16, 17:
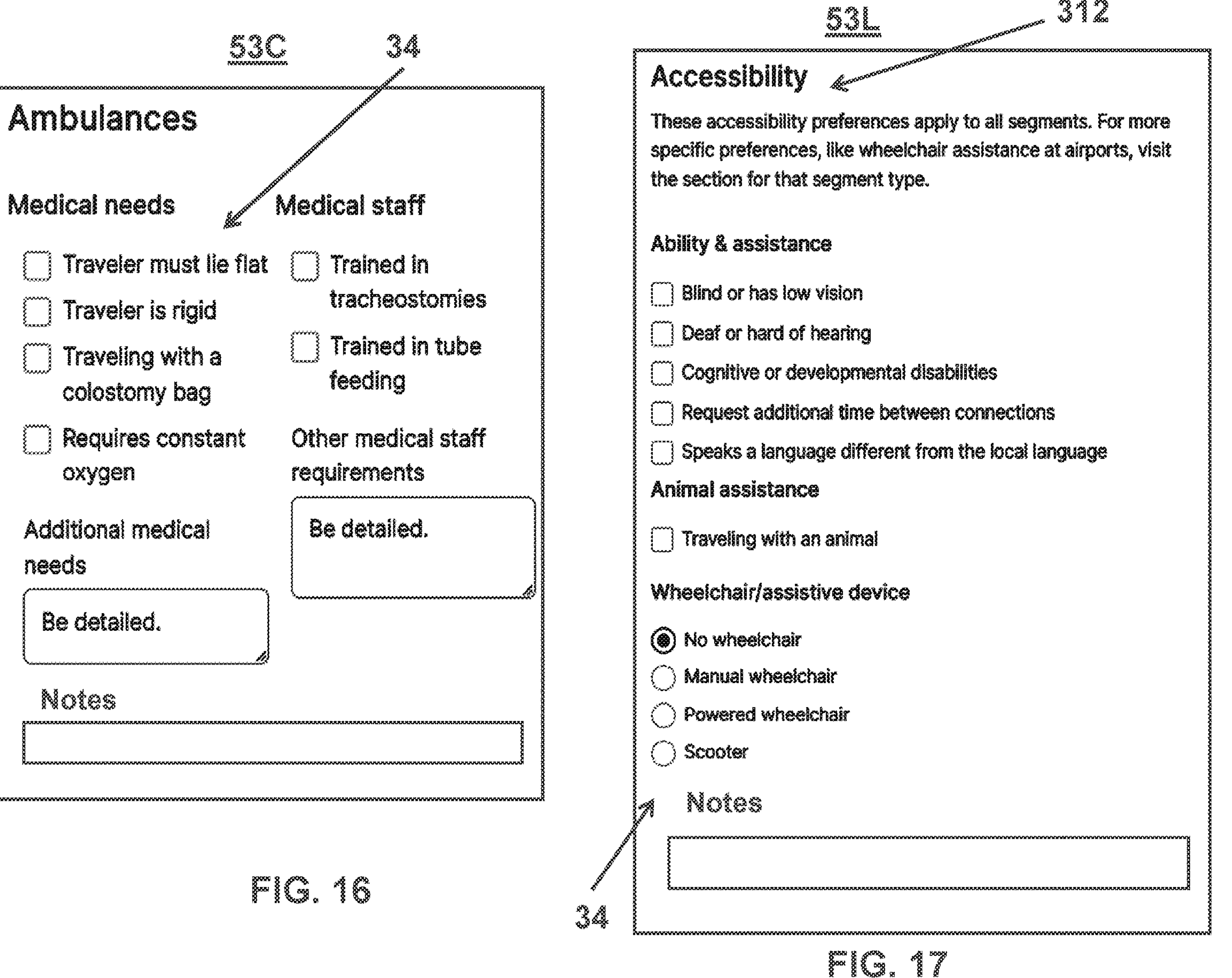
Figure 18:
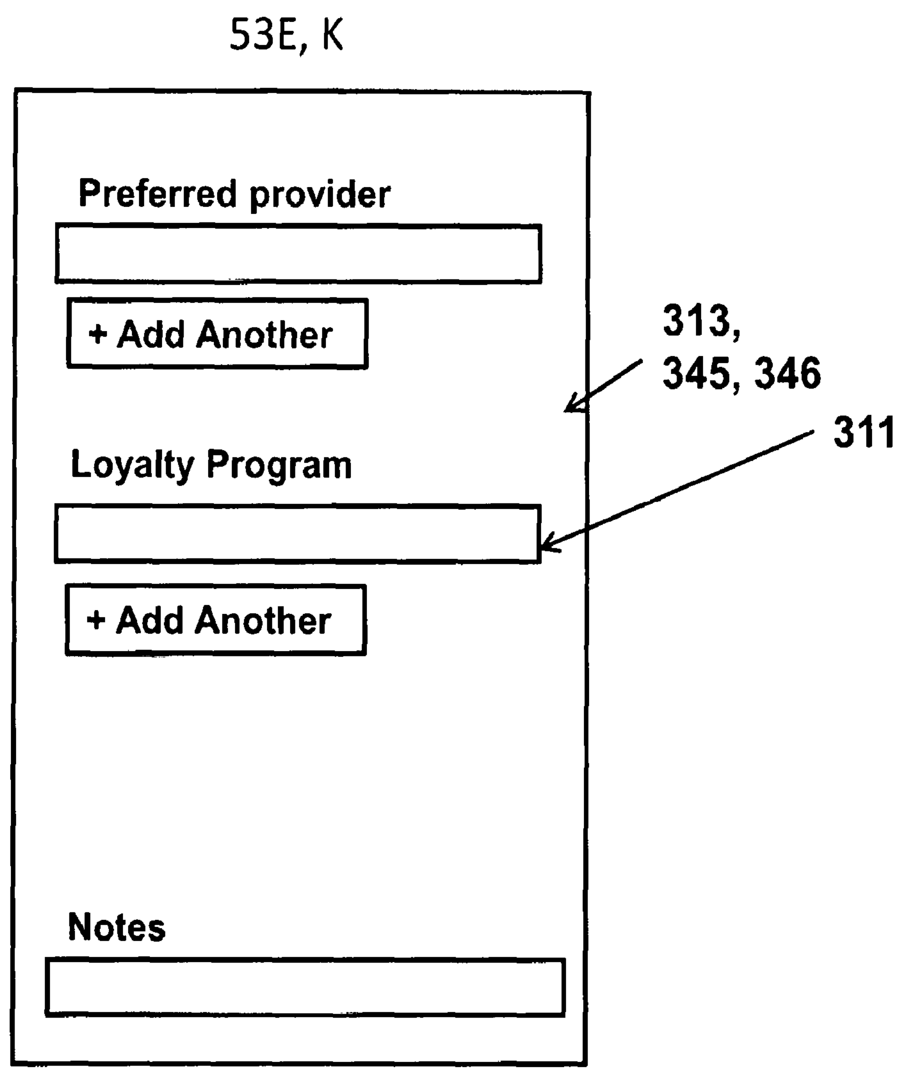
Figure 19:
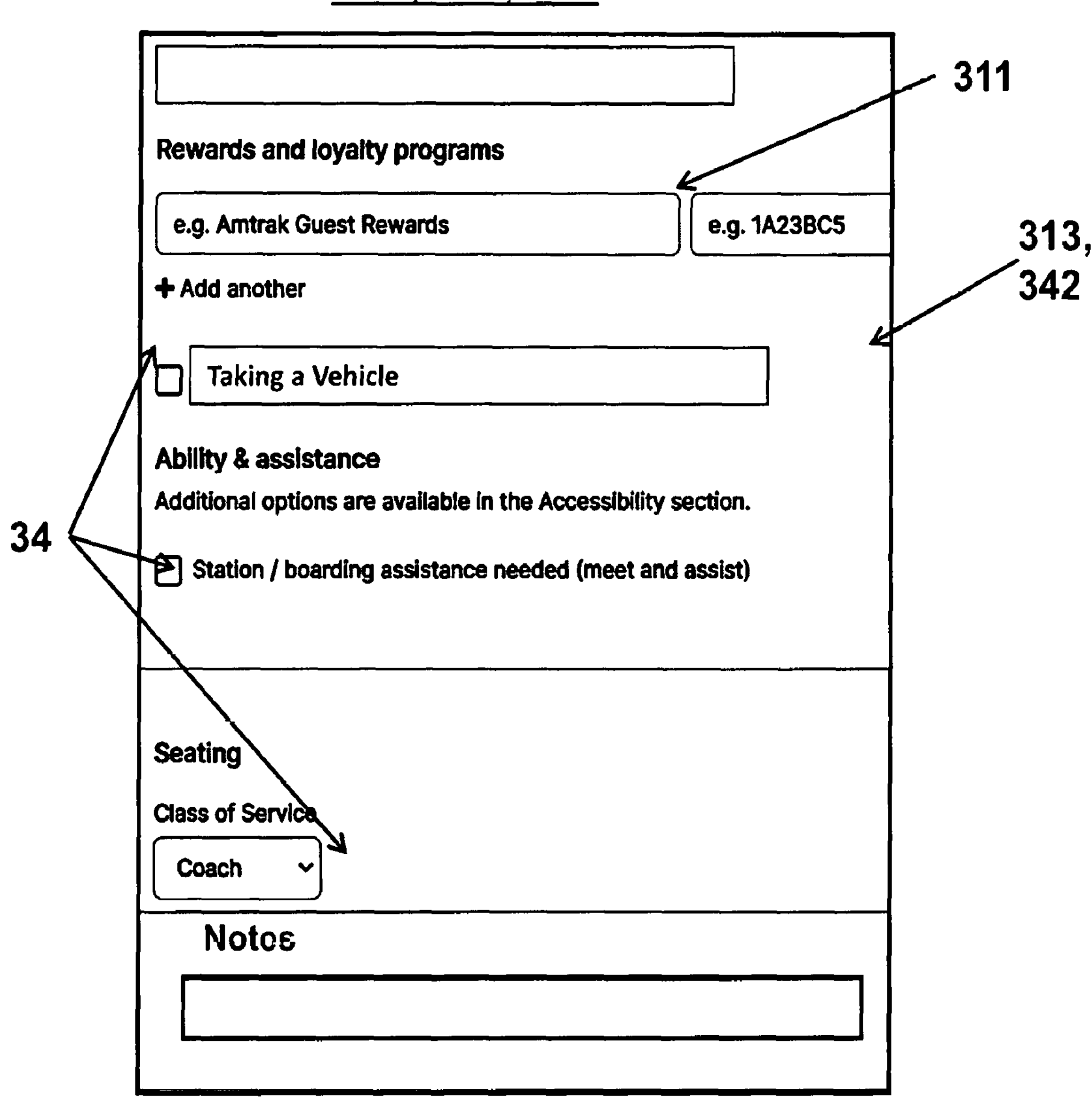
Figure 20:
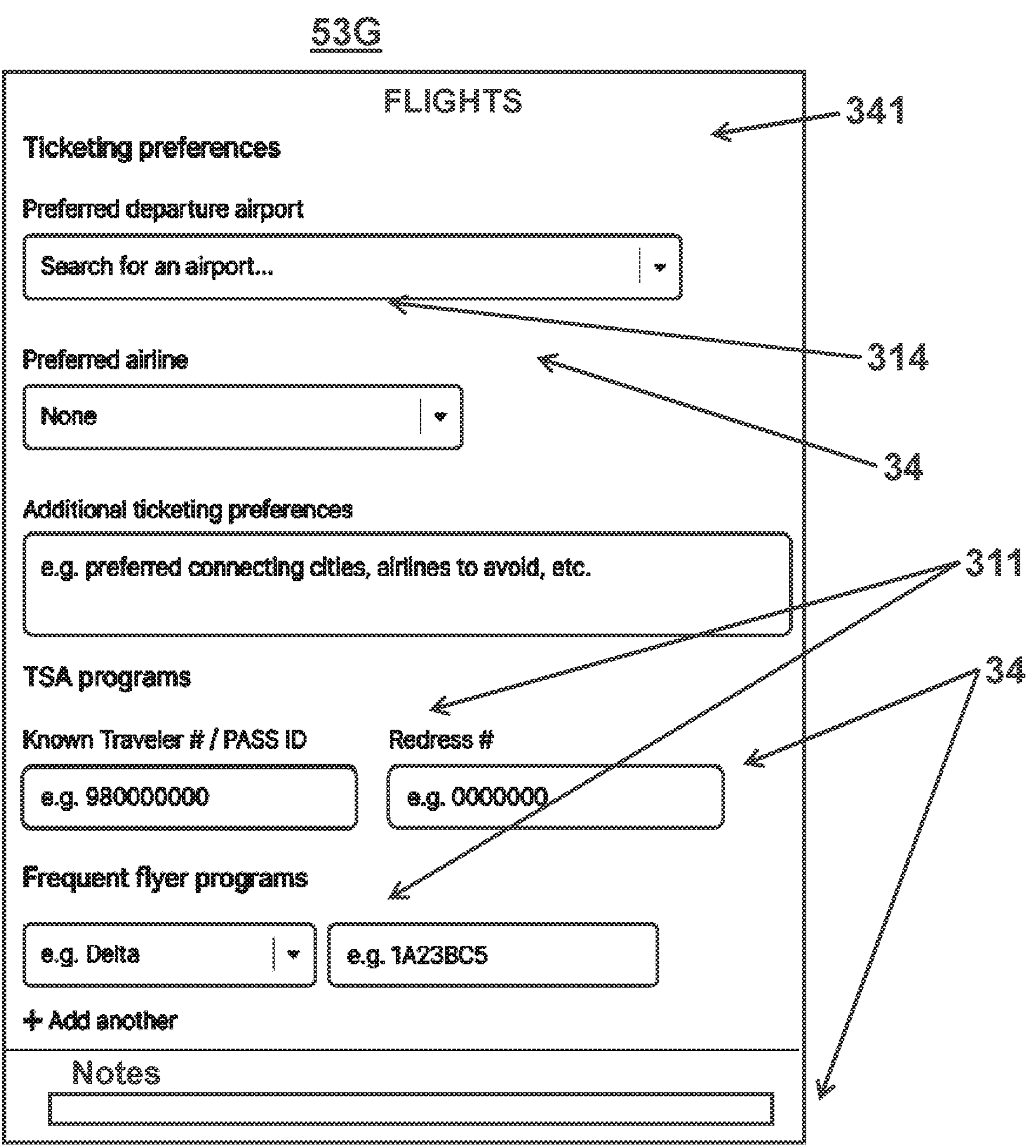
Figure 21:
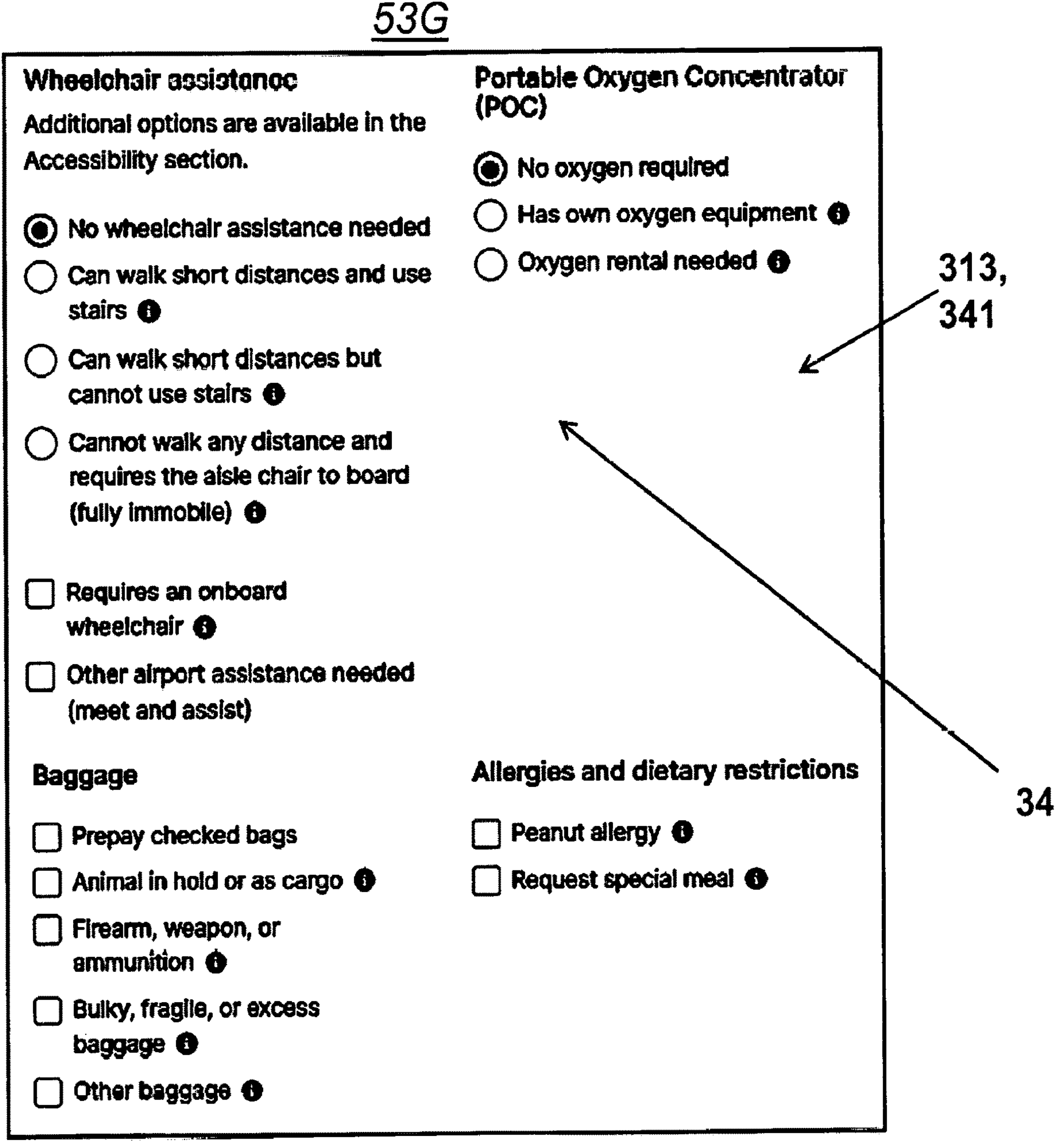
Figure 22:
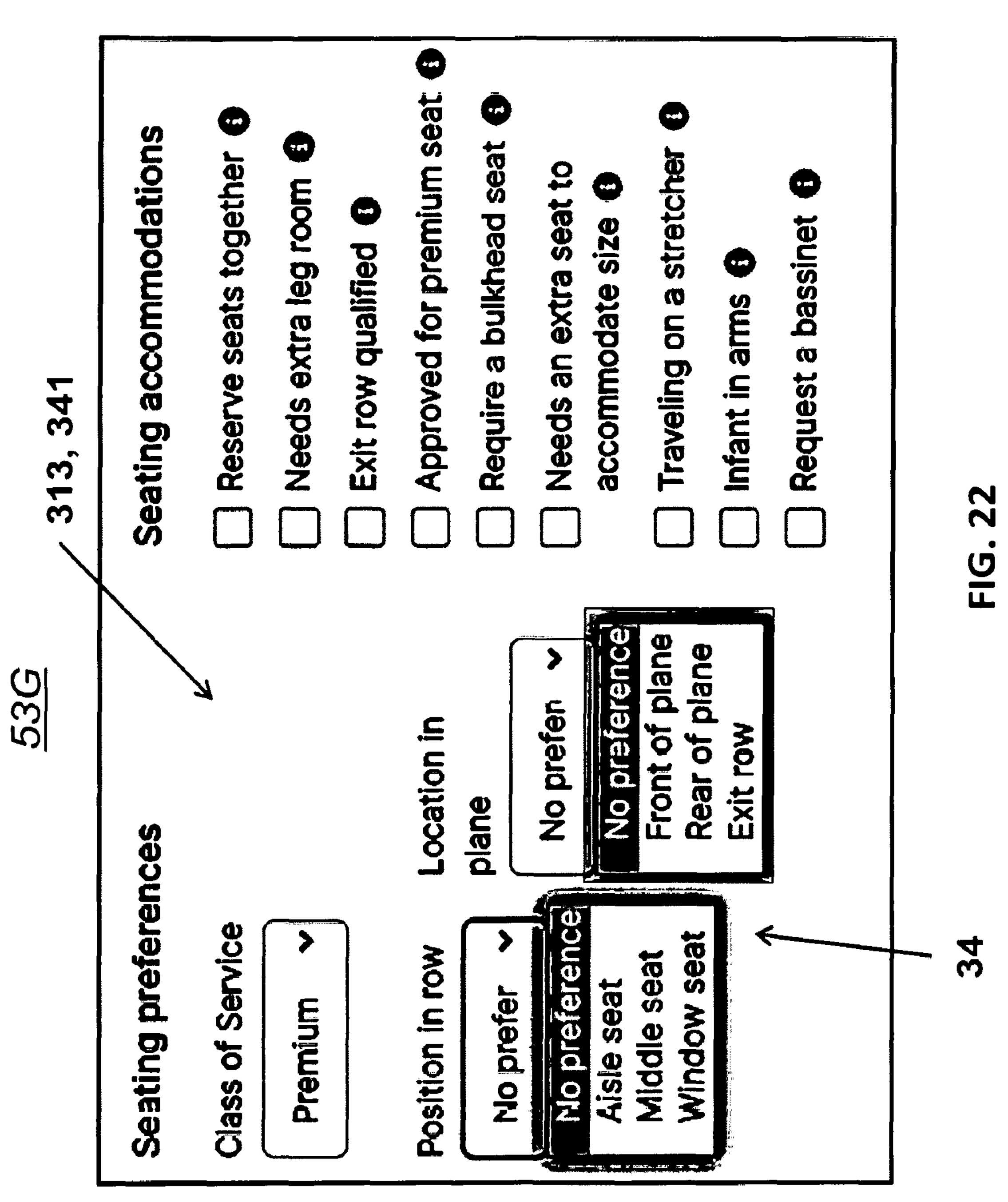
Figure 23:
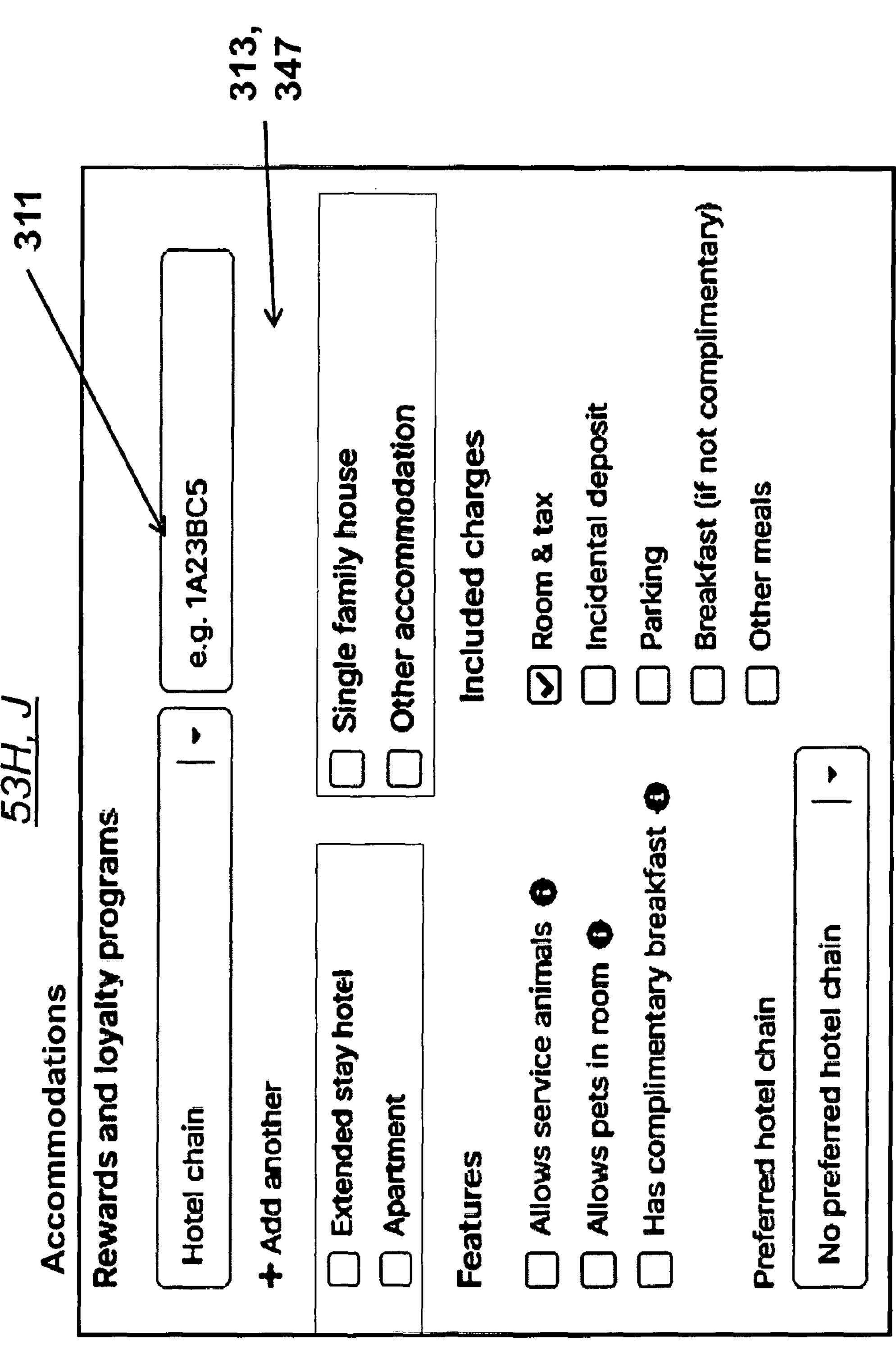
Figure 24:
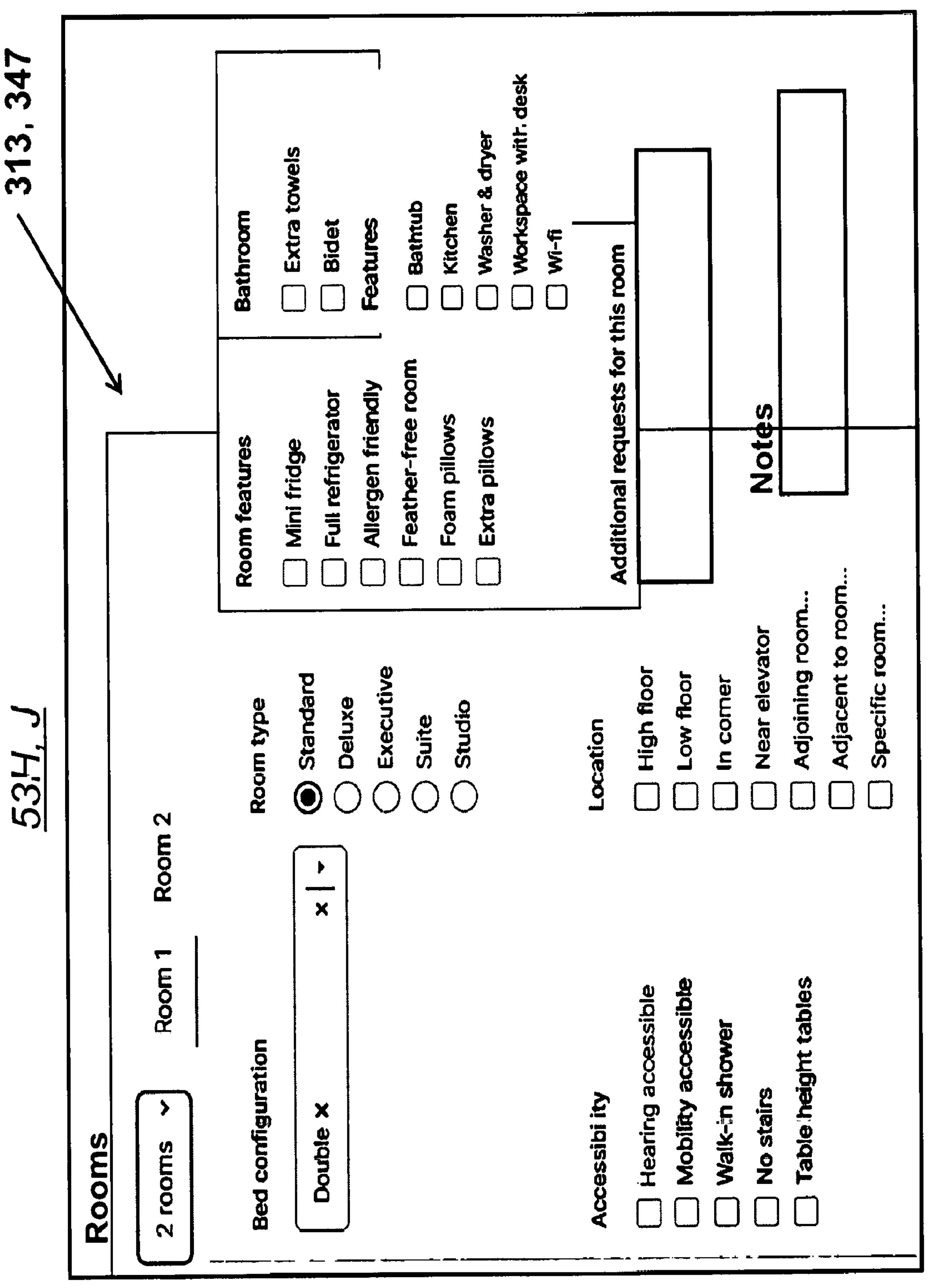
Figure 25:
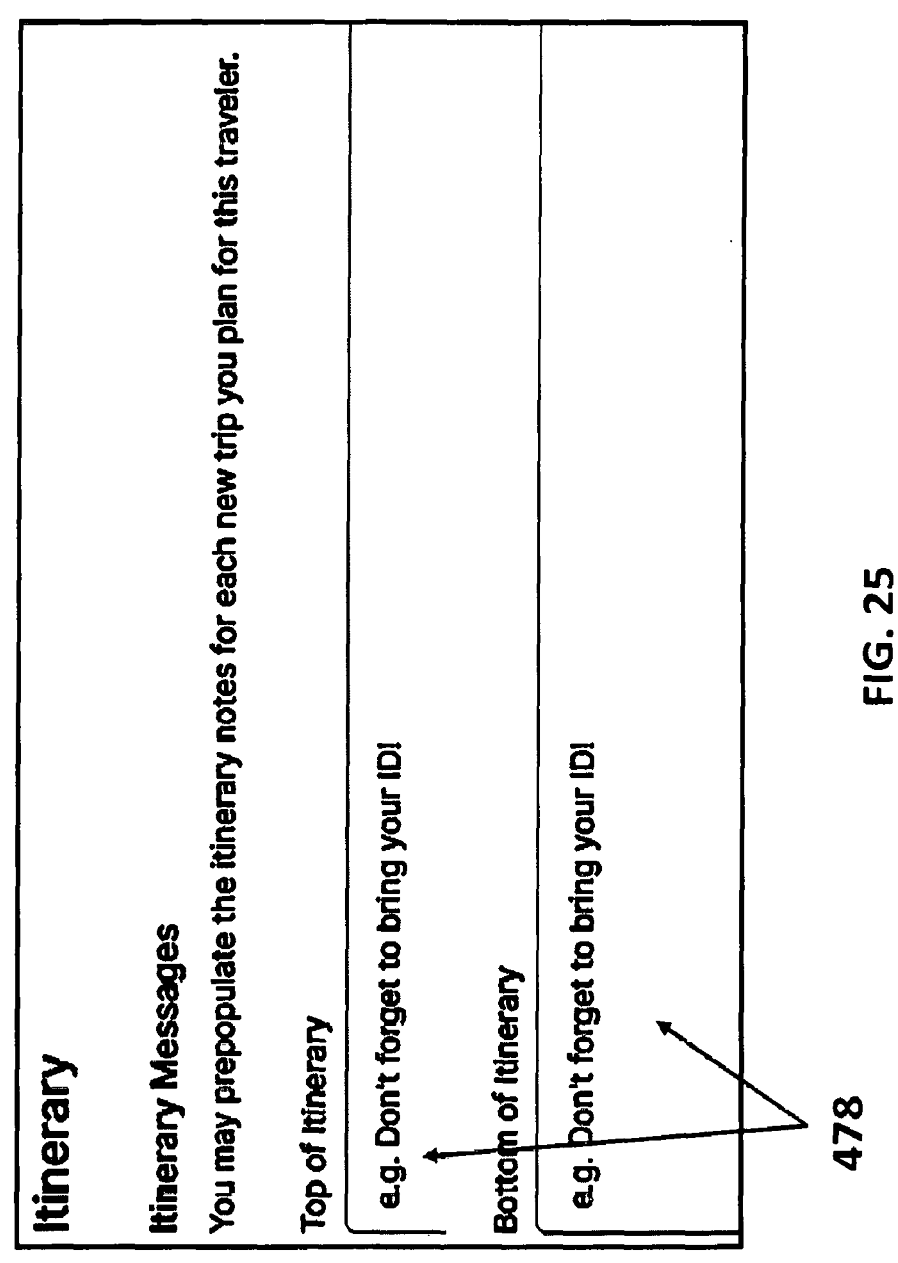

An embodiment of GUI 43 illustrated in FIG. 5, facilitates the efficient input and customization of data as well as efficient navigation through multiple visual panels and views of Data 10, configured to efficiently facilitate different operations, such as entry, modification, and visualization of participant data, clinical site data, travel policies data, user security assignments, visit schedules, travel booking and travel management (including transportation and accommodations), expense management and reimbursement, and various others. The Graphical User Interface 43 comprises a Control panel 44, Main Search user control 45, and Interface 47. In one embodiment, GUI 43 is configured to enable a user to utilize Control Panel 44 and user controls 44*a* to access Interface 47. Embodiments of Interface 47 illustrated in FIGS. 5-9, may comprise various views and/or panels, including, Trips 90, Travelers 91, Available Studies 92, Study 98, Available Sites 93, Site 99, Coordinators 94, Institutions 95, Available Countries 96, and Country 97.

GUI 43, Control panel 44, Main Search User Control 45, and Interface 47 are configured to enable efficient navigation between the different panels, views, and interfaces of GUI 43 to facilitate visualization, management, and customization of data for clinical study participants, study related information, and booking travel arrangements. For example, a user may utilize user controls (e.g., links, buttons) from the Control Panel 44 to access the various views and panels of Interface 47.

Interface 47 may be configured to display various interactive views and panels to permit a user to efficiently provide services for participants, including selecting and booking travel itineraries (e.g., flights, ground transportation, hotels, housing), and providing notes, instructions, and directions for participants and/or travel service providers. Interface 47 of GUI 43 also may be configured to enable input, customization, and/or correction of Participant Data Set 300, to enter new information, correct existing information, or modify and supplement Participant Data Set 300 to reflect individualized requirements and preferences of a participant, for example enabling a participant specific travel policies if warranted. GUI 43 may be configured to enable such input, customization, or correction of Participant Data Set 300 during the provision of concierge services for a participant, or independently of the provision of concierge services, for example, to enter new participants.

Trips View 90 receives from Database 2 information from Trip Data Set 400 about trips associated with one or more studies and displays it indicating trip status (occurred, submitted, in progress, upcoming, booking requested, etc.) and additional trip information (e.g., traveler name, dates, responsible user, origin, destination, and other information). Trips View 90 may be configured to only display trip for travelers that a user currently accessing Trips View 90 interface is authorized to view, for example if a concierge-user accesses Trips View 90, GUI 43 will only receive and display Trip Data 400 for trips associated with those participants for whom the user is authorized to provide services, e.g., a concierge-user will only be able to view the trips associated with the participants that are assigned to the concierge-user, while a user who is allowed to view all participants in the Data 10, may be able to view the trips associated with all participants. Trips View 90 interface provides user controls 90*a*, 90*b*, 90*c* (e.g., pull down list, search box, radio buttons, sliders, etc.) to filter the trip data set 400 in various way, for example by trip status, specific site or study, specific trip or participant, and any other data (e.g., by typing a search term) in Trip Data Set 400. GUI 43 may be configured to enable a user to utilize user control 90*c* associated with a traveler or trip to switch to another interface, for example, Participant Interface 52. A user may utilize user controls 90*a*, 90*b* In one embodiment, Trip View 90 may be displayed through Participant Interface 52 as Participant Trips Module 56 filtered by a participant and may display a user control 485 allowing the planning of a new trip for that participant.

Travelers View 91 receives Study participant data from Database 2 and displays it. It may provide user controls 91*a*, 91*b* (e.g., pull down list; search input control, clicking on a specific traveler) to filter Participant Data Set 300 for a specific traveler (interchangeably referred to as a participant, or patient). Travelers View 91 may also provide user controls 91*c* (e.g., [Add Participant] button), allowing a user to enter information about a new traveler, or 91*d* (e.g., a link, URL) allowing a user to switch to Participant Interface 52 by utilizing control 91*d*. In an embodiment, Travelers View 91 may be displayed through Study Interface 98, as Study Participants Interface 50 displaying Participant Data Set 300 for one or more participants filtered by a Clinical Study 25. Travelers View 91 and Study Participants Interface 50 may be configured to only display Participant Data set 300 that a user currently accessing GUI 43 interface is assigned to, or authorized to view, for example GUI 43 may only receive and display information from Participant Data 300 for participants 26 who are assigned to the concierge-user accessing GUI 43.

Studies View 92 receives data from Database 2 for one or more studies and displays it, providing user controls 92*a*, 92*b*, 92*c*, 92*d* (e.g., pull down list, search box, buttons, clickable links) to filter the displayed studies data by various parameters, add a new study (e.g., [Add Study] button), or utilizing user control 92*d* associated with a study to switch to the Study Interface 98 and view Clinical Study Study Interface receives Clinical Study Data Set 100 for a Clinical Study 25 from Database 2. Study Interface 98 may comprise a study summary area 30 displaying summary information from Clinical Study Data Set 100. Study Interface 98 comprises one or more interface modules/panels, having data views, interactive panels, and/or interfaces, related to a Clinical Study 25, including, Study Overview (46 not shown), Assignments Interface (49 not shown), Study Participants Interface 50, Participant Interface 52, Study Sites Interface 60, Travel Policies Interface 70, Visit Schedule Interface 80, Study Coordinators Interface (not shown), and others. GUI 43 may be configured to provide Navigation User Controls 31 (e.g., tabs, links, button, lists, menu items, radio controls, search boxes, and others) within Study Interface 98 allowing a user to utilize the Navigation User Controls 31 to switch to different views or panels of Study Interface 98, or Interface 47, to view, input, or manipulate data about Clinical Study 25, and manage Participants 26.

Study Overview 46 may be configured to display summary and overview information (e.g., automatically generated and/or aggregated from Data 10, or Clinical Study Data Set 100) related to a Clinical Study 25.

Assignments Interface 49 may display a list of users with access to the system and their assignments (e.g., levels of access, specific sites or participants, etc.). For example, in some embodiments, Assignments may display a list of users who are tasked to provide concierge-type services (interchangeably referred to here as users, coordinators, or travel coordinators) together with the participants who are assigned to each of those users, or travel coordinator. A coordinator may be assigned to participants based on various factors, for example participants associated with a clinical site, participants residing or visiting a particular country, or participants whose language the coordinator speaks. A coordinator may also be assigned a single participant, so that a system according to the present invention will permit the coordinator to only access Participant Data Set 300 of that single participant, and no one else's Participant Data Set 300.

Study Participants Interface 50 may display a list of participants in a study who have opted to use the concierge services facilitated by a system according to the present invention. Study Participants Interface 50 is configured to display a Participant Interface 52 by utilizing a user control 63 (e.g., clicking on a participant). Participant Interface 52 may also be accessed by utilizing the control panel 44, or the Main Search User Control 45.

Participant Interface 52 may receive Participant Study Data 300 about Participant 26 from one or more of Database 2, input device 41, network data transmission and other methods, and displays Participant Data Set 300. Participant Interface 52 may comprise a participant summary area 27 displaying summary information from Participant Data Set 300 about participant 26. Participant Interface 52 may comprise Participant Data User Controls 28 configured to enable a user to input, correct, and customize Participant Data Set 300 for Participant 26, by utilizing user control 28 and input device 41. For example, by utilizing user control 28, a user may enter, or modify information about a Participant, such as Participant ID, Participant Site, notes concerning a participant, Participant Enrollment date, and may also Rollover a Participant to another clinical study (e.g., extension study), exit a Participant from a study, remove Participant as travel companion, and various other functions. Participant Interface 52 may also be configured to allow a user to utilize a Site Data User Control 29, and coordinator user controls (not shown) directly from Participant Interface 52. Participant Interface 52 may comprise one or more interface modules having one or more of data views, interactive panels, and interfaces, including Travel Profile module 53, Companion module 54, Participant Travel Policies module 55, Participant Trips module 56, Participant Consent Interface 57, Participant Visit Schedule Module 82, and Participant Expenses Interface 65, each of which may be displayed by a user by utilizing a Participant User Control 51.

Travel Profile module 53, receives Traveler Profile 309 data from Database 2, and provides user controls to input, change, modify or customize Traveler Profile 309. Travel Profile module 53 may be viewed in a Identification View 53*a*, Contact & Addresses View 53*b*, Ambulances View 53*c*, Buses View 53*d*, Car Service View 53*e*, Ferries View 53*f*, Flights View 53*g*, Hotels View 53*h*, Long-Term Housing View 53*i*, Rail View 53*j*, Vehicle Rentals View 53*k*, Accessibility View 53*l*, Itinerary View 53*m*, Policies View 53*n*, each of which may be configured to display, and enable input and modification of, Traveler Profile Data 309. Travel Profile module 53 may comprise Traveler Profile Navigation User Control 33 allowing a user to utilize it to switch one of the Travel Profile Views 53*a*-53*n*, and a Traveler Profile User Control 34 allowing a user to utilize it to input, modify, or manipulate Traveler Profile Data 309. Traveler Profile Navigation User Control 33 may also be configured to allow a user to utilize it to switch any other interface 47, or to any view, module, or interface within participant interface 52, including Companion module 54, Participant Travel Policies module 55, Participant Trips module 56, Participant Consent Interface 57, Participant Visit Schedule Module 82, and Participant Expenses Interface 65.

Travel Profile module 53 may also be configured to transmit Traveler Profile 309 to be stored in Database 2.

Companion module 54, receives Companion Data Set 325 from Database 2, and provides user controls to input, change, modify or customize Companion Data Set 325. Companion module 54 may also be configured to transmit Companion Data to be stored in Database 2.

Participant Travel Policies module 55 enables viewing and customization of Participant Data 300 related to Study Travel Policy 150 applicable to a participant 26 for a clinical site visit trip, based on Main Travel Policy 151 and applicable Specialized Travel Policies 152. Participant Travel Policies Module 55 allows a participant to be associated or dissociated with a Specialized Travel Policy 152 by utilizing user controls 58 to add or remove a Traveler Policy Label 321 and/or a Visit Policy Label 131 associated with participant 26. Embodiments may be configured to require an approval (from, e.g., manager) to create and/or customize a Specialized Travel Policy 152, Traveler Policy Labels 321, and/or Visit Policy Labels 131*a*. If such approval is required, Specialized Travel Policy 152, Traveler Policy Labels 321, and Visit Policy Labels 131 additions and changes may occur after approval is granted.

Participant Trips Module 56 may display information about past and upcoming participant trips, based on data from a Trip Data Set 400 and associated Participant Data Set 300 received from Database 2. Participant Trips Module 56 may display information identifying a participant who is taking the trip, a trip status (e.g., pending, submitted, requested, booked, confirmed, etc.), a trip destination, method of transportation, trip schedule, and other information related to a participant trip. Participant Trips Module 56 may be configured to provide user control 485 that enables a user to switch to the Travel Planning Interface 500 (e.g. to plan a new trip, modify existing one), or clickable link user control 90*b* embedded in an individual trip text enabling a user to display an Individual Trip 59 module.

Individual Trip 59 module is configured to receive from Database 2, display, and enable modification of, itinerary 475 data, for example Trip Details 476, Trip Planning History 477, Trip Segment Data 501, Itinerary Message 478, and other relevant information based on Itinerary 475 data. Individual Trip 59 module may be configured to provide user controls enabling a user to switch to other interface modules of GUI 43 and to enter and/or modify various data. For example, a user may utilize user control 480 (e.g., to take Itinerary Actions) to cancel a trip, or Request Booking of Trip Segments by transmitting to Booking Module 575 data necessary for travel booking, for example, Trip Segment Data 501, Traveler Identification 311, and/or other data needed for travel booking customized according to study and participant preferences and requirements. User control 480 may also be utilized to send Itinerary 475 to one or more recipients according to traveler contact information 308 and/or the site contact information 202, by utilizing transmission methods and transmission destinations, or recipients, provided in traveler contact information 308 and/or the site contact information 202. For example, Itinerary 475 may be sent by emailing it to an email address provided in traveler contact information 308 and/or site contact information 202, or may be sent by facsimile if so indicated in traveler contact information 308 and/or site contact information 202. Traveler contact information 308 and/or site contact information 202 may also indicate that Itinerary 475 and other information may be sent by transmitting over a network connection (using, e.g., API calls, secure data/file transfer protocols, and other methods) to a computing system capable of receiving Itinerary 475. Such a computing system may be a clinical site computer system, a system associated with a patient in a hospital or another facility, a patient's computing device having appropriate software, and others. An embodiment of the invention may be configured to enable secure online viewing and/or downloading of Itinerary 475 or other information, by providing a secured portal accessible by authorized persons. In this example, a contact identified in Traveler contact information 308 and/or site contact information 202 will be notified using the provided notification method (e.g., email, fax, API, mobile phone notification, personal computing device notification, and others) and the notified contact may log in through the secured portal using a mobile or desktop device to view and or download Itinerary 475.

Individual Trip 59 module may also be configured to provide user controls 481 enabling a user to modify Individual Traveler Policy 320, or add travelers (such as travel companions) to Itinerary 475. Individual Trip 59 module may also be configured to provide user controls 483 to add or modify Trip Segments by loading the Travel Planning Interface 500. In one embodiment, user control 483 may be associated with the trip Segment Start Location 503 or with the trip segment end location 504 of an existing trip segment data 501. In such an embodiment a user may utilize user control 483 to add a new trip segment 501, having a segment start location 503 or a segment end location 504 based, respectively, upon the segment end location 504 or the segment start location 503 of the existing trip segment data 501. For example, if user control 483 is associated with a Segment Start Location 303 that is a departure airport for an existing flight trip segment 513, a user may utilize user control 483 to add a Car Service Trip Segment 514 having a trip segment end location 504 be the departure airport location of Flight Segment 513.

Participant Consent Interface 57 receives from the Database 2 and displays Participant Consent Record 330 and provides user controls 45 (e.g., slider, checkbox, button, upload controls) allowing a user to modify and change Participant Consent Record 330. For example, a user may utilize the user Consent controls 45 to indicate whether a participant 26 has provided informed consent for the use of Participant 26 Personal Information, including health information, and to upload signed data consent forms for Personal Information, including health records. User Consent control 45 may also be configured to initiate a scrubbing (e.g., indicated as "Scrub Traveler"), or removal, of a participant 26 Personal Information and health records data, or all participant 26 data, from Database 2, and in general from the entire system 1.

Participant Expenses Interface 65 receives from the Database 2 and displays Participant Expense Data 360 for viewing, and may also provide user controls allowing a user to modify and change Participant Expense Data 360. For example, a user may utilize the user controls to receive (e.g., import for a computer or over a network, drag and drop, etc.) Participant Tax Data 361 (e.g., Tax ID, Social Security Number, IRS forms, such as W9, and others), indicate support activities provided to a participant 26, add or change status of expenses, and expense rules and policies (e.g., reimbursable, limits, etc.). GUI 43 may also be configured to enable automatic, or user initiated, check or validation of tax information, e.g., received in Participant Expenses Interface 65, from a W9 form, or collected elsewhere. In one embodiment, such check or validation of tax information may involve utilizing the US internal Revenue Service (IRS) Taxpayer Identification Number (TIN) Matching Tools, by for example, providing, transmitting, and/or querying tax information to an IRS TIN Matching Tool and receiving from the IRS TIN Matching Tool information about the tax information, for example, TIN validation information.

Study Sites Interface 60 receives (e.g., from Database 2, input device, data transmission, etc.) and displays Clinical Site Data Set 200 for sites associated with Clinical Study 25. Study Sites Interface 60 is configured to enable a user to input, correct, or customize Clinical Site Data Set 200 by utilizing, for example, Site User Control 29 and input device 41. Study Site Interface 60 may be configured to display the same Clinical Site Data set 200 as Site Interface 93 may display if a user utilized user controls 92*a*, 45 to filter the information in Site Interface 93 by Clinical Study 25.

Travel Policies Interface 70 may receive Study Travel Policy 150 data from Database 2, input device 41, direct data transmission, and other methods and displays Study Travel Policy 150 about a clinical study 25. Travel Policies Interface 70 may be configured to enable a user to utilize various user controls 159 and policy labels to modify and customize the Study Travel Policy 150 data so that different travel policies apply to different types of travel or travel circumstances. Embodiments of Travel Policies Interface 70 may be configured to require an approval (from, e.g., manager) to create and/or customize a Specialized Travel Policy 152, Traveler Policy Labels 321, and/or Visit Policy Labels 131*a*. If such approval is required, Specialized Travel Policy 152, Traveler Policy Labels 321, and Visit Policy Labels 131 additions and changes may occur after approval is granted, which may be granted once or on a per need basis.

For example, Travel Policy Interface 70 provides Travel Rules user controls 159 that enable a user to add new, import, preview, customize, add to, or modify, a Study Travel Policy 150 data to create and store in Database 2 a Main Study Travel Policy 151, and a Specialized Travel Policy 152 that applies different travel policies to travel based, for example, on a participant's country, on a clinical site associated with a participant, and on other parameters. The Travel Rules User Controls 159 further enable a user to create and store in Database 2 a Traveler Label 321 and a Visit Policy Label 131 and create Specialized Travel Policy 152 that applies to travel in which a traveler is associated with a Traveler Policy Label 321, Visit Policy Label 131, or both. User control 159 may be utilized to create other types of policy labels, such as country policy labels, site policy labels, site location policy labels, and various other travel endpoints, or circumstances.

Visit Schedule Interface 80 receives (e.g., from Database 2, input device, data transmission, etc.) and displays Study Visit Schedule 130 data. Visit Schedule Interface 80 may be configured to enable input, correction, or customization of Study Visit Schedule 130 data utilizing input device 41. Visit Schedule Interface 80 may provide user controls that are configured to modify Study Visit Schedule 130 data by adding, or modifying information about, Visits, Visit Tracks (e.g., clinical protocol arms or patient groups, visually represented as a branch or track in the visit sequence), visit cycles (e.g., repeating one or more visits until a condition is met), Visit Jumps (e.g., if conditions are met a participant may omit or repeat visits, switch arms/groups, and in general switch to another point in the visit schedule as defined by the configuration of the jump node), Information (e.g., about a Visit, group of visits, the Visit Schedule), and others. Visit Schedule Interface 80 may also provide user controls to enable a user to add a Visit Policy Label 131 to Study Visit Schedule 130. Visit Policy Label 131 may be associated with one or more visits, tracks, cycles, and other visit schedule attributes enabling customizable travel policies.

Participant Visit Schedule Module 82 receives (e.g., from Database 2, input device, data transmission, etc.) and displays Participant Visit Data 304 for a Participant 26. In a preferred embodiment, Visit Schedule Interface 82 may be configured to provide a Participant Visit User Control 36 and Participant Travel User Control 485 associated with a Current Visit 306 from Participant Visit Data 304. A user may utilize user control 36 to skip a Current Visit 306, and user control 485 to begin planning a new trip and switch to Travel Interface 500. Participant Visit User Control 36 may also be associated with other visits from Participant Visit Data 304, in which case a user may utilize user control 36 to fast forward to that visit, or to make that visit a current visit 306.

Sites View 93 receives from Database 2 Clinical Site Data Set 200 for clinical sites associated with one or more clinical studies 25 and displays the Clinical Site Data Set 200 or portions of it. Sites View 93 may provide user controls (e.g., pull down list, search box, buttons, clickable links) to filter the displayed data by various parameters (e.g., by study, country, search text, and others), to switch to Site Interface 99, and to enable other functionality. For example, in one embodiment, a search user control may be utilized to filter Sites View 93 by study resulting in displaying Sites View 93 as Study Sites Interface 60. In another example, a user control (e.g., "Add Site") may be provided enabling a user to utilize the user control to add new clinical sites by loading Site Interface 99 and importing Site Data 200. Or a user control (e.g., clickable link, button, image) may be provided, and associated with a specific site enabling a user to load Site Interface 99 with data from Clinical Site Data Set 200 for a particular site and enabling a user to view and/or modify Clinical Site Data 200.

Site Interface 99 may comprise one or more interface modules having data views, interactive panels and/or interfaces, including, Site Participants module (e.g., study participants associated with a site), Site Assignments module (e.g., users, concierge-users, and other persons assigned to study participants associated with a site), Site Travel Policies module (e.g., travel policies associated with a site, including visit labels for visits at the site, and traveler labels for participants associated with the site), and others. The Site Interface may provide a Site User Control 29 enabling a user to add a new site, and enter, or modify Clinical Site Data 200 for a clinical site.

Coordinators View 94 receives from Database 2 data about coordinators associated with one or more studies and displays them. It provides user controls (e.g., pull down list, search box, buttons, clickable links) to filter the displayed studies data by various parameters, and an [Add Coordinator] user controls. In one embodiment, Coordinators View 94 may be displayed as Study Coordinators 94 displaying coordinator data for one or more coordinators associated with a specific study. Coordinators 94 may also provide user controls to access an individual Coordinator Interface receiving and displaying Coordinator/User Data 115, including coordinator assignments, coordinator sites, and coordinator participants. Individual Coordinator interface may provide user controls enabling participants to be reassigned or to configure auto assignment of participants.

Institutions 95 receives from Database 2 data about Institutions (e.g., universities, hospitals, doctors' offices, medical facilities, and other entities) that may be associated with one or more studies or clinical sites. It provides user controls (e.g., pull down list, search box, buttons, clickable links) to filter the displayed Institutions data by various parameters, and/or to add institutions (e.g., "Add Institution" button).

Countries View 96 receives from Database 2 data about various Countries, for example, where participants or clinical sites associated with one or more studies are located. It provides user controls (e.g., pull down list, search box, buttons, clickable links) to filter the displayed countries data by various parameters. In one embodiment, Countries View 96 may display countries associated with a specific study or specific sites.

Country 97, interface comprises one or more panels and/or views, including, Country Studies (e.g., clinical studies 25 that involve the country), Country Sites (e.g., clinical sites serving the country), Country Coordinators (e.g., user who serve participants and or sites associated with the country), Country Participants (e.g., participants associated with the country), and County Notes (e.g., notes related to the country).

By way of example, GUI 43 is configured to allow access to the various views and panels of Interface 47 by utilizing (e.g., selecting, clicking, touching, pointing, typing, etc.) various user controls (e.g., tab, button, pull down list, menu, search input, etc.). For example, Assignments Interface 49 may be accessed by utilizing an Assignments user control, Participants Interface 50 may be accessed by utilizing a user control 51, Study Sites Interface 60 may be accessed by utilizing a user control 61, Coordinators Interface 94 may be accessed by utilizing a user control 94*a*, Travel Policies Interface 70 may be accessed by utilizing user control 71, and Visit Schedule Interface 80 may be accessed by utilizing Visit Schedule user control 81.

Private Cloud 6 may be any combination of networked computing resources (e.g., databases, servers, gateways, etc.) that are securely isolated from the Internet (using, e.g., private networks, Local Access Networks, firewalls, secured gateway, etc.). In preferred embodiments, private cloud 6 is a virtual private cloud (VPC) that uses shared computing infrastructure and resources, but isolates the private cloud 6 resources, such as Database 2, servers 3, and others, using private subnets, virtual private networks (VPNs), encrypted channels, and/or other methods that are well known to someone skilled in the art. Many providers provide VPC that can be utilized for private cloud 6, such as Amazon VPC, Google VPC, Rackspace VPC, Microsoft Azure, and others. Other embodiments may utilize a non-virtual private cloud 6 that uses dedicated computing infrastructure residing on or off premises, in a private data center, or with a managed private cloud provider (e.g., RackSpace, Cloudreach, etc.).

Virtual Private Clouds can be implemented with hardware and software network security systems that are consistent with privacy law and regulations compliance (e.g., GDPR, HIPAA). Such features may include data encryption tools 11, monitoring tools 20, network gateways securing access to private cloud 6, such as Internet Gateway 7, API Gateways 8, and others.

Encryption tools 11 may be configured to encrypt Data 10 at rest, while stored in Database 2, and to unencrypt data records of Data 10 when those data records are accessed by GUI 43, or by another computing resource authorized to access Data 10. Encryption tools 11 may be configured to encrypt the entire Database 2 for example, a Transparent Data Encryption (TDE) tool 11, or specific records, cells, or data in Database 2. Encryption tools 11 may be configured to encrypt data sent to Database 2 (e.g., client-side encryption), for example in steps 1101, 1102, 1104 of FIG. 3, or encrypt data upon storing it in Database 2 (e.g., server-side encryption), for example in Step 1103. Encryption tools 11 may be software solutions separate from Database 2 and/or Private Cloud 6, or may be integrated with them. Encryption tools 11 may be independently developed tools, or developed using various third-party cryptographic services, solutions, or software development kits/toolkits (SDKs) (e.g., Azure Storage Service Encryption, Oracle Databases integrated TDE, AWS Encryption SDK, Google Cloud Encryption, IBM Guardium Data Encryption). Encryption tools 11 may utilize various encryption methods or algorithms, preferably cryptography encryption utilizing an encryption key 13 and a Key Management Service (KMS) system 14 that provides further security by separating the encryption key from encrypted Data 10. Encryption KMS systems can implement hardware or software encryption keys, separate the keys from data (e.g., only user external to the Database 2 has the key), handle the keys securely (e.g., allowing access to keys using a separate security policy), periodically generate new keys, and/or rotate keys. Various private cloud vendors provide encryption KMS systems, such as Google Cloud KMS, Amazon AWS KMS, Microsoft Azure Key Vault, Oracle Wallet, Oracle Key Vault, and others.

Internet gateway 7 may be utilized for enabling secure communications between the private cloud 6 and the Internet. Internet gateway 7 may connect (e.g., as an additional network "node") the Private cloud 6 and the Internet. In an embodiment, Private Cloud 6 comprises a public subnet accessible by the public internet through Internet Gateway 7 and a private subnet, isolated from Internet Gateway and not accessible from the Internet. Internet Gateway 7 allows secure transmission of Personal Information over the public internet. In a preferred embodiment, Private Cloud 6, Server 3, Internet Gateway 7, and workstation 40 communicate using HTTPS protocol utilizing Transport Layer Security (TLS) encryption of all data transmissions between Database 2 and Workstation 40. Other methods for encrypting Data 10 in transport may be used, either instead or together with TLS over HTTPS, for example, transmitting the Data 10 as encrypted by Encryption Tools 11. For added privacy protection and data security Workstation 40, Internet Gateway 7, Server 3, and other devices within System 1, may be configured to prevent caching (e.g., temporarily writing or storing) Personal Information data to non-volatile storage (e.g., disk, ROM) and instead use only volatile computer memory (e.g., RAM) to transmit/display Personal Information.

Monitoring tools 20 may be utilized to monitor, log, and enable auditing of, access and communications between the Internet, Workstation 40, Server 3, Private Cloud 6, and/or Database 2. Monitoring tools 20 are known in the industry and may include cloud monitoring software or services that can collect and track metrics, collect and monitor log files, and set alarms (e.g., CloudWatch, MetricFire, Datadog, Dynatrace, Prometheus, Graphite, and others.). Monitoring tools 20 may also include logging tools (e.g., AWS VPC Flow Logs) that log, and provide audit trails, for connections to private cloud 6 that attempt to access, process, transmit, and/or store data 10, including Personal Information data. Monitoring tools 20 may also include private cloud monitoring services that monitor, identify, and log all accounts (e.g., user or application) that attempted to access private cloud 6, the source IP address that originated the access, and when those access attempts occurred. Monitoring tools 20 generate access logs for Server 3, Private Cloud 6, and access to Database 2, and store those logs for a period of time, preferably 60 months. Monitoring tools 20 preferably are within Private cloud 6, but may also be external to private cloud 6, as illustrated in FIG. 1.

To implement granular access to Private Cloud 6, Server 3, and Database 2, System 1 utilizes an identity and security management (IAM) service or system 21 that is configured to restrict user access and ensure that only users (both persons and applications) who are authorized are allowed to access certain data resources. IAM System 21 may identify, authenticate, and control access for individuals as well as hardware and applications that may need access to Database 2, servers 3, or specific data sets or subsets, such as Participant Data Set 300. For example, when a concierge-user is performing tasks through the GUI 43 (e.g., booking participant travel), an embodiment of the present invention may utilize the identity management system 21 to restrict GUI 43 from accessing and displaying Participant Data Set 300 for participants who the user is not authorized to view. In this situation, the GUI 43 will only receive and display Participant Data Set 300 for participants who are assigned to the concierge-user accessing GUI 43. In some embodiments, a plurality of IAM Systems 21 may be utilized, and each IAM 21 may have different aspects of authentication and controls, or each IAM 21 may serve different subsystems.

In a preferred embodiment, IAM System 21 is configured to restrict access to all Data 10 by user, and user access level (e.g., user role) so that each user is allowed to access only the portion of Data 10 that the user is assigned or authorized to access. Access to server 3 also may be restricted by user, and user access level. For example, a user may be required to log-in using a username and strong password, to be identified and authenticated by IAM System 21 and gain access to the portions of Data 10 or parts of the system that the user is authorized to access. Authentication may be handled internally, or by various existing platforms (e.g., Okta, OneLogin, Auth0, RSA SecurID, SecureAuth Oracle Access Management Suite). Embodiments of the present invention may also utilize multiple factor authentication in addition to username and password to increase data security.

Data 10 in Database 2 may comprise one or more Clinical Study Data Sets 100 containing data subsets and information related to a plurality of clinical studies. The terms data set and data subset generally are used interchangeably here, and should be understood broadly to include any set, collection, record or aggregation of data or information, in any form, created, received, or provided in relation to a Clinical Study 25 and can be of any size (including a single datum), and in any form, including, numbers, text, audio, video, images, documents, spreadsheets, and others.

Clinical Study Data Set 100 may comprise a plurality of data subsets about a Clinical Study 25, including Protocol Data 101, User/Coordinator Data 115, Study Visit Schedule 130, Clinical Site Data Set 200, Participant Data Set 300, and Trip Data Set 400. User/Coordinator Data 115 comprises information about users who are authorized to access the travel booking system, as well as user assignments to one or more travelers.

Protocol Data 101, for example illustrated in Study 98, Study Overview 46, comprise information that generally may be applicable to a study as a whole (e.g., the study protocol), and may include the study sponsor, Study ID, study name, study status, duration, start and end dates, drug or treatment information, study phase, medical or scientific area, appointment procedures 135 (e.g., drug or treatment administration, consultation, medical examination, MRI, CAT scan, PET scan, lab work, infusion, LP, surgery, PK sample collection, radiology, ultrasound), types of participants (e.g., gender, age, medical condition, environmental exposure, nationality, region, and others), and other relevant information.

Study Visit Schedule 130 is a data set comprising data about a clinical participant clinical study visit, also referred to as an appointment, during which a clinical participant may be examined or assessed as part of a Clinical Study 25. Data in Study Visit Schedule 130 may comprise a Visit ID, Visit Name, Visit Number, an Appointment Procedure 135, an Appointment Schedule 136, Visit Duration (e.g., associated with the Visit Name, Visit Number, and/or Appointment Procedure 135), and Exit Strategy. Appointment Procedure 135 may be associated with, or it may be based on, one or more of the Visit ID, Visit name, Visit number, visit tracks, and other Visit attributes. Appointment Schedule 136 may indicate a specific date for a visit, a range of dates (e.g., specific dates, predetermined date range, relative to a previous visit, or relative to the beginning or end of a study, or to another prior or later event or date). Appointment Schedule 136 may also indicate a "floating" Appointment Schedule 136 indicating that the visit (or appointment) can be scheduled at any available time. Appointment Schedule 136 may also comprise an appointment start date and time, an appointment end date and time, and/or appointment duration. Appointment Schedule 136 may also comprise an Arrive By Date and Time 137 and a Depart After Date and Time 138. Arrive By Date and Time 137 may be based on an appointment start date and time, the appointment procedure 135, and/or other factors, allowing a patient to settle mentally or physically prior to an appointment, to complete pre-appointment preparations, or to accommodate patients with medical or health issues. Depart After Date and Time 138 may be based on an appointment end date and time, the appointment procedure 135, and/or other factors, allowing a patient time after an Appointment procedure 135 for observation, calming, follow up, accommodation for health or medical issues, and others.

Study Visit Schedule 130 may also include information about an unscheduled visit that may be used for an unscheduled medical follow-up that may be discretionary or may be mandated after certain appointment procedures 135. Study Visit Schedule 130 may also include data about clinical study visit tracks (e.g., patients undergoing different schedule of assessment, or tracks, depending on various criteria), visit cycles (e.g., repeating one or more visits/appointments), visit "jumps" (depending on criteria, a patient may jump, e.g., out of a visit cycle; to a different visit track; to exit a study; to another visit, and others), visit notes, and other visit data attributes.

Visit ID may be an alphanumeric identifier for a visit in a Study Visit Schedule 130. For example, it may be an abbreviation reflecting one or more of a Visit Name, Visit Number, Visit Description, Appointment Procedure 135, and other visit data attributes. Visit Name may be a descriptive name for each visit. For example, in FDA approved clinical studies, Visit Name may be the name of the visit from the FDA approved study protocol.

Exit Strategy may describe how a patient has exited, or will exit, a study. For example, a study Visit Schedule may comprise multiple exit tracks that allow for participants to exit a study based on different visit schedules if participants are in different circumstances. For example, a participant who completes a visit schedule may have an End of Study (EOS) visit following which the participant may exit the study. Other patients may exit one study and enter another, such as a long-term extension or open label extension study. A patient may also exit a study for various other reasons (e.g., by choice, adverse effects, illness, death). An Exit strategy may be configured depending on the method of exit (e.g., rollover, adverse event, others) to move the patient to one of several exit tracks, which may have different visit schedules associated with them. In an example, early exit due to an adverse event may require an exit track with numerous safety follow-up visits, whereas a patient who completes the entire visit schedule may just attend an End of Study Visit.

Study Travel Policy 150 may comprise data about rules, options, restrictions, and policies applicable to travel by participants in a Clinical Study 25. For example, Study Travel Policy 150 may comprise data establishing reimbursement, such as, whether various travel related expenses (e.g., meals, tolls, parking, prescriptions, phone calls, and others) are reimbursable, whether approval is required for reimbursement, and maximum reimbursable cost. Study Travel Policy 150 may also comprise data indicating whether various types of transportation or lodging are bookable and/or reimbursable, for example Air Travel/Flights, Car Rental, Car Service, Ferries, Ambulances, Rail, Buses, Hotels, Long Term Lodging, and others. Study Travel Policy 150 may also establish maximum costs that are reimbursable or bookable for the various types of transportation and/or lodging. The following table provides some limited and by no means exhaustive examples of expense items and services and an associated policy rule that may be part of the data in a Main Study Travel Policy 151 and in a Specialized Travel Policy 152:

| Sample Item Types | Sample Policy |
|---|---|
| Reimbursement | Enabled |
| Travel Booking | Enabled |
| Travel Companions | Up to USD per trip |
| Ambulances | Bookable with approval |
| Buses | Bookable, Reimbursable, Max USD/person/visit |
| Car Service | Bookable, Not reimbursable, Max USD |
| Flights | Bookable, Reimbursable, Max USD person/visit |
| Hotels | Bookable, Reimbursable, Max USD/night |
| Long-Term Housing | Bookable with approval, Reimbursable with approval, Max USD/month |
| Rail | Bookable, Reimbursable, Max USD/person/visit |
| Rental Car | Bookable with approval, Reimbursable with approval |
| Stipends | Full-day/Half-day Clinic, Home, Remote |
| Meals | Reimbursable, Max USD/meal |
| Mileage | Reimbursable, At standard rate |
| Parking | Reimbursable |
| Tolls | Reimbursable |
| Overall Limit | No overall limit |
| Childcare | Not reimbursable |
| Entertainment | Not reimbursable |
| Extra Baggage | Not reimbursable |
| Internet | Not reimbursable |
| Other | Reimbursable with approval |
| Phone Calls | Not reimbursable |
| Prescriptions | Not reimbursable |
| Rideshare & Taxi | Reimbursable |
| Insurance | Not prepayable |
| Interpreters | Not prepayable |
| Traveling Nurses | Not prepayable |
| Visas/Passports | Prepayable with approval |

Study Travel Policy 150 may also comprise a main travel policy 151 and a Specialized Travel Policy 152. Main travel policy 151 may apply by default to all portions of a participant's 26 travel for a Clinical Study 25, including reimbursements, transportation, lodging, and others, unless a specialized travel policy 152 applies to one or more of those travel portions.

A Specialized Travel Policy 152 may establish rules and restriction different from the main travel policy 151, for example, different reimbursement amounts for some travel related services, different allowable cost for booking certain types of transportation types (e.g., higher cost for flights, or car services) or lodging (e.g., higher or lower ranked hotels, different cost limits for hotels or long-term lodging), may allow booking of certain transportation (allow booking of, e.g., car service, limousine, ambulance, which otherwise may not be allowed) or lodging (e.g., permit long term housing not otherwise permitted). For example, a Specialized Travel Policy 152 may be a Visit Travel Policy 153, Site Travel Policy 154, Custom Travel Policy 155, a Country Travel Policy 156, and combinations thereof.

A Country Travel Policy 156 may apply based on a participant's country. A Site Travel Policy 154 may be based on a particular clinical site and will apply for travel of a participant associated with the clinical site. A Visit Travel Policy 153 is a Specialized Travel Policy 152 based on a visit (e.g., visit ID, visit type, visit name) and/or on a Visit Policy Label 131, from Study Visit Schedule 130. A Visit Policy Label 131 may be associated with a particular type of visit or appointment (e.g., "Surgery"), with a range of visits or appointments, or with individual visits or appointments and a Visit Travel Policy 153 may apply to all participant travel associated with such visits or appointments. A Custom Travel Policy 155 may be based on a Traveler Policy Label 321 associated with one or more participants. For example, a Traveler Policy Label 321 may be a "1st class" label, and a Custom Travel Policy 155 associated with a "1st class" label may allow booking of first-class air travel, even if the main Travel Policy 151 allows only economy air travel. Similarly, Travel Policy Label 321 indicating "Long-Term Housing" will permit booking of long-term housing where the Main Travel Policy 151 does not allow long-term housing. A Specialized Travel Policy 152 may also be based on various other factors (e.g., appointment location, institution, visit city or town, participant age, and others), as well as additional policy labels that may be associated with a participant, trip, site, country, institution, or other circumstances.

A Specialized Travel Policy 152 may combine one or more of a Visit Travel Policy 153, Site Travel Policy 154, Custom Travel Policy 155, and a Country Travel Policy 156, and will apply if all of the combined travel policies apply. For example, a Specialized Travel Policy 152 combining a Visit Travel Policy 153 associated with a "Long-Term Stay" Visit Policy Label 131 for a "Surgery" visit, and a Country Travel Policy 156 applicable to USA participants, will permit long-term hotel lodging for a USA participant traveling for a "Surgery" visit (and is therefore associated with the "Long-Term Stay" Visit Policy Label 131), but will not permit long-term hotel (if prohibited by the main policy) for USA participants who are not associated with the "Long-Term Stay" Visit Policy Label 131. A Specialized Travel Policy 152 that is a combination of all of Visit Travel Policy 153, Site Travel Policy 154, Custom Travel Policy 155, and a Country Travel Policy 156 will only apply to participant travel associated with all required conditions for each of the combined travel policies, such as an appropriate Visit Policy Label 131, Traveler Policy Label 321, Participant Assigned Site 303, and participant country.

Clinical Site Data Set 200 comprises information about a clinical site associated with a Clinical Study 25. A clinical site is a location where clinical study participants are assessed, evaluated, and/or examined through Appointment Procedures 135, such as testing of medical procedures, treatments, medications and drugs, medical devices, and other therapies. During a visit to a clinical site a participant may undergo an assessment through an appointment procedure 135 performed at the site. Alternatively, an appointment procedure 135 may be performed at a patient's home (or other non-site location) and the clinical site will perform the assessment upon receiving data from the appointment procedure 135. Certain appointment procedures (e.g., assessments) may also be performed remotely, or virtually, using a mobile device, a portable analytical device, and similar equipment. Clinical site personnel may enroll participants in a study. A clinical site may have one or more locations (identified by, e.g., address, specific building, specific office or laboratory, and others), such as a site main location, and a Site Appointment Location 201 associated with an appointment procedure 135. A Site Appointment Location 201 may be the same or different from the clinical site's main location. A clinical site may perform all appointment procedures at a single Site Appointment Location 201, or a clinical site may have a Site Appointment Location 201 associated with one or more appointment procedures (e.g., where one or more types of appointment procedures, such as MRI and/or Cat Scans, may be performed), and another Site Appointment Location 201 associated with other appointment procedures, for example, medical observation and lab tests. Clinical Site Data Set 200 may comprise a site identifier, site name, and Site contact information 202. Site contact information 202 contains information about who to contact (e.g., names, titles, departments, automated systems, etc.), whether the contact is to receive an itinerary, and methods of contacting the clinical site, including telephone numbers, emails addresses, facsimile, online access portals, API interfaces, and others.

Figure 3:
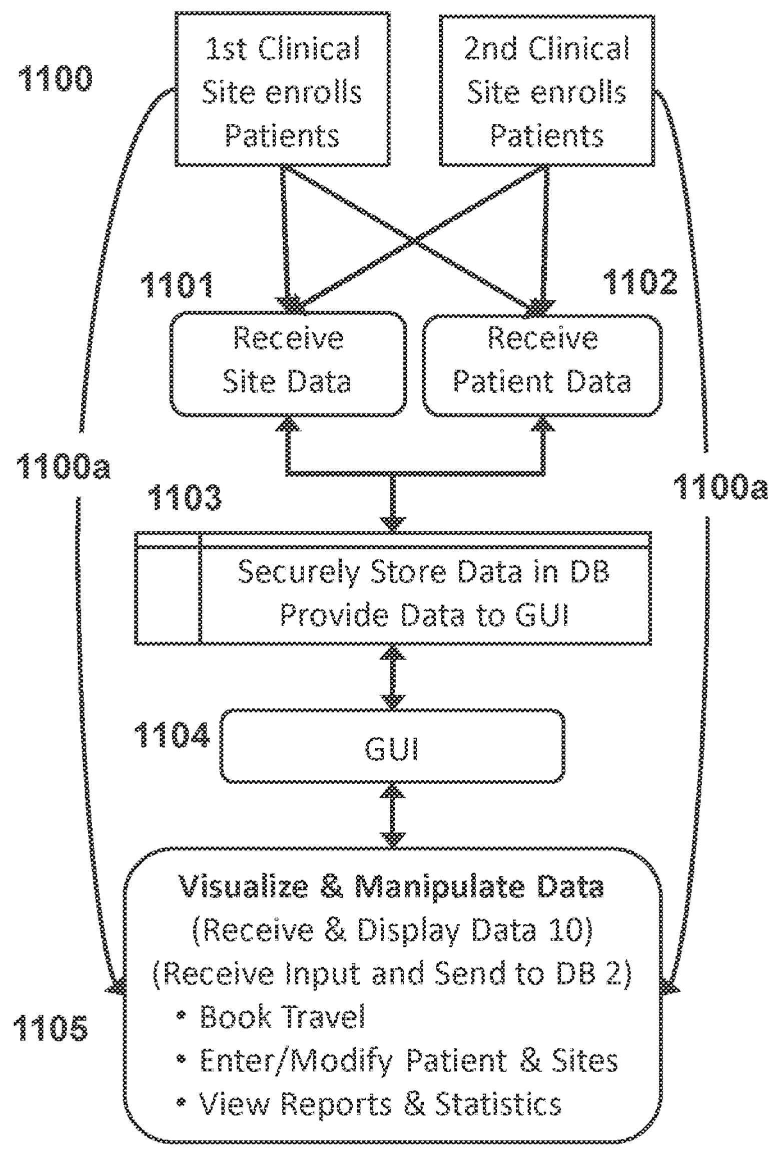
FIG. 3 is a diagram illustrating a flowchart of an embodiment of the present invention.

Clinical Site Data Set 200 may be provided by a clinical site and received by and stored into Database 2 through the Study Sites Interface 60 of GUI 43, as illustrated by numeral 1100*a* in the embodiment of FIG. 3. Clinical Site Data Set 200 may also be imported in the form of a data file (e.g., CSV, etc.), or it may be transmitted electronically over a network using secure transfer protocols (e.g., FTPS, UDP, etc.) exemplified by numeral 1101.

Participant Data Set 300, comprises data about a participant in a Clinical Study 25, including Participant Study Information 301, Participant Personal Data 307, Traveler Profile 309 data, and other data.

Participant Data Set 300 may be received in Database 2 using various techniques and methods, an example of which is illustrated in FIG. 3. In step 1100 clinical sites enrolls patients 26 into a clinical study 25. Users of an embodiment of system 1 may receive Participant Data Set 300 from the clinical sites in step 1105, as indicated by numerals 1100*a*. Participant Data Set 300 may be received in step 1102 in hardcopy or electronically as illustrated in FIG. 3, numeral 1100*a*. In step 1105, users may input Participant Data Set 300 through Participant Interface 52 of GUI 43 utilizing input device 41. If Participant Data set 300 is provided in hardcopy, users may need to manually enter the data, or the hardcopy data may be converted to digital text (e.g., scanned, OCR, etc.) and imported into GUI 43. Users may also import Participant Data Set 300 provided in an electronic format (e.g., spreadsheet, text file, and others). In step GUI 43 may transmit Participant Data set 300 to be securely stored in Database 2 in step 1103. Participant Data Set 300 may also bypass GUI 43 and a user by being transmitted electronically from the clinical site or another entity using well known secure data transmission techniques (e.g., API calls, FTP, UDP, secure file transfer protocols, etc.) as illustrated by step 1102, and then stored in Database 2 in step 1103. A user may further add additional Participant Data 300 through GUI 43, in a participant "onboarding" process by obtaining and inputting additional participant information to supplement, customize, or individualize various portions of Participant Data Set 300. The onboarding process may include phone calls, electronic assistance request forms, and other methods to obtain information from participants or other relevant sources. A request to access a secure electronic assistance request form may be transmitted to clinical site personnel, participants, caretakers, and other parties with relevant information and will allow them to securely input the information in Participant Data Set 300.

Figure 2:
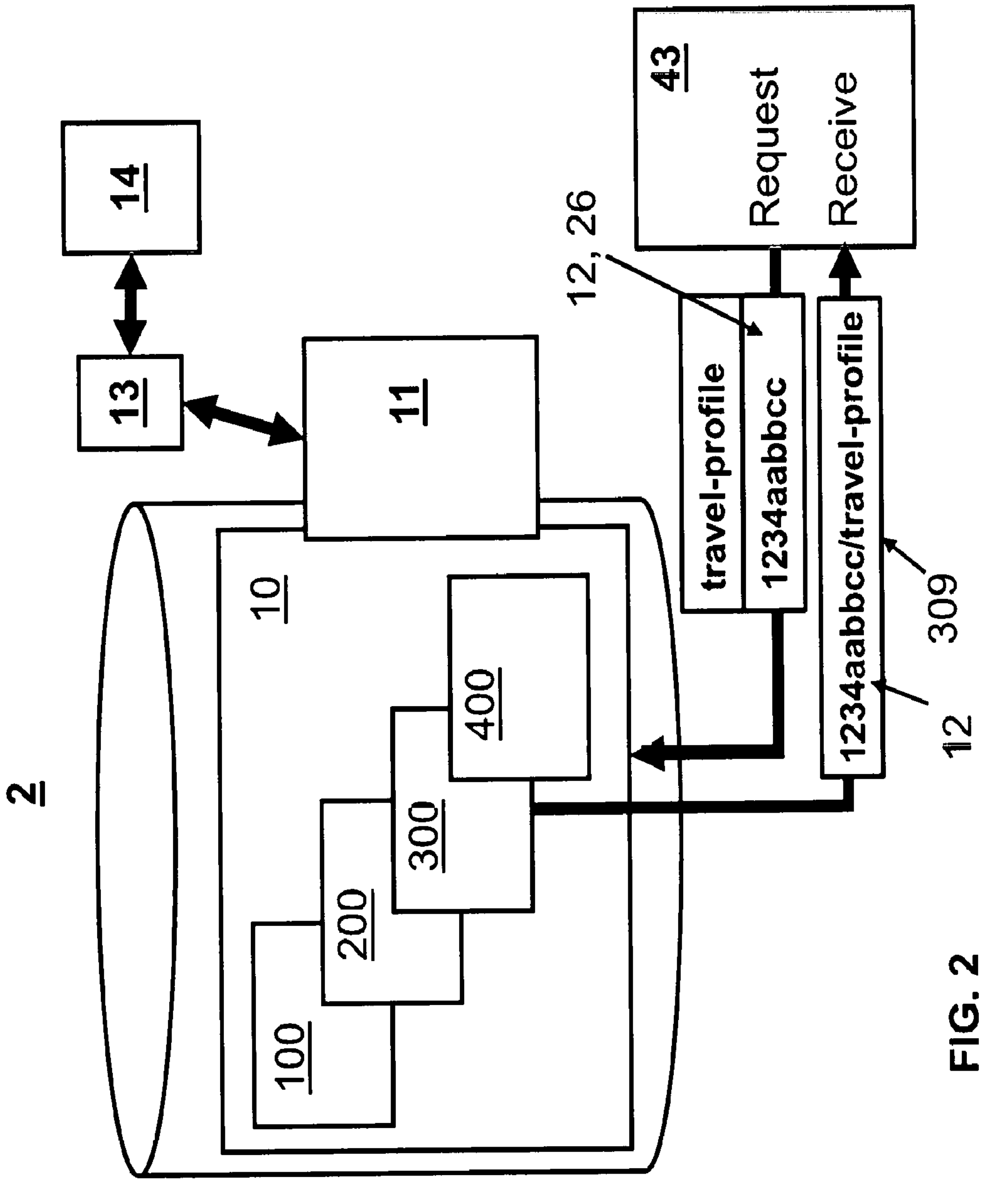
FIG. 2 is a diagram illustrating a database embodiment in an embodiment of the present invention.

For the privacy and security of the Participant Data Set 300, it may be stored encrypted in Database 2. In addition, one or more unique identifiers 12 may be associated with different data or data records of Participant Data Set 300 and utilized to pseudonymize Participant Data Set 300 and enhance security of Personal Information data. For example, Participant Data Set 300, or any portion of it may be associated with a unique identifier 12 so that it can only be accessed by utilizing unique identifier 12, instead of utilizing data that may identify an individual as a participant (e.g., name, gender, address, birthday, and others). FIG. 2 illustrates an example in which GUI 43 requests (arrow labeled as "Request") from database 2 travel profile data set 309 for a participant 26 with a unique identifier "1234aabbcc." GUI 43 will receive (arrow labeled as "Receive") from database 2 a record containing Travel Profile 309 corresponding to the requested unique identifier 12.

Figure 37:
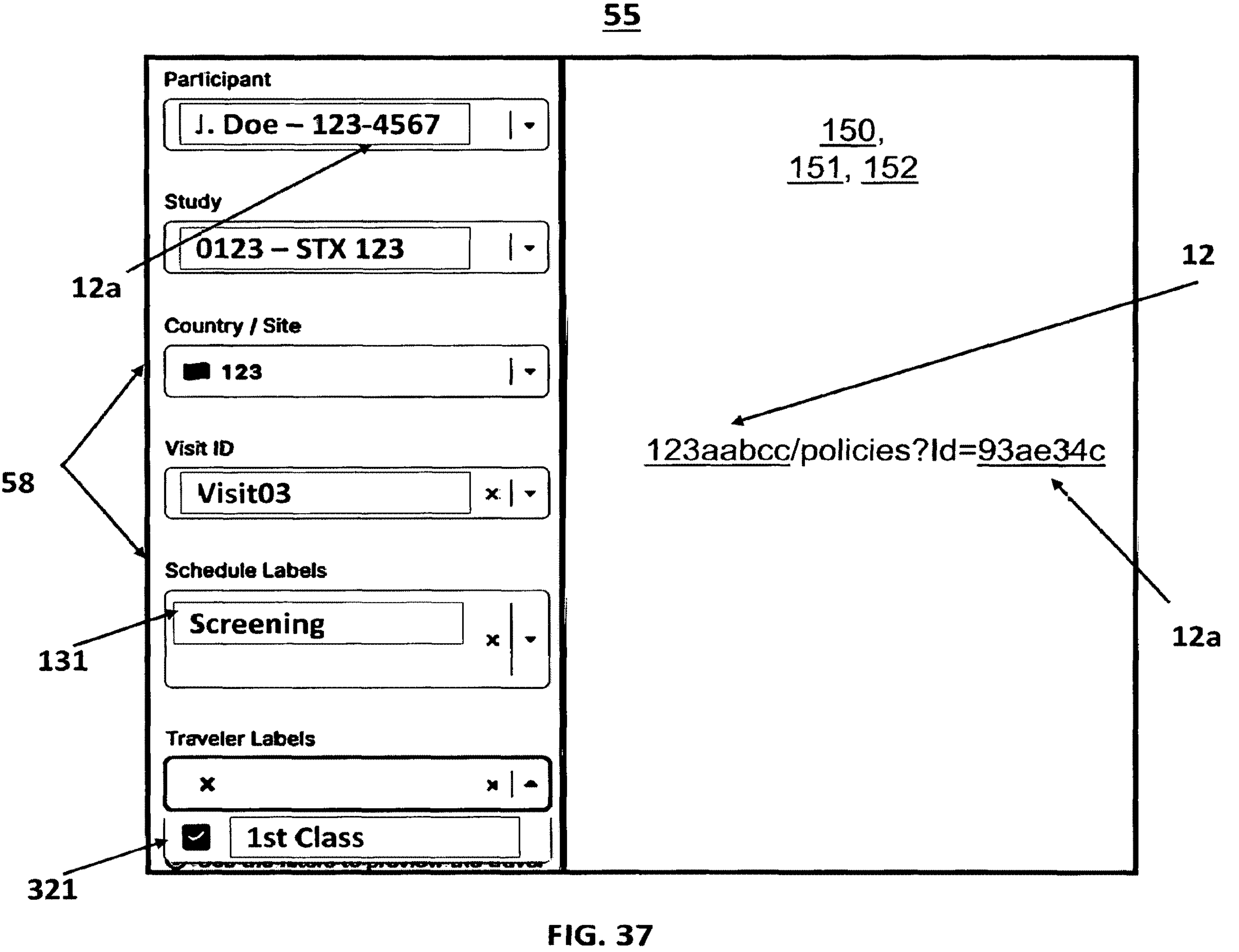
FIG. 37 is a diagram of an embodiment of a clinical study participant travel policies graphical user interface in an embodiment of the present invention.
Figure 38:
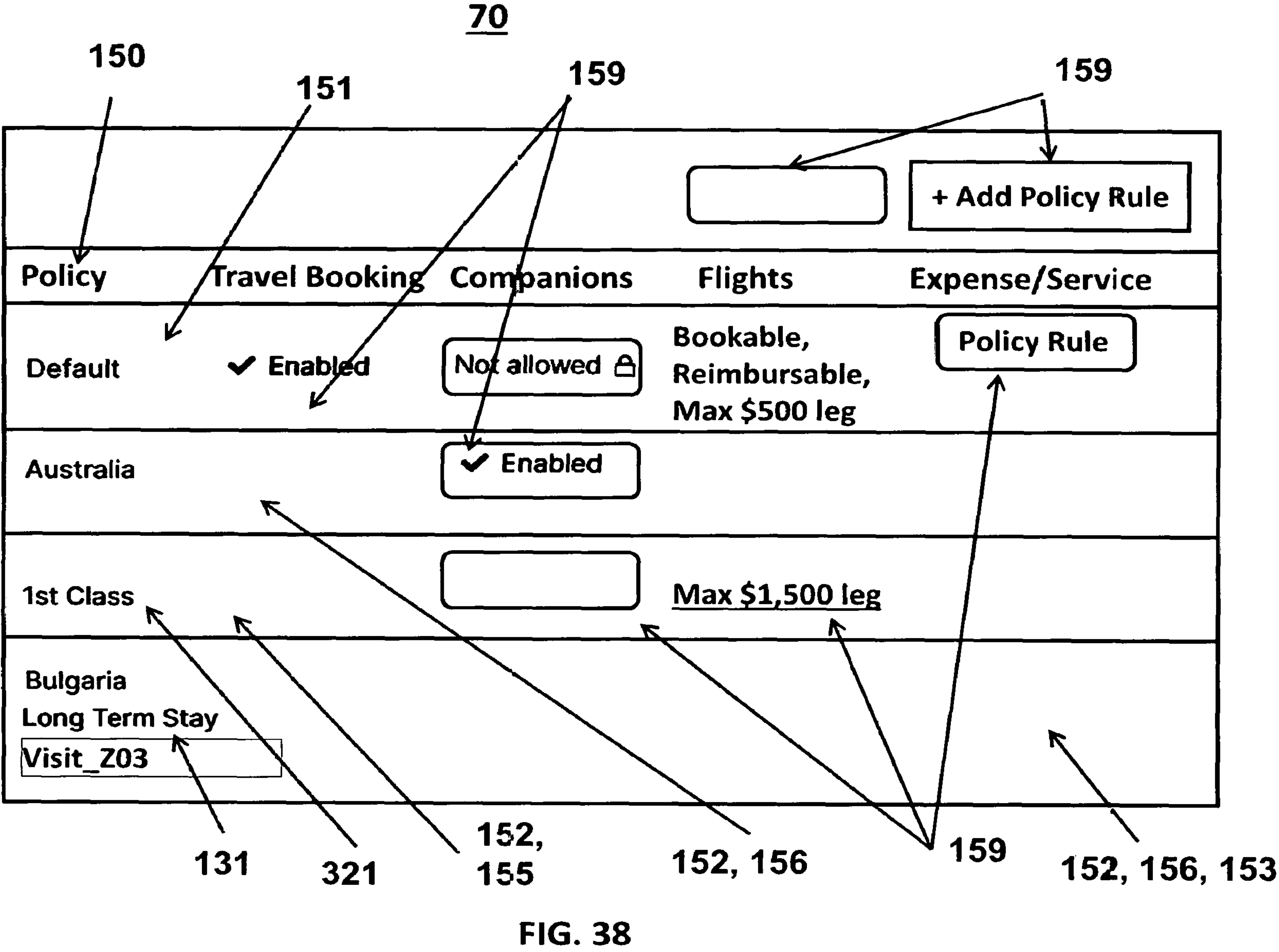
FIG. 38 is a diagram of an embodiment of a clinical study travel policies graphical user interface in an embodiment of the present invention.
Figure 39:
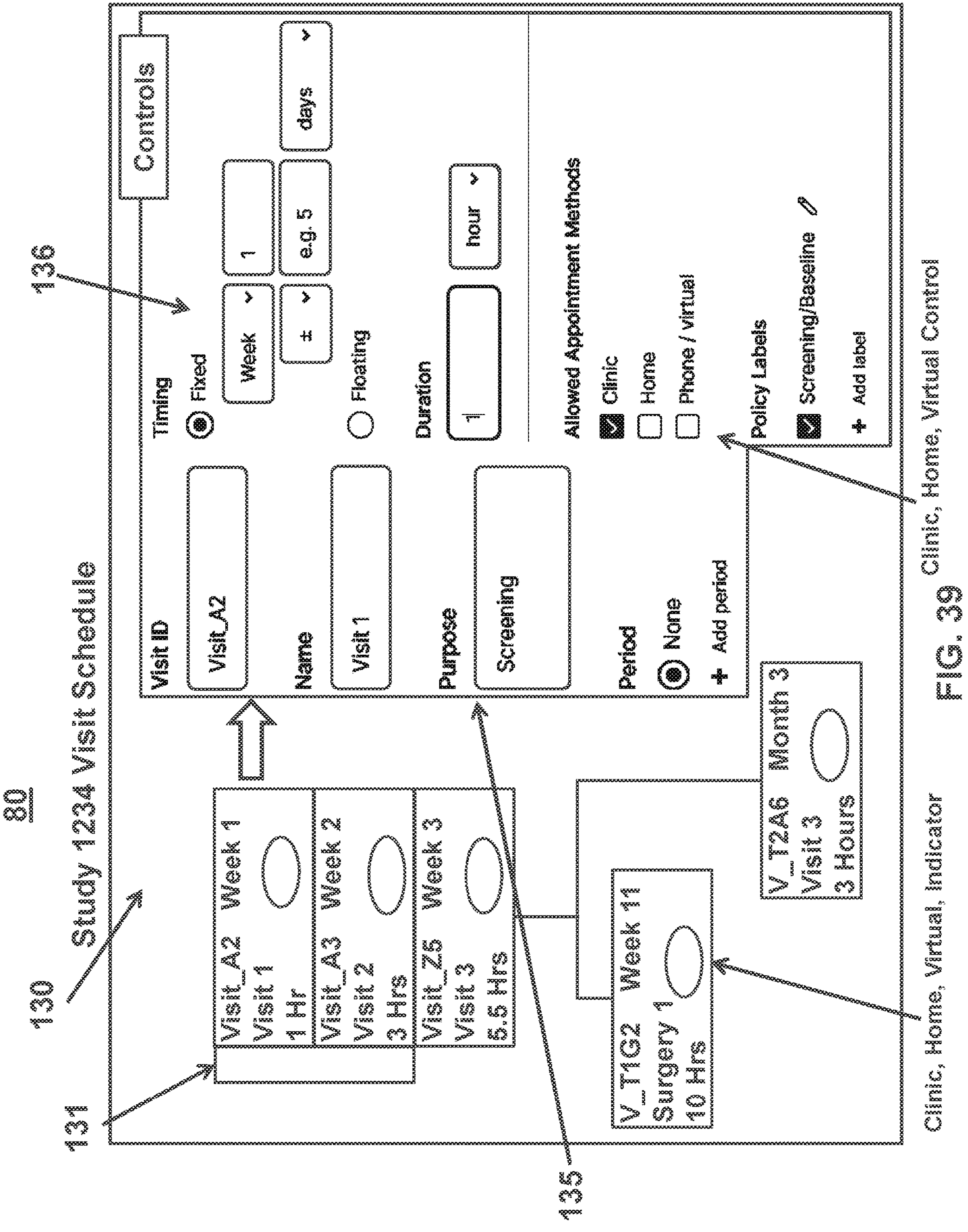
FIG. 39 is a diagram of an embodiment of a clinical study visit schedule graphical user interface in an embodiment of the present invention.
Figure 40:
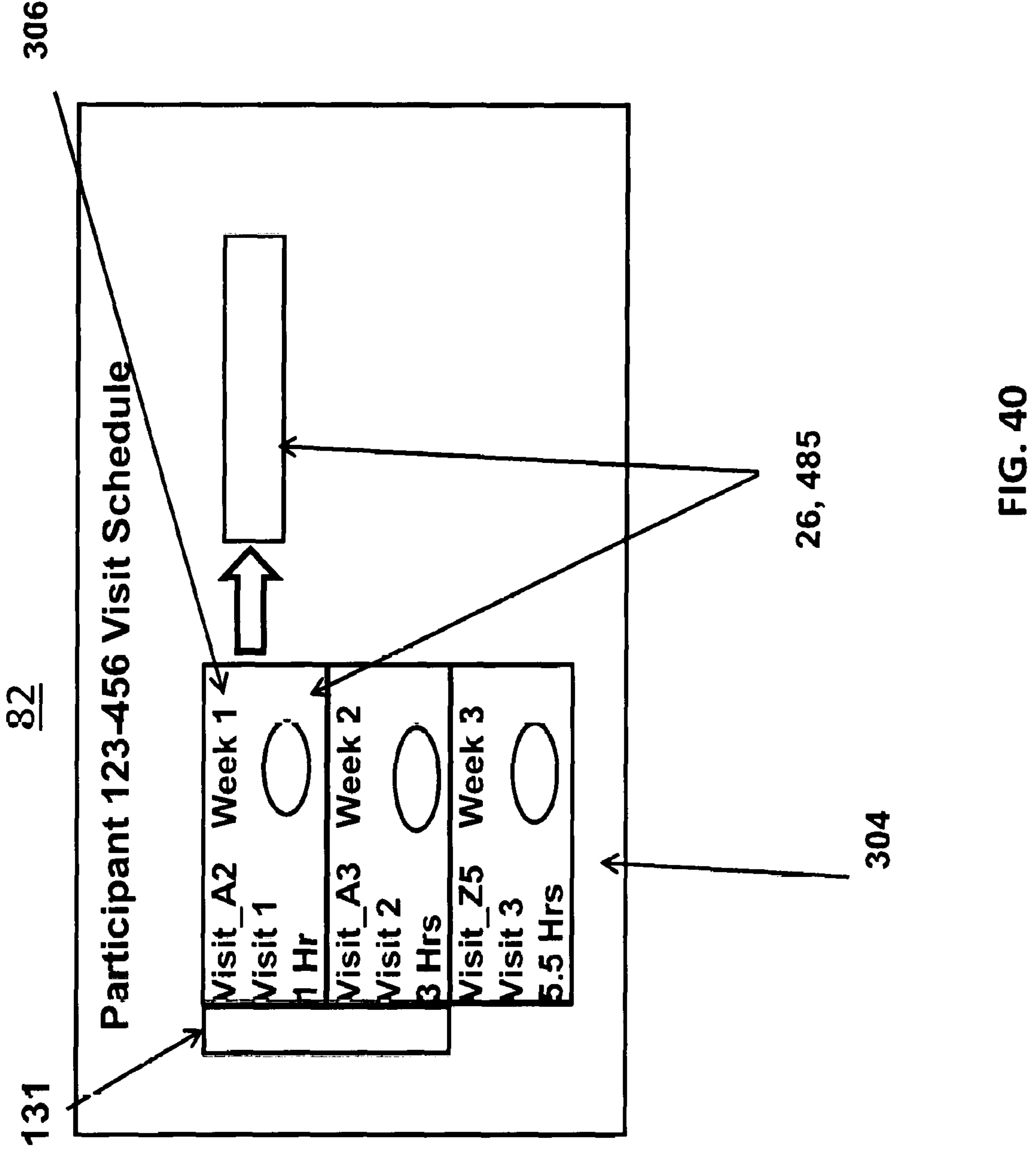
FIG. 40 is a diagram of an embodiment of a clinical study participant visit schedule graphical user interface in an embodiment of the present invention.
Figure 41:
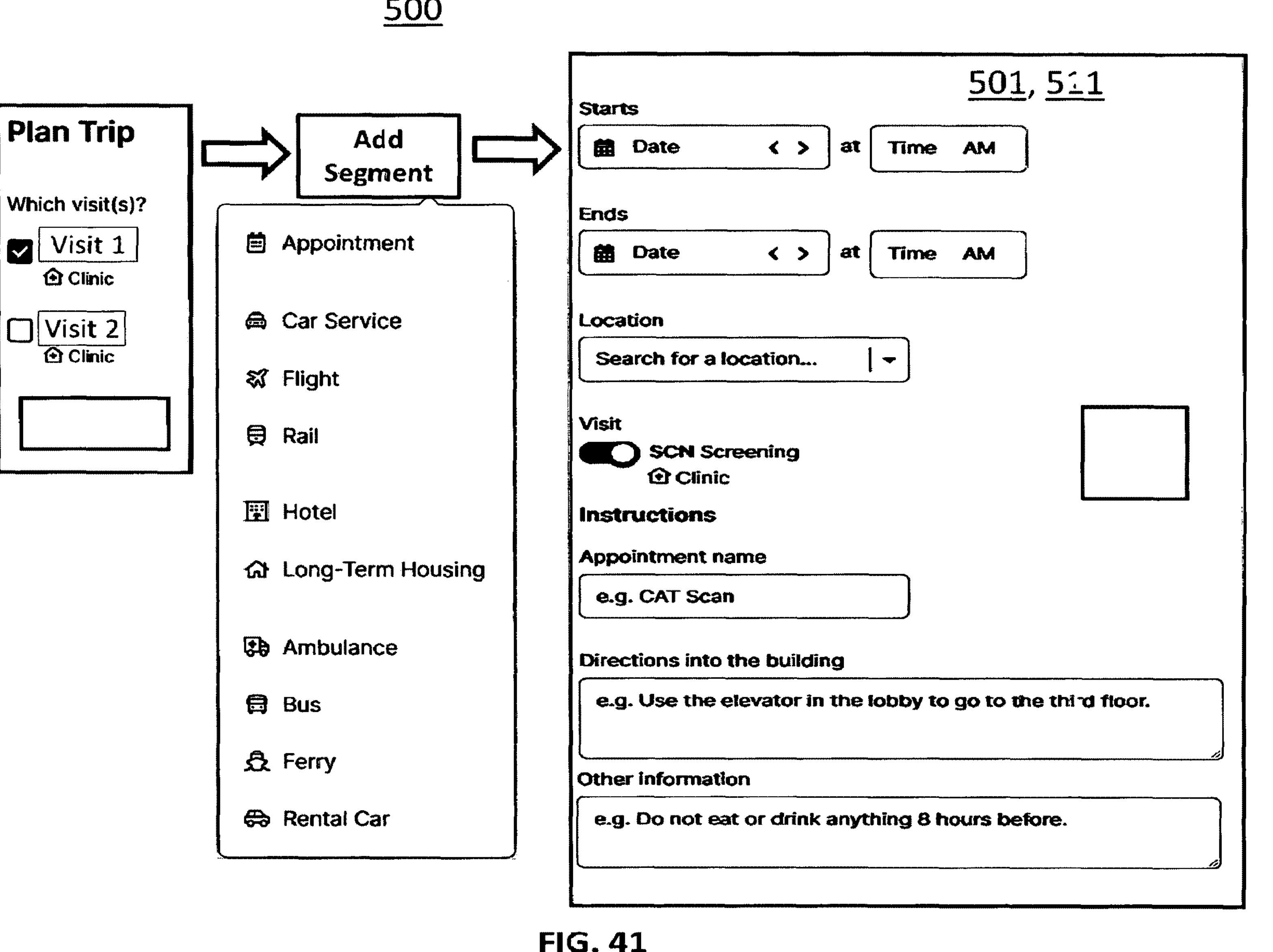
FIG. 41 is a diagram of an embodiment of a travel planning graphical user interface in an embodiment of the present invention.

Participant Study Information 301 comprises Participant Study ID 302 that references a participant 26 in a clinical study 25 without revealing participant name or other participant Personal Information. Participant Study ID 302 preferably is a unique code associated with a participant, and may consist of a Clinical Site ID for Participant Assigned Site 303, and an additional alphanumeric sequence. Participant ID 302 may be displayed in GUI 43 or provided in various documentation and may be utilized by parties associated with a study to view study information without revealing a participant's name or other Personal Information. If, pursuant to Privacy Laws, a participant invokes a right to forget Personal Information, Participant ID 302 may be utilized to identify and purge the appropriate Personal Information data from Participant Data Set 300. Participant Study Information 301 may also comprise an Enrollment Date, Participant Consent Record 330, Participant Assigned Site 303, Participant Visit Data 304, Participant Country 305, and applicable Individual Traveler Policies 320. Participant ID 301 may be associated with a unique identifier 12 corresponding to participant 26. Participant ID 302 may also be associated with another unique identifier 12 for participant 26, for example enrollment id 12*a* that identifies participant 26 as a participant in clinical study 25. As an example, FIG. 37 illustrates GUI 43 receiving from Database 2 into Participant Policies Module 55 a Study Travel Policy 150 associated with a participant 26 whose Participant ID 301 is 123-4576, unique identifier 12 is "123aabcc", and enrollment id 12*a* is "93ae34c." In some embodiments, Participant ID 301 may be an enrollment ID 12*a*.

Participant Consent Record 330 may contain information about a participant's informed consent related to access, use and/or processing of Personal Information for various purposes related to a Clinical Study 25, for example for travel booking, medical assessments, and other purposes. Participant Consent Record 330 may comprise data indicators (e.g., in the form of binary flags, such as "0" or "1", "true" or "false") that a participant has provided informed data consent in the form of a Consent Provided Indicator 3301, or that a participant has withheld, or not yet provided, informed data consent in the form of Consent Not Provided Indicator 3300. Consent Provided Indicator 3301 and Consent Not Provided Indicator 3300 may be multiple distinct indicators or may be a single binary (on/off, true/false) indicator. Furthermore, a system according to an embodiment may interpret the lack of an affirmative Consent Provided Indicator 3301 as a Consent Not Provided Indicator 3300. Participant Consent Record 330 is required for all participants (including their companions or caretakers whose personal information may be needed for the provision of travel or other services). Participants must sign a consent to process personal data (including health data), which may vary depending on the applicable jurisdiction (e.g., US, GDPR and non-GDPR countries, Australia, Russia, Turkey, Canada, and others).

Participant Consent Record 330, and Consent Provided Indicator 3301 or Consent Not Provided Indicator 3300 may be more granular and further comprise indicators of whether participant has provided consent regarding some "special" types of Personal Information data but not others, such as personally identifiable information (PII), personal data (e.g., PD under GDPR), protected health information (e.g., PHI under HIPAA, "Data concerning health" under the GDPR), and whether an electronic copy of an appropriate signed consent form is included in the Record 330. In a preferred embodiment of the present invention, appropriate Participant Consent Record 330, evidencing participant 26 consent for both personal information and for health records, as well as images of the appropriate executed consent forms are required for a Consent Provided Indicator 3301 to be present. In this embodiment, a Consent Provided Indicator 3301 for Participant 26 is required for the creation and storage of various participant 26 data, including Participant Personal Data 307, Traveler Profile 309, and others. A system according to such embodiment may be configured to prevent the creation or entry of Participant Data Set 300, or to initiate travel booking, for any participant or companion whose Participant Consent Record 330 comprises Consent Not Provided Indicator 3300, or lacks Consent Provided Indicator 3301. An embodiment of the present invention may generate an error message, create notifications, and/or prevent storing of any portion of a Participant Data set 300 that does not contain data in the Participant Consent Record 330.

Participant Consent Record 330 data, such as signed consent forms, may be received by and stored in Database 2 through Participant Consent Interface 57 of GUI 43 using input device 41, through transferring data using a portable storage device, or through direct data transmission into database 2 server or application server 3. Consent Provided Indicator 3301 and/or Consent Not Provided Indicator 3300 may be set automatically by the system based on the presence or absence of signed consent forms and other factors or may be manually set by a user. In an embodiment, a participant (or companion) may view and e-sign disclosure and consent forms for the processing of their personal information where such forms may be provided electronically in a similar manner as the assistance request form described above.

Participant Assigned Site 303 comprises information about a clinical site associated with a participant in a Clinical Study 25, for example a clinical site that assess participants and collect study information from a participant, either during a participant visit to the site, or from home procedures performed by a participant or another person such as a companion, family member or medical personnel. A participant may have more than one Participant Assigned Site 303 so that the participant may visit different sites and different times during a study.

Participant Visit Data 304 comprise the visit schedule applicable to a participant based on Study Visit Schedule 130 data, including information about at least one Appointment Procedure 135 and its associated Appointment Schedule 136 (e.g., start date/time, end date/time, duration, and other attributes). Participant Visit Data 304 may also comprise information about visits that have already occurred, and a Current Visit 306 (e.g., Visit Name, and/or Number of the next visit that needs to be scheduled). Participant Visit Data 304 may also associate a participant's trip with a Specialized Travel Policy 152 based on a Visit Policy Label 131 in Study Visit Schedule 130. For example, if a participant is traveling for a visit (e.g., an appointment) with a Visit ID or Visit Name associated with a Visit Policy Label 131 in Study Visit Schedule 130, portions of participant's trip (e.g., trip segments) may be subject to a Specialized Travel Policy 152 associated with the Visit Policy Label 131 if applicable.

Participant Visit Data 304 may also comprise a Traveler Policy Label 321 associated with a Custom Travel Policy 155.

Individual Traveler Policy 320 may comprise one or more Specialized Travel Policies 152, for example a Country Travel Policy 156 based on Participant Country 305, Site Travel Policy 154 based on Participant Assigned Site 303, visit travel policy 153 based on a Visit Policy Label 131, and others. Individual Traveler Policy 320 may also comprise a Custom Travel Policy 155 based on a Traveler Label 321.

Figure 27:
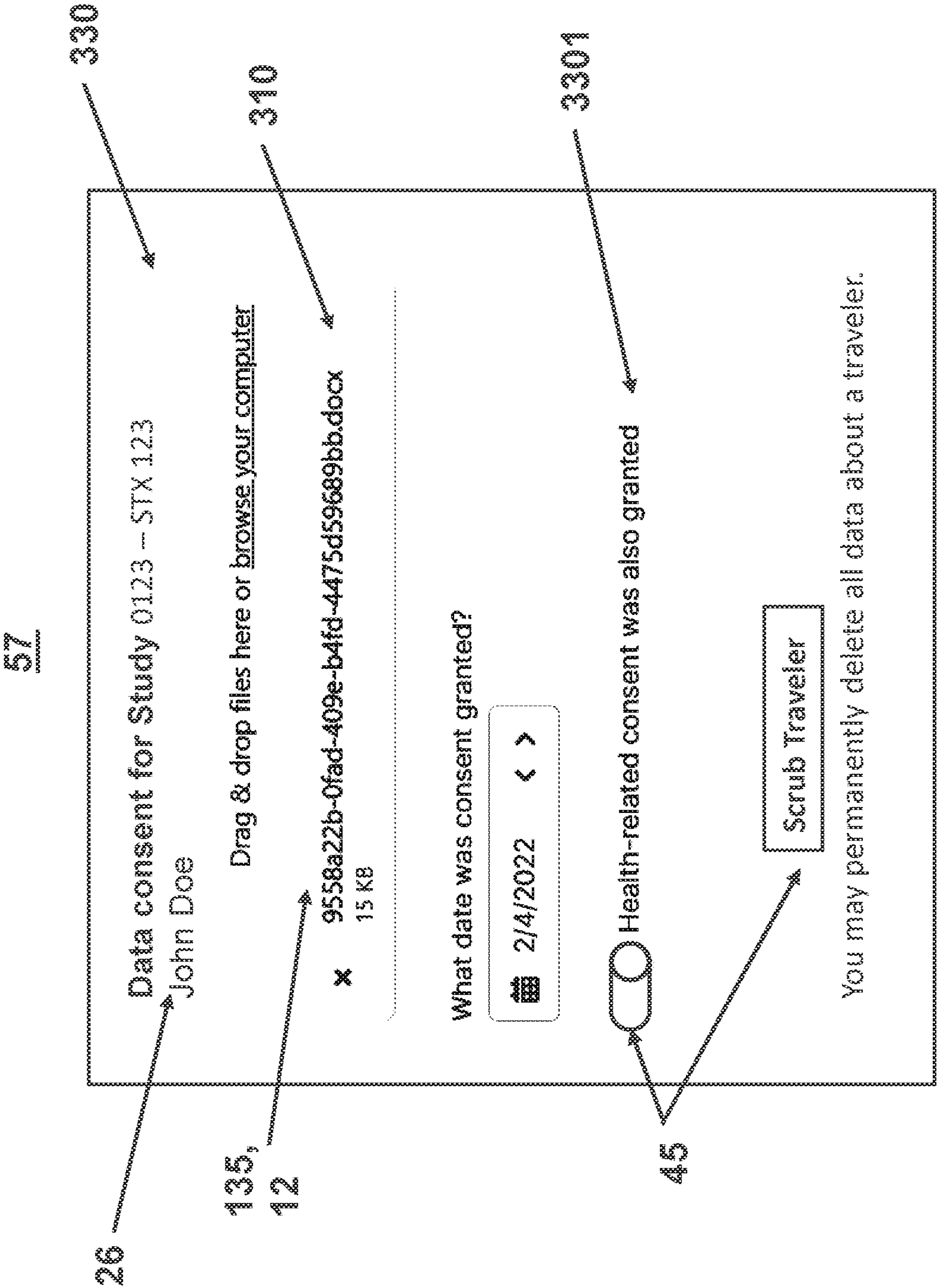
Figure 28:
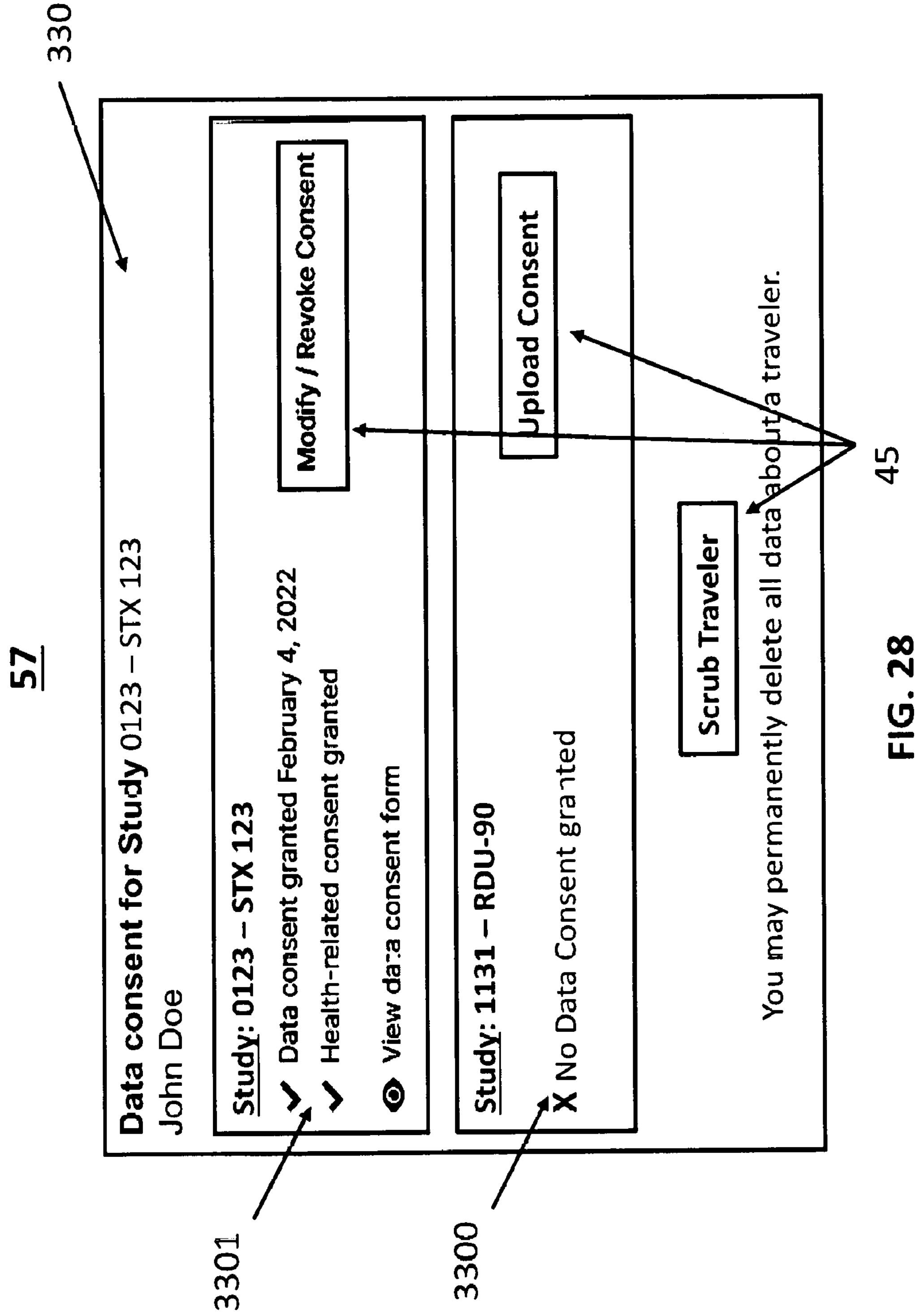
Figure 29:
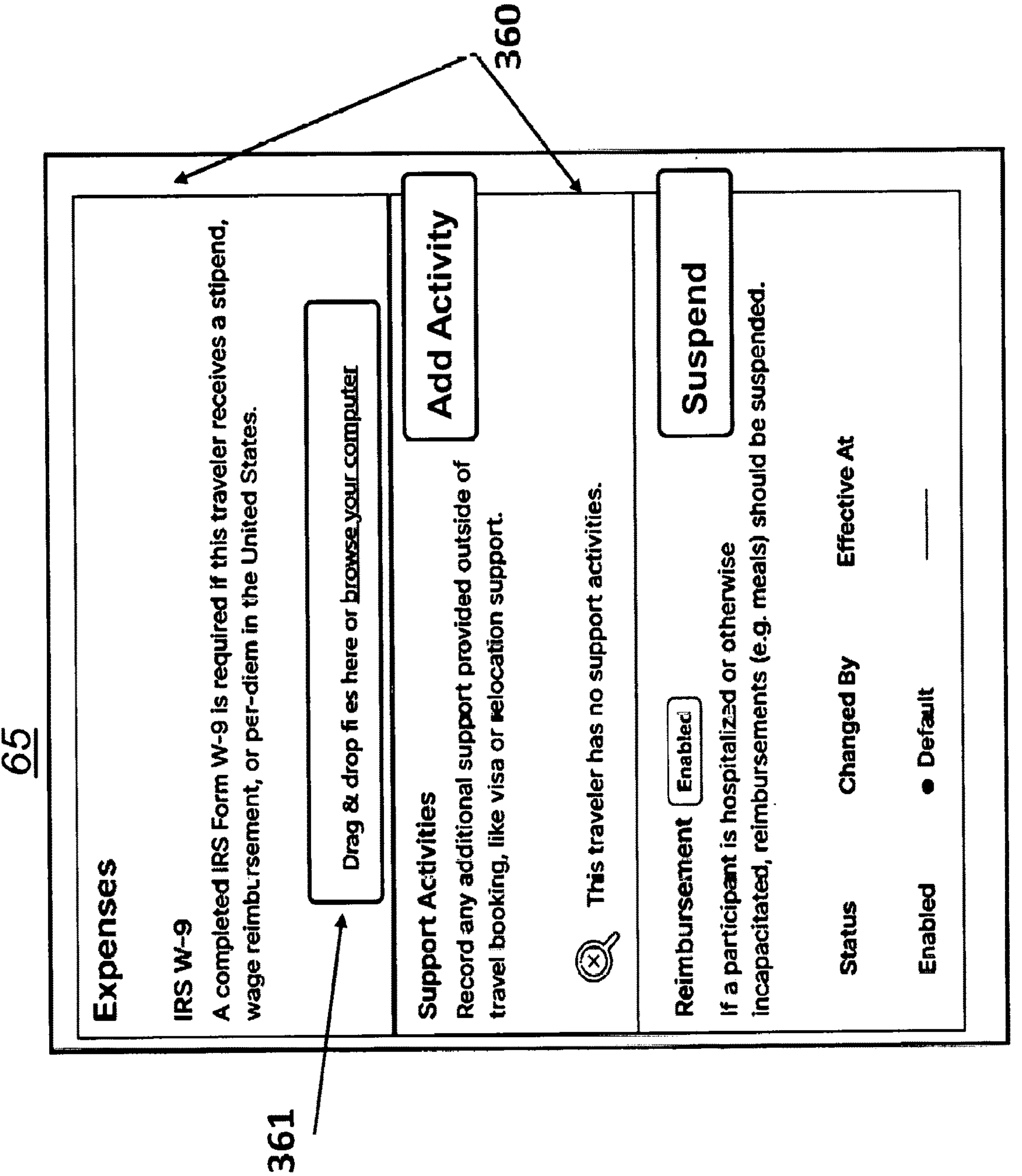
Figure 30:
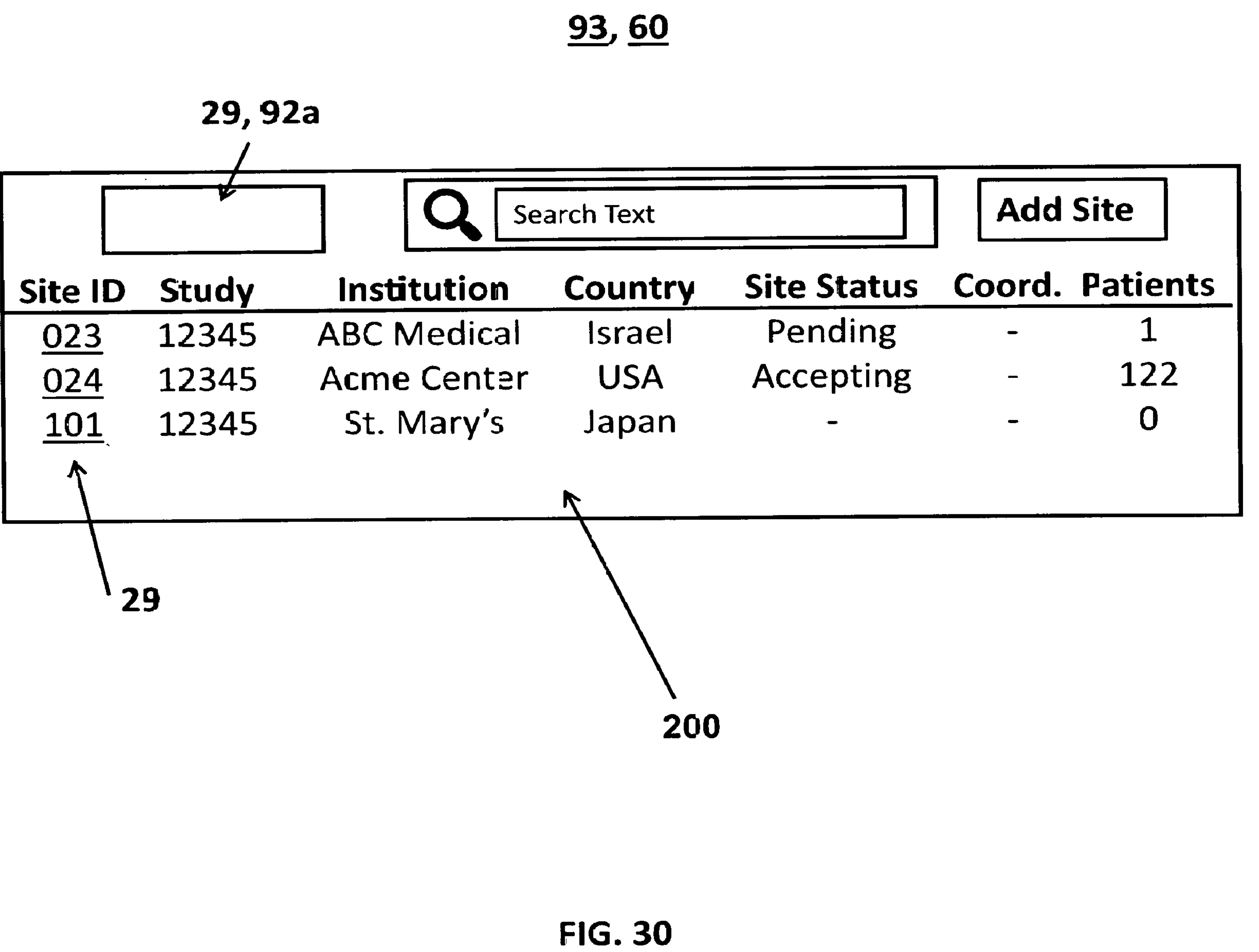
FIG. 30 is a diagram of an embodiment of a clinical study sites graphical user interface in an embodiment of the present invention.

Participant Personal Data 307 comprise identification and other information about a participant, such as name, sex, gender, birthdate, age, personal details, languages, Government issued Ids, known traveler numbers, and other information. Participant Personal Data 307 may include Participant Documents 310 in the form of uploaded electronic files (e.g., pdfs, images, QR Codes) containing information about and copies of passports, government Issued IDs, travel documents, medical cards, health forms, and others. To maintain security and data privacy, when electronic files with personal information are uploaded, preferably they are stored in heavily restricted logical storage locations (e.g., AWS S3 buckets, Azure Blob Storage) encrypted using encryption keys, and identifiable only via one or more pseudonyms, which may include a Participant ID, a unique identifier 12, and similar data security constructs. Preferably, all data 10, including files (e.g., like consent forms, passports, expense receipts) are stored into Database 2 and associated with an individual unique identifier 12, for example as illustrated in FIG. 27. In addition, each record of data 10 may also be associated with a unique identifier 12 of a participant 26, facilitating scrubbing of personal information.

Participant Personal Data 307 may further comprise Traveler Contact Information 308, preferably comprising accurate contact information about a participant, such as address location, phone number, email, primary contact (e.g., the participant, a companion, caretaker, or others), as well as contact instructions.

Traveler Profile 309 may comprise data about Traveler Origin Location 314, Traveler Identification 311, Traveler Health Restrictions 312, and Traveler Preferences 313.

Traveler Origin Location 314 may identify a street address for a participant, such as a home address, or another address or location (e.g., family home, hospital, facility, government building) that would be the preferred origin location for a participant's travel associated with a Clinical Study 25. Traveler Origin Location 314 also may comprise different Traveler Origin Locations 314 depending on the mode of transportation, for example, the participant's street address may be the Traveler Origin Location 314 for car service pick-up or drop-off, or the Traveler Origin Location 314 may be a preferred departure airport for Flights according to a Traveler Flight Preferences 341, Traveler Origin Location 314 may be a preferred bus terminal, train station, or port according to a Bus Preferences 342, a Rail Preferences 343, or a Ferry Preferences 344, respectively.

Identification 311 may comprise a travelers full legal name, contact information, Participant Documents 310, known traveler number, and other similar information that may be required, or desirable, to book a flight, check-in a hotel, reserve a car, or travel internationally.

Traveler health restrictions 312 comprises information about travel accommodations a traveler may need based on the traveler's health, medical conditions, and personal characteristics. For example, Traveler health restrictions 312 may comprise information about a traveler's Ability &

Assistance Requirements, if a traveler is blindness or has low vision, is deaf or hard of hearing, does not speak the local language, requires a wheelchair or another assistive device, has cognitive or developmental disabilities, requires animal assistance, and information. Traveler health restrictions 312 may also comprise information notes to assist the concierge-user while booking travel.

Traveler Preferences 313 may comprise information about a traveler's preferences or requirements associated with various types of travel and lodging. For example, Traveler Preferences 313 may include Flights Preferences 341, Hotel Preferences, Car Service Preferences 345, Car Rental Preferences 346, Bus Preferences 342, Rail Preferences 343, Ferry Preferences 344, Hotel Preferences 347, Long-Term Housing Preferences 348, and other Travel Preferences 313. Traveler Preferences 313 may also comprise information about ambulance use medical needs, for example, whether a traveler needs oxygen, requires tube feeding, has a colostomy bag, and others.

Flights Preferences 341 may comprise information such as a preferred departure airport, preferred airline, seat preference, known traveler numbers or other governmental security programs (e.g., TSA), frequent flyer programs. Flights Preferences 341 may also comprise additional information about the seating needs and preferences, for example, has peanut allergies, needs an extra seat to accommodate size, requires wheelchair assistance on and off the plane, carries own oxygen tank or requires oxygen, and any other ADA requirements or restrictions, as well as personal and other information about traveler's abilities, preferences, and luggage.

Bus Preferences 342 may comprise information such as a preferred departure bus station, preferred bus company, type or class of seating, whether a traveler requires boarding assistance, rewards programs, and other personal and health information about a travelers abilities. Rail Preferences 343 may comprise information such as a preferred departure train station, preferred railroad, type or class of seating, whether a traveler requires boarding assistance, rewards programs, and other personal and health information about a traveler's abilities. Ferry Preferences 344 may comprise information such as a preferred departure port, type of seating, whether a traveler is driving, whether a traveler requires assistance, rewards programs, and other personal and health information about a travelers abilities.

Car Service Preferences 345 and Car Rental Preferences may comprise information such as a preferred car service or rental company, loyalty information, type or size of vehicle, pick up or drop of location, whether a traveler has a wheelchair or other assistive device, whether a child safety seat is required, and other information about traveler's abilities and preferences.

Hotel Preferences 347 and Long-Term Housing Preferences 348 may comprise information such as a preferred lodging, hotel or chain, rewards and loyalty program, type and size of the room, preferred floor height, wheelchair accessibility, allergen free, and other available parking or garage, whether the hotel permits service or other animals, and any other ADA requirements or restrictions such as roll in shower.

Companion Data Set 325 may comprise information identifying travel companions for a participant who may be caregivers, parents, and others. Each travel companion for a participant will also have a Participant Data Set 300. If a travel companion is also a clinical study participant, Participant Data Set 300 for the travel companion will comprise the same types of information as for any other participant. If a travel companion is not a clinical study participant, Participant Data Set 300 will comprise only information necessary to allow travel booking.

Trip Data Set 400, comprises information about a trip by a traveler related to a Clinical Study 25. Trip Data Set 400 may comprise a Trip Origin 401, Trip Destination 402, Trip Schedule 403, Trip Segment Data 501, Itinerary 475 data, and booked travel data 450. Booked Travel Data 450 comprise Segment Booking Information 508 for booked, reserved or confirmed trip segments, and may also comprise Traveler Identification 311. Booked Travel Data 450 comprise data that may vary according to the type of a booked, reserved or confirmed trip segment. For example, a flight segment Booked Travel Data 450 may comprise ticket numbers, record locators, operating airline, flight numbers and schedule information, assigned seats, international travel requirements, luggage limitations, flight cost information, TSA warning and limitations, and other commonly known data associated with air travel. A hotel segment Booked Travel Data 450 may comprise hotel name and address, confirmation/reservation number, cost, room size and type, hotel amenities, rules and policies, and other similar hotel reservation information. An appointment Segment Booked Travel Data 450 may comprise confirmation of an appointment (or visit), the appointment schedule 136, Appointment procedure 135, instructions about how to access the Appointment Location or how to prepare for an appointment, and other relevant information.

Figure 31:
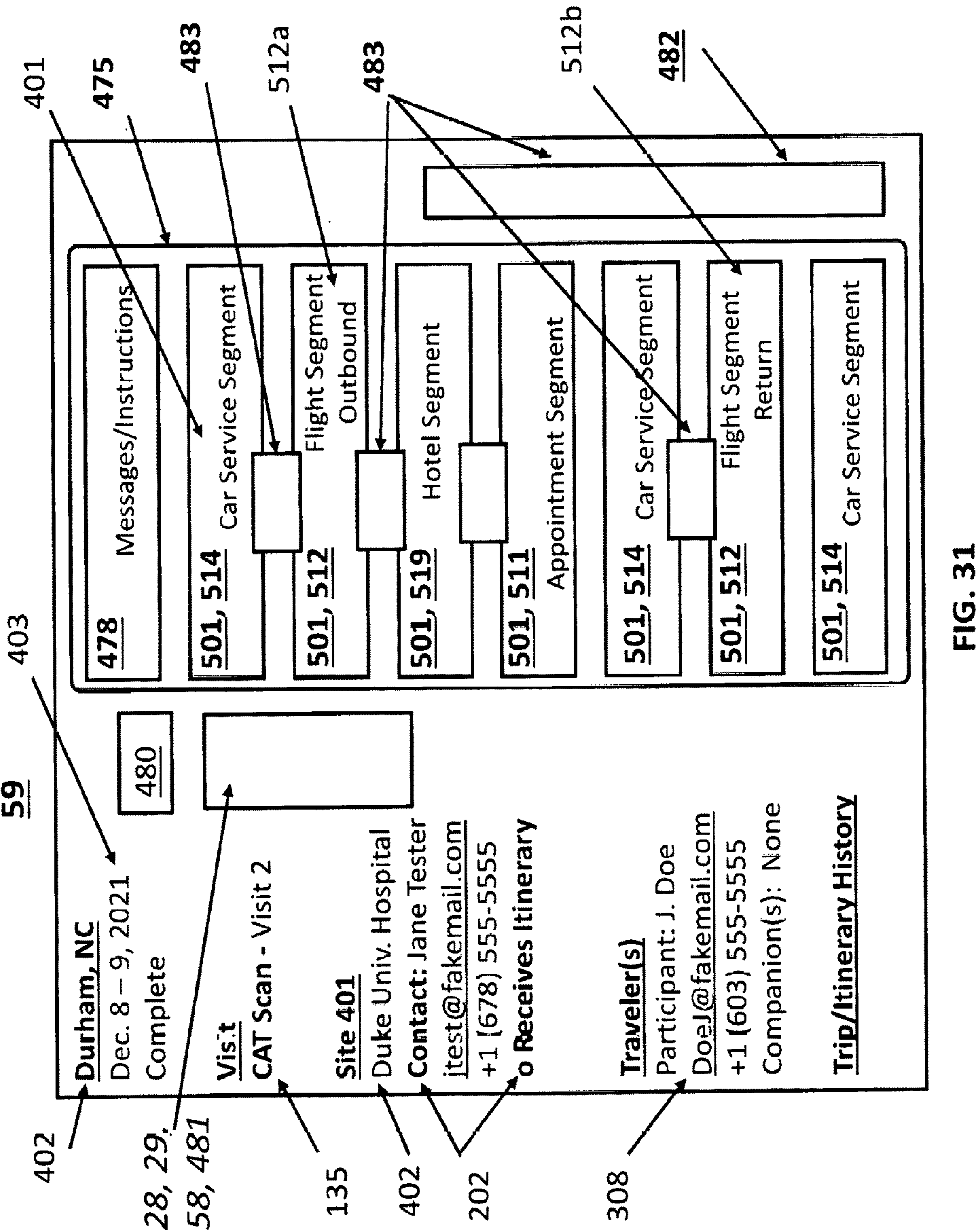
FIG. 31 is a diagram of an embodiment of a clinical study participant travel graphical user interface in an embodiment of the present invention.
Figure 32:
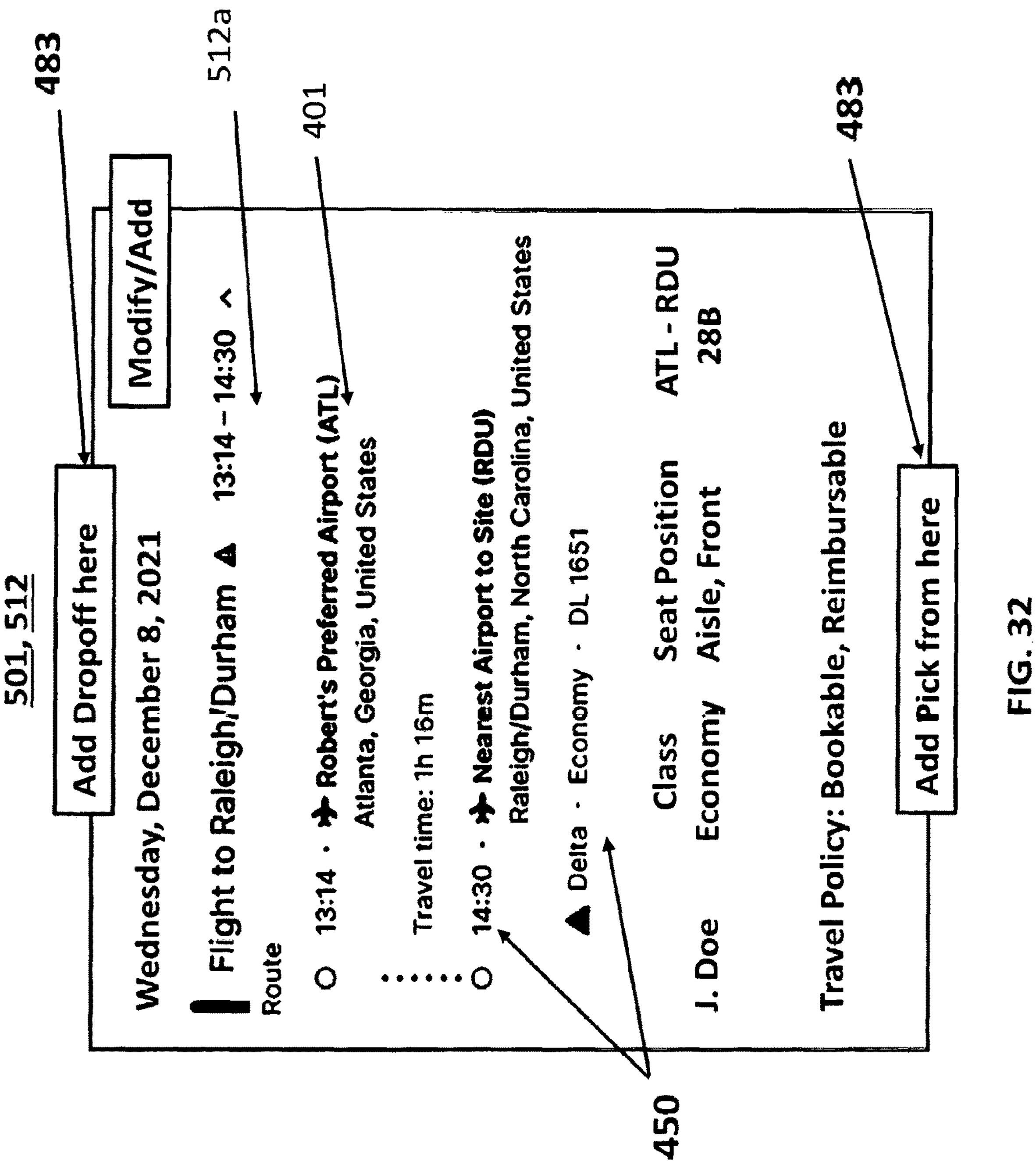
FIG. 32-36 are diagrams of embodiments of clinical study participant travel graphical user interface in an embodiment of the present invention.
Figure 33:
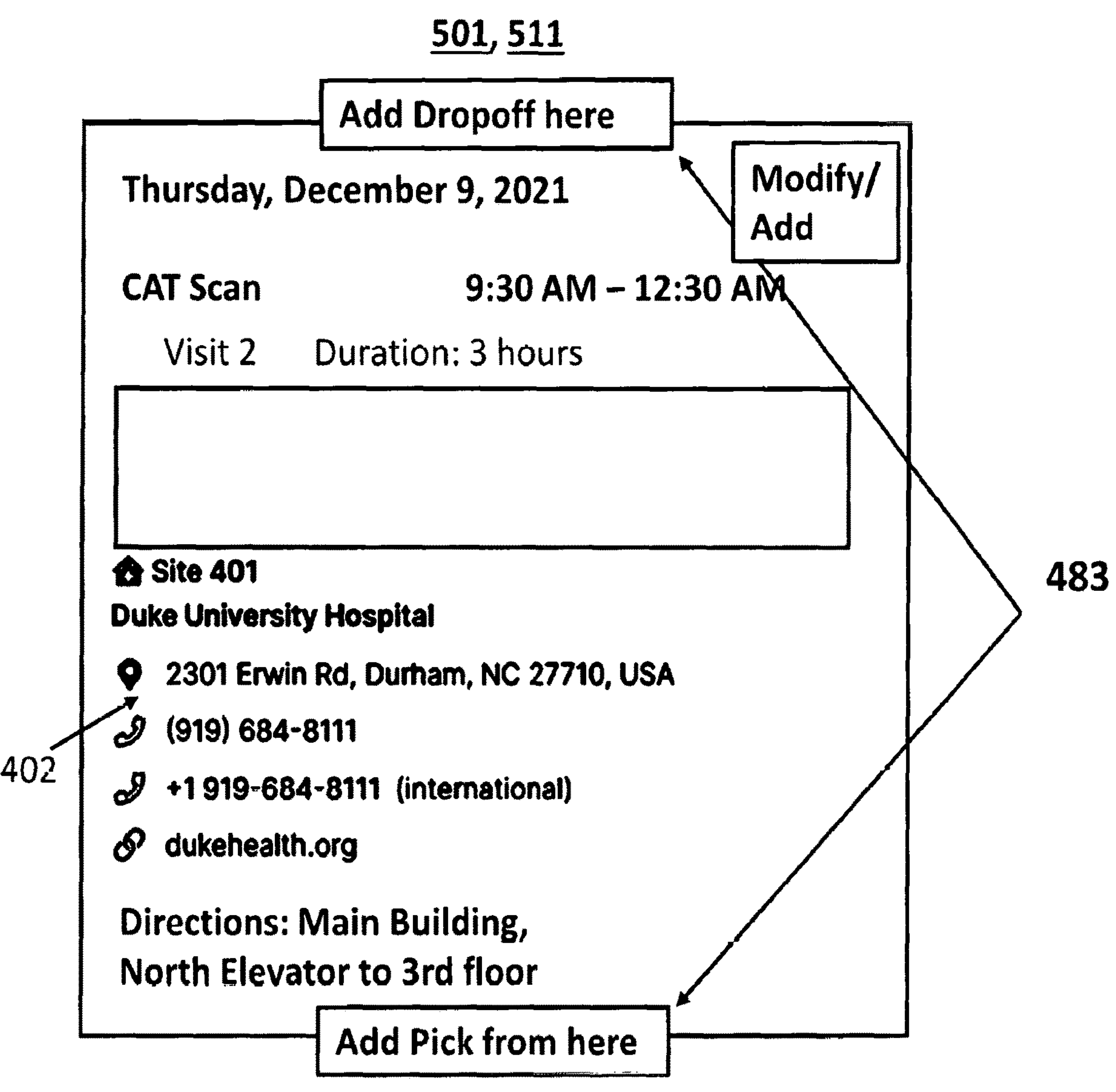
Figure 34:
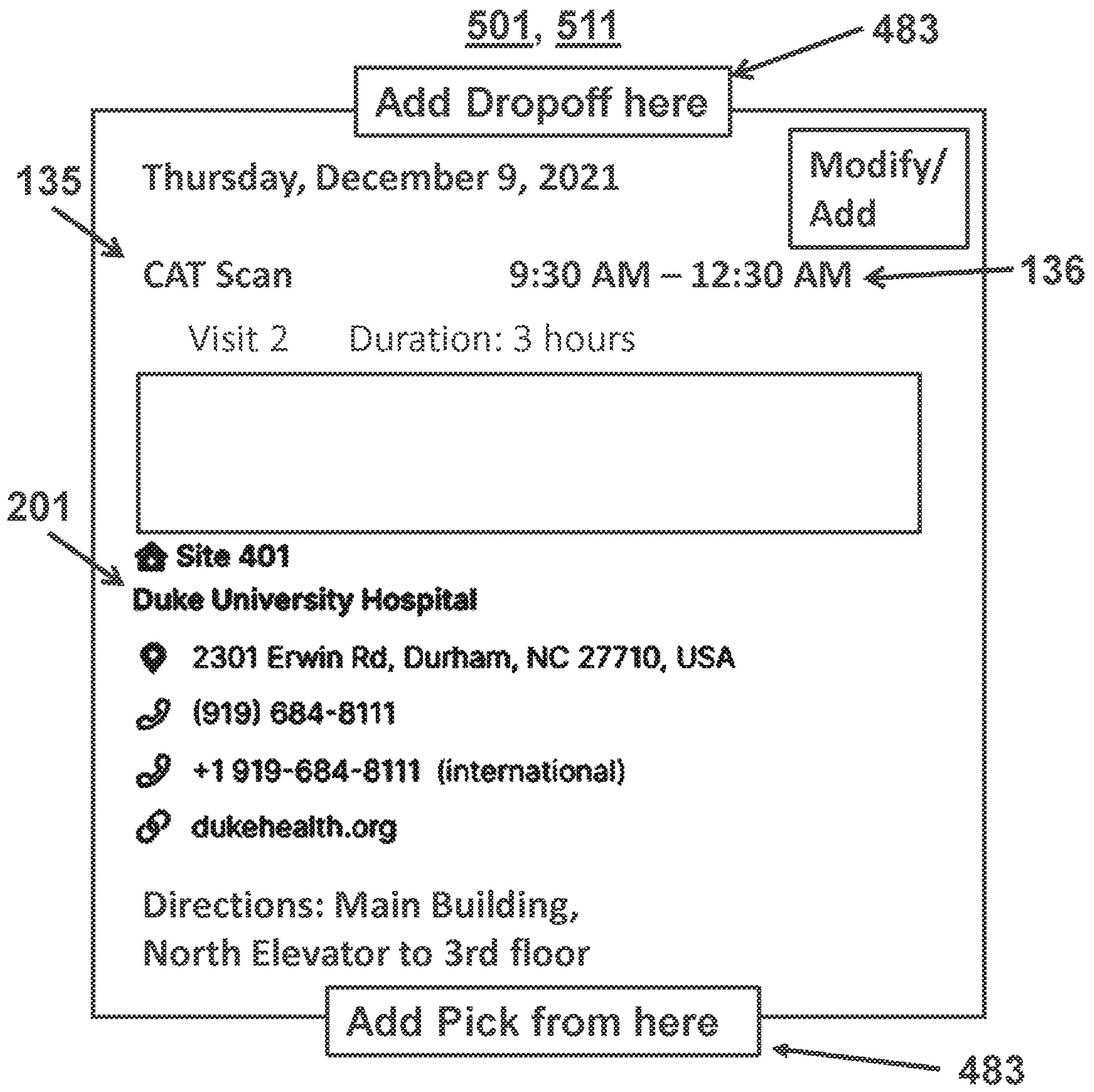
Figure 35:
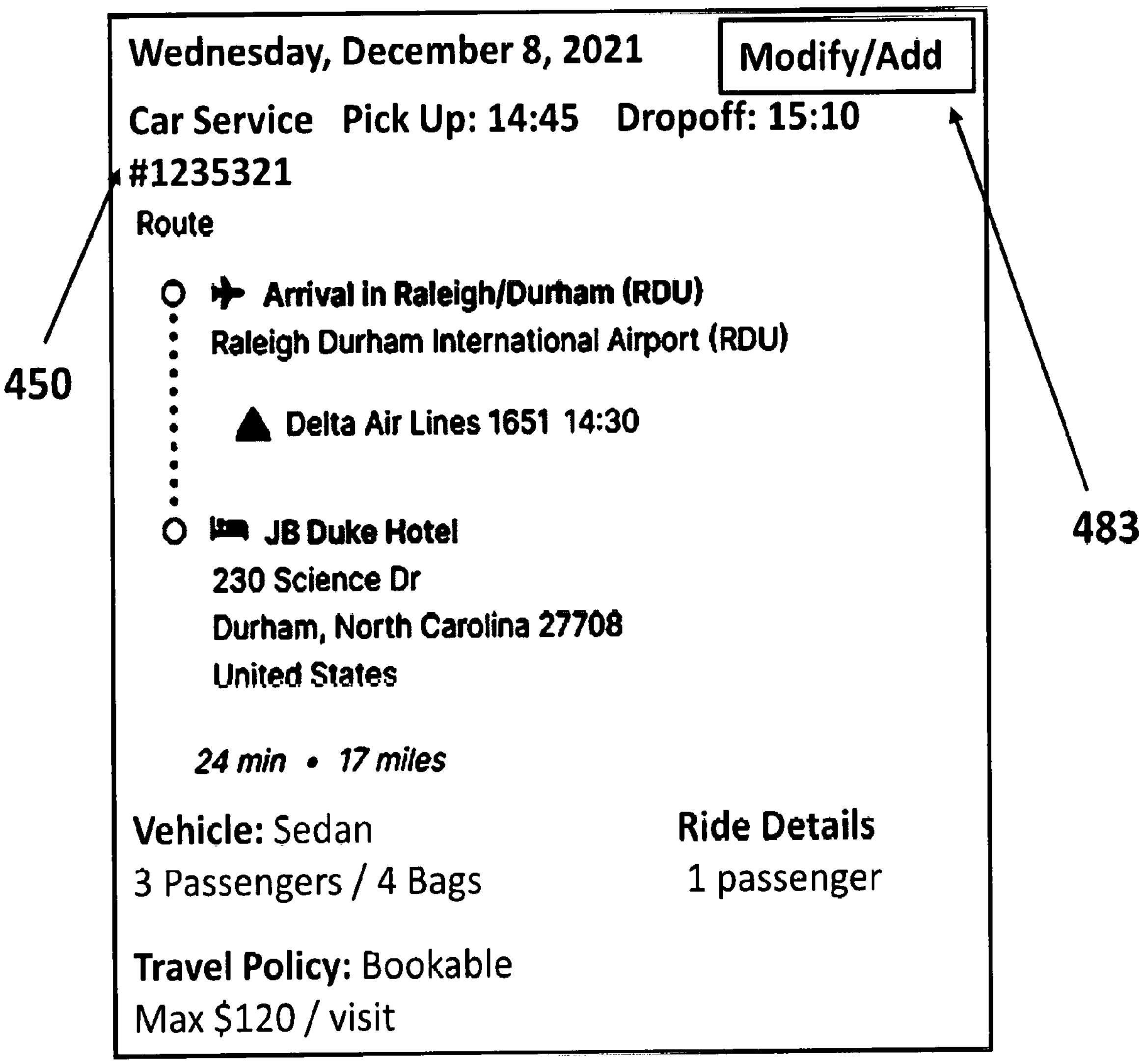
Figure 36:
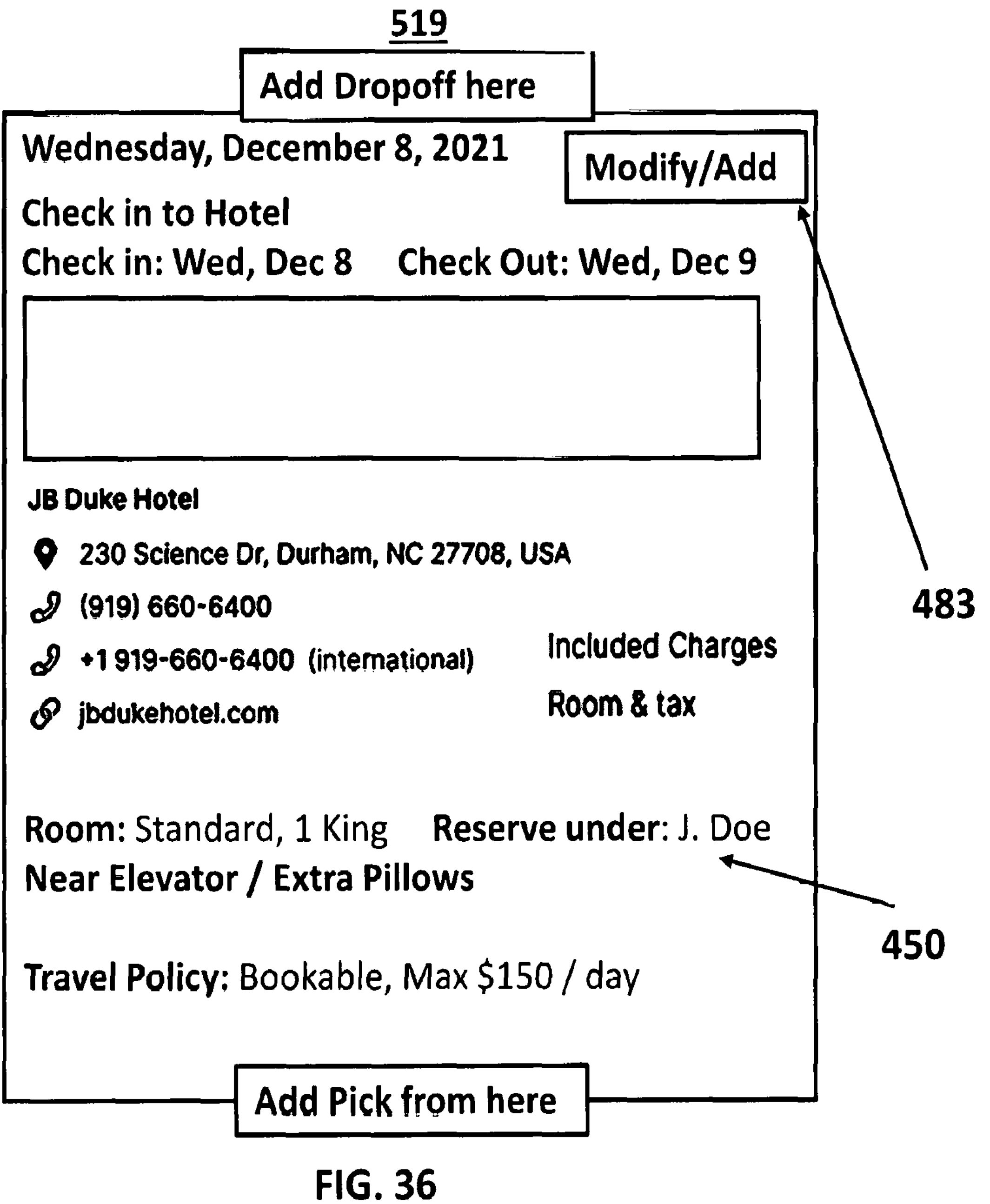

Example itinerary 475 data are illustrated in FIGS. 31 36 and may comprise Itinerary Message 478, Trip Segment Data 501, Traveler Identification 311, traveler contact information 308, and other relevant data from Trip Data Set 400 and/or Participant Data Set 300.

Trip Origin 401 comprises information about the initial, or first, departure location indicated in Trip Data Set 400 for a trip booked with a system according to the present invention. Trip Origin 401 may be based on the Traveler Origin Location 314 and a trip segment Data 501 that begins the trip. For example, if a car service segment 514 is the beginning segment of a trip, the Trip Origin 401 may be a street address provided in Traveler Origin Location 314. If a traveler's trip booked using system 1 begins at an airport (e.g., because the traveler arranged their own airport transportation) Trip Origin 401 may be a preferred airport Traveler Origin Location 314. When a trip data set 400 comprises a single trip segment, for example an appointment trip segment 511, and the patient is providing own transportation, the Travel Origin 401 and Travel Destination 402 may be the same.

Trip Destination 402 comprises information about the location where a traveler is going to, and preferably is based on the Site Appointment Location 201 and other requirements or direction that a clinical site may provide about how a participant may arrive at the Site Appointment Location 201 (e.g., arrive at a different building, at a triage station, or wait for pick up at a different location).

Trip Schedule 403 may comprise data about one or more of a trip departure time, a trip duration, and a trip return time. Trip Schedule 403 preferably is based on Appointment Schedule 136. For example, trip departure time of Trip Schedule 403 may be based on Appointment Schedule 136 so that when accounting for the trip schedules 403 of outbound trip segments the departure time is such that it ensures that a participant arrives at the trip destination 402 before or at the Appointment Schedule 136 appointment start date and time, or before the Arrive By Date and Time 137. In another example, trip return time of Trip Schedule 403 may be the departure time for a return trip, in which case it may be based on Appointment Schedule 136 so that the trip return time (e.g., time of departure for the return trip) ensures a participant does not leave Appointment Location 201 before the appointment end date and time or before the Depart After Date and Time 138, of Appointment Schedule 136. Appointment end time may be provided, or calculated based on other information, in Appointment Schedule 136, for example appointment start time and appointment duration. In another example, trip return time of Trip Schedule 403 may be the time a patient returns to Travel Origin Location 314, in which case trip return time may also be based on the appointment end time of Appointment Schedule 136 so that when accounting for the return trip segment schedules, the trip return time (e.g., time of return at patients origin location) is such as to ensure that a participant does not depart Appointment Location 201 before the end time of the Appointment Schedule 136.

Trip Segment Data 501 may comprise information about Segment Start Location 503 (e.g., beginning point or location of a trip segment), Segment End Location 504 (e.g., end location of a trip segment), Segment Schedule 505, Segment status 506 (e.g., booked, booking requested, pending, etc.), Segment Instructions 507, Segment Booking Information 508, and other relevant trip segment data.

Trip Segment Data 501 may be based on data from Traveler Profile 309, Study Travel Policies 150, Clinical Site Data Set 200, and a previous or subsequent Trip Segment 501. For example, a Segment Start Location 503 may be based upon Trip Origin 314 for a trip segment 501 beginning a trip, or Segment Start Location 503 may be based upon a Trip End Location 504. Similarly, Trip End Location 504 may be based upon Traveler Origin 314, for a trip segment concluding the return leg of a trip, or Trip End Location 504 may be based upon Trip Start Location 503 of a subsequent trip segment data 501. Trip Segment Data 501 may comprise maps and directions (e.g., from Google maps), images (e.g., of buildings, hotels) and other media based upon Trip Segment Start Location 503, Trip Segment End Location 503, and data from previous or subsequent Trip Segment Data 501.

Segment Schedule 505 may comprise a segment start time (e.g., departure time, check-in time), segment duration, and/or a segment end time (e.g., arrival time, check out time) that may be based upon data from a Segment Schedule 505 of a preceding or subsequent Trip Segment Data 501. Segment Schedule 505 may also be based on Trip Schedule 314, for example trip departure time or trip return time, for Trip Segment 501 that begins a trip or ends a trip.

Segment Instructions 507 may comprise messages (e.g., allergies, health and medical needs, preferences) to the trip segment provider (e.g., airline, car company, hotel) based on the Traveler profile 309 including appropriate data from Traveler health restrictions 312 and Traveler Preferences 313, as well as information/directions to a traveler (e.g., participant, companion) for example provided in the Clinical Site Data Set 200.

Segment Booking Information 508 comprises information necessary to book or reserve a trip segment based upon Study Travel Policy 150, including if applicable main Travel Policy 151 and/or Specialized Travel Policy 152, based upon Traveler Profile 309, including as applicable Traveler Accessibility Data Set 313 and Traveler Preferences 313, such as a preferred airline, rail, bus, car, or hotel company; ambulance provider, number of connections; allowed or preferred class of service, room type, duration of stay, car size; maximum bookable cost; traveler accessibility requirements and/or travel preferences, and other similar information. Segment Booking Information 508 also comprises additional information based upon Booked Travel Data 450 that a traveler or companion may further need to identify a trip segment, for example flight, bus, or train numbers; car license plate; car color; ambulance provider; reserved seat number; hotel/lodging name; confirmation or reservation number, and other similar information. Segment Booking Information 508 for non-travel segments, such as an appointment segment 511, may be based on data from Clinical Site Data Set 200, including Appointment Location 201, Clinical Site Contact Information 202, instructions provided by clinical site, and other similar information.

Trip Segment Data 501 may be data about an Appointment Segment 511, Flight Segment 512, Bus segment 513, Car Service Segment 514, car rental segment 515, rail segment 516, ferry segment data 517, ambulance segment 518, and Lodging Segment 519, each having one or more of a Segment Start Location 503, Segment End Location 504, Segment Schedule 505, Segment status 506, Segment Instructions 507, and Segment Booking Information 508. In an embodiment, Trip Data set 400 may comprise a first trip segment data 501, for example, an appointment segment 511, and a second trip segment data 501, for example a flight segment 512.

Appointment Segment 502, comprises data about a patient visit to a clinical site for clinical study assessment, and is based upon data from Study Visit Schedule 130, including for example Appointment Schedule 136 and Appointment Procedure 135, and may also be based on data from Clinical Site Data Set 200, including an Appointment Location 201 associated with Appointment Procedure 135.

Flight Segment Data 512 may comprise one-way flight segment data 512 having data about one or more outbound connecting flights, or a round trip flight segment data 512 having an outbound flight **512*a* (or connecting flights) and a return flight 512*b* (or connecting flights). Segment Booking Information 508 for a Flight Segment 512 may comprise information necessary to book all flights in a segment based on data from one or more of Traveler Profile 309, including Flights Preferences 341, Study Travel Policy 150 and other data, including departure and arrival airports, desired departure and arrival dates and times, seats, cost, class of service, companions, travel documents, and others. Segment Booking Information 508 for a Flight Segment 512 may also comprise data based upon Booked Travel Data 450** for booked or reserved flights, including airports, terminals, flight numbers/carriers, airline confirmation and/or ticket numbers, baggage information, and other flight information.

Segment Start Location 503 of a Flight Segment 512 may be based upon Traveler Profile 309 for example a preferred departure airport, distance from traveler home address, or Segment End Location 504 of a previous Trip Segment 501, such as a Flight Segment 512, Rail Segment 516, or another preceding Trip Segment 501. Flight Segment 512 Segment End Location 504 may be based upon Traveler Profile 309 and Appointment Location 201, such as preferred destination airport, or distance from Appointment Location 201, or Segment End Location 504 may be based upon data from subsequent flight segment 512, bus segment 513, rail segment 516, and other subsequent Trip Segments 501. Segment Start Location 503 of a round trip Flight Segment 512 may be the same as Segment End Location 504 (e.g., preferred airport from Traveler Profile 309). In that example, Outbound End Location **504*a* of outbound flight data 512*a* may be based upon Traveler Profile 309 and Appointment Location 201, or data from a subsequent Trip Segment 501, and the Return Start Location 503***b* of return flight data 512*b* preferably will be based upon the Outbound End Location 504*a* of outbound flight data 512*a*.

Segment Schedule 505 of a Flight Segment 512 may comprise flight departure and arrival times, as well as flight duration, for all connecting outbound and/or return flights within a Flight Segment 512.

Lodging Segment 513 may be a short-term hotel or long-term lodging segment 513, and may comprise, Segment Booking Information 508 of a Lodging Segment 513 such as room type, floor, size, accessibility, preferred or booked hotel or lodging company, lodging confirmation and/or reservation numbers, and other room information based on data from one or more of Traveler Profile 309, including Hotel Preferences 347 or Long-Term Housing Preferences 348, Study Travel Policy 150 and other data, and also based on data from Booked Travel Data 450 for booked or reserved lodgings. Segment Start Location 503 normally is the same as Segment End Location 504 of a Lodging Segment 513 identifying a lodging address, and may be based upon Traveler Profile 309 for example a preferred hotel or lodging company, distance from Appointment Location 201 or from a Segment End Location 504 of an arriving Flight Segment 512, Rail Segment 516, bus segment 513, or another preceding Trip Segment 501. Segment Schedule 505 of a Lodging Segment 513 may comprise room check-in and check-out times, as well as room occupancy duration and may be based on Appointment Schedule 136, Traveler Profile 309, Travel Policy 150 including any applicable Specialized Travel Policy 152 associated with a Visit Policy Label 131 and/or Traveler Policy Label 321.

Surface transportation Trip Segments 501 such as Rail Segment 343, Bus Segment 342, and Ferry Segment 344, may comprise data about a one-way or round trip surface transportation, including, Segment Booking Information 508 of a Surface Transportation Trip Segment 501 such as train, bus, ferry, or route numbers, preferred or booked railroad, bus or ferry company, confirmation and/or ticket numbers, baggage information, and other train, bus, or ferry information based on data from one or more of Traveler Profile 309, including Rail Preferences 343, bus Preferences 342, or ferry Preferences 344, Study Travel Policy 150 and other data, and also based on data from Booked Travel Data 450 for booked or reserved train, bus, or ferry trips. Segment Start Location 503 of a Surface Transportation Trip Segment 501 may be based upon Traveler Profile 309 for example a preferred departure station or port, distance from traveler home address, or Segment End Location 504 of a previous Trip Segment 501. Surface Transportation Trip Segment 501 Segment End Location 504 may indicate train station, bus stop, or ferry stop where to disembark, and may be based upon Traveler Profile 309 and Appointment Location 201, such as preferred destination station or port, or distance from Appointment Location 201, or Segment End Location 504 may be based upon data from a subsequent Trip Segment 501. Segment Start Location 503 of a Surface Transportation Trip Segment 501 that is a return train, bus, or ferry trip preferably may be based upon, or the same as, the Segment End Location 504 of the outbound Surface Transportation Trip Segment 501. Segment Schedule 505 of a Surface Transportation Trip Segment 501 may comprise train, bus, or ferry departure and arrival times, as well as trip duration, for all connecting outbound and/or return train, bus, or ferry routes within a Surface Transportation Trip Segment 501.

Car Service Segment 514 may comprise, Segment Booking Information 508 of a Car Service Segment 514 such as vehicle number and license plate, preferred or booked car company, vehicle size, confirmation numbers, luggage information, and car service information based on data from one or more of Traveler Profile 309, including Car Service Preferences 345, and other data, and also based on data from Booked Travel Data 450 for booked or reserved car service. Segment Start Location 503 of a Car Service Segment 514 may be based upon Traveler Profile 309 for example a preferred pick-up location, such as Traveler Origin Location 314, or a Segment End Location 504 of a previous Trip Segment 501. Car Service Segment 514 Segment End Location 504 may indicate a drop-off location based upon a Segment Start Location 504 of a subsequent Trip Segment 501. Segment Schedule 505 of a Car Service Segment 514 may comprise pick-up and drop-off times, as well as trip duration.

Car Rental Segment 515 may comprise, Segment Booking Information 508 of a Car Rental Segment 515 such as preferred or booked Car Rental company, vehicle size, confirmation numbers, luggage information, and other Car Rental information may based on data from one or more of Traveler Profile 309, including Car Rental Preferences 346, and other data, and also based on data from Booked Travel Data 450 for a booked or reserved Car Rental segment 515. Segment Start Location 503 of a Car Rental Segment 515 may be based upon Traveler Profile 309 for example a preferred pick-up location near Traveler Origin Location 314, or at or near a Segment End Location 504 of a previous Trip Segment 501. Car Rental Segment 515 Segment End Location 504 may be a drop off location based upon a Segment Start Location 504 of a subsequent Trip Segment 501, or Traveler Origin Location 314 for car rental segments concluding a trip. Segment Schedule 505 of a Car Rental Segment 515 may comprise pick-up and drop off times, as well as trip distance and/or duration.

Travel Planning Interface 500 of GUI 43 provides an easy and efficient process for a travel coordinator (e.g., user, concierge-user) to plan and book a trip for a traveler. A user may load and switch to Travel Planning Interface 500 utilizing user controls as described above.

Travel Booking Module 575, illustrated in FIG. 1, may be any type of system, software, device, entity, or combination thereof, that is able, or is configured, receive Booking Request Data 451 about a planned trip or trip segments, based on Booking Request Data 451 book or reserve a trip or individual trip segments, and provide booking information about the trip or segment booking or reservation. A Travel Booking Module 575 may be configured to receive from Travel Planning Interface 500 Booking Request Data 451 about a trip segment comprising one or more of Trip Segment Data 501 and Traveler Identification 311, use the received Booking Request Data 451 to book or reserve an appropriate trip segment (e.g., a flight departing from the appropriate airport on the correct date), and transmit to Travel Planning Interface 500 Booked Travel Data 450 about the booked or reserved trip segment. Booked travel data 450 for a trip segment may become part of the Trip Segment Data 501 for that segment, or Booked Travel Data 450 and Trip Segment Data 501 may be distinct. For booking or reserving transportation or lodging trip segments, Travel Booking Module 575 may comprise a browser interface that may be separate or distinct from GUI 43 and/or Travel Planning Interface 500, may be networked with GUI 43, or may be incorporated (e.g., as a separate panel, interface, frame) within GUI 43 or within Travel Planning Interface 500. Such browser interface may be configured to enable a user to access travel booking websites, and search for, select, and book or reserve, appropriate trip segments (e.g., flights, train, bus, hotel, car rental, car service) based on Trip Segment Data 501 received at Travel Booking Module 575. Travel booking websites may include websites of travel providers, such as airlines, railroads, bus companies, hotels, car rental companies, car service companies, ambulance operators, and others, or may include travel booking websites (e.g., booking.com, orbitz.com, travelocity.com, expedia.com, hotels.com, carrentals.com) that enable a user to search for trip segments from multiple providers, and/or book multiple travel segments (e.g., flight, hotel, car rental, ferry, and others).

Booking request data 451 about a trip segment to be booked may be transmitted by Travel Planning Interface 500 and received by travel booking websites utilizing software programs and network transmission instructions and protocols (e.g., APIs, URLs including trip segment information transmitted over HTTPs). Travel booking websites may also receive Booking request data 451 from input device 41, or similar input device. Booked Travel Data 450 may be transmitted by travel booking websites and received by Travel Planning Interface 500 using various tools and methods, including software programs, network transmission instructions and protocols, email, input device 41, and combinations of the foregoing.

Travel Booking Module 575 may also comprise, or include the services of, virtual or conventional booking agents (e.g., travel agents, car booking agents, train and bus agents, hotel/lodging booking agent, and travel service providers) including general travel agencies, agencies specializing in a particular type of transport (e.g., car service, long-term housing, ambulances), booking agents associated with a travel provider company (e.g., airline agents, car rental agents, hotel reservation agents), and other types of booking agents. Booking agents may receive Booking request data 451, book a trip segment based on the Booking request data 451, and transmit the booked travel data 450 to Travel Planning Interface 500. Booking request data 451 may be transmitted by Travel Planning Interface 500 and received by Booking agents through an email booking request, electronic data transfer using secure network protocols, API Interface, a phone call, and other methods. Booking agents may transmit Booked Travel Data 450 to Travel Planning Interface 500 using similar methods, including email, secure electronic data transfer, API Interface, phone call, and other methods. Instead of Booked Travel Data 450, Booking agents may also transmit to Travel Planning Interface 500 booking options and quotes data, comprising information about different trip segment options, including cost, Segment Schedule 505, transportation or lodging provider, and other options.

Travel Booking Module 575 may also comprise an interface to a clinical site, and a clinical site personnel or scheduling system when a trip segment is an appointment segment Travel Booking Module 575 may transmit booked travel data 450 the clinical site.

Travel Planning Interface 500 may also transmit booking request data 451 to Travel Booking Module 575 by storing booking request data 451 in database 2, and causing Database 2 to utilize a network interface (e.g., API, secure data transfer protocol) to transmit from booking request data 451 to Travel Booking Module 575. Travel Planning Interface 500 may also receive booked travel data 450 from Travel Booking Module 575 through database 2 (e.g., by receiving from database 2). Database 2 may store booked travel data 450 upon receiving it from Travel Booking Module 575 over a network interface (e.g., API, secure data transfer protocol).

Figure 4:
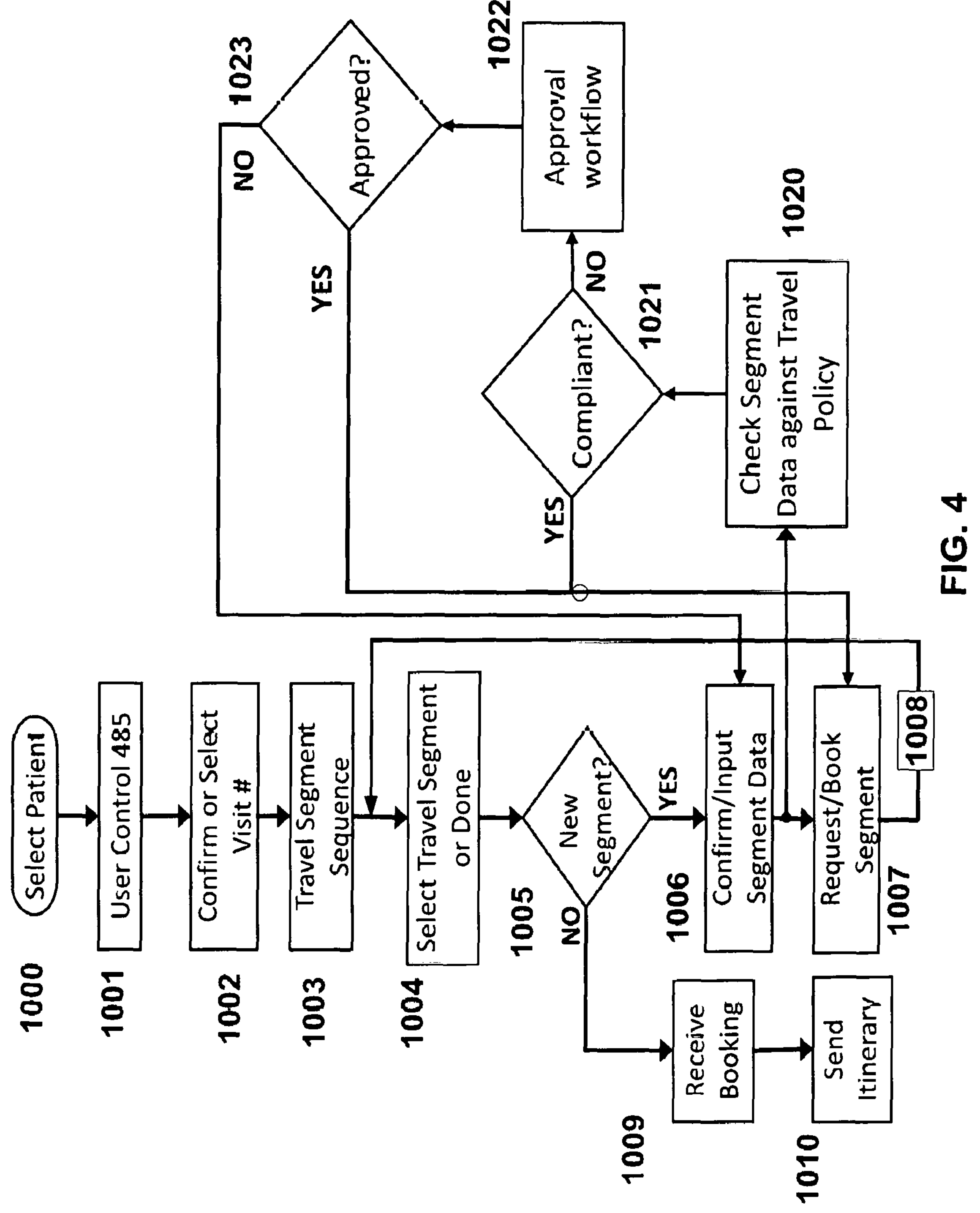
FIG. 4 is a diagram illustrating a flowchart of an embodiment of the present invention.

An embodiment of the invention may be utilized and function as illustrated in the flowchart in FIG. 4. In step 1000 a user selects a Participant 26 utilizing one or more of the Main Search Control, Travelers Panel Search Control, or Study Participants Panel, and utilizes user control 485, as indicated in step 1001, to initiate Trip Planning Interface 500, and receive Patient Visit Data 304 from the Database. In step 1002. Patient Visit Data 304 are received from Database 2 and displayed for the user to confirm and/or select a Current Visit Number 306. Upon confirming a Current Visit Number 304 the Travel Interface 500 advances to step 1003 and the GUI switches to the Trip Segments Panel providing user controls (e.g., 482 link, button, drop down list) allowing a user to add a segment. In step 1004 the user may add a trip segment by loading Trip Segment Data 501, or finish planning the trip.

In step 1005 if a new segment has been added, indicated with "Yes", the Travel Planning Interface 500 advances to step 1006 displaying the appropriate Trip Segment Panel with appropriate Trip Segment Data received from Database 2. Trip Segment Panel provides user controls (e.g., buttons, links, radio checkboxes, and others) that may be utilized to modify, select, input, and confirm Trip Segment Data 501. In step 1007, the Travel Planning Interface 500 enables a user to "request booking" by transmitting to a Travel Booking Module 575 booking request data 451 about a trip segment to be booked.

After transmitting booking request data 451 to Travel Booking System 575 the travel planning Interface 500 returns to step 1004, as indicated by arrow 1008, allowing the user to load another trip segment data 501 or to finish planning a trip by utilizing user control 482. If the user desires to book another Trip Segment the Travel Interface 501 repeats steps 1005 1007. If no more Trip Segments are needed, and the user selects to finish travel planning, indicated by a "NO" at step 1005, the Travel Interface 501 advances to step 1009 to receive the Booked Travel Data 450 from Travel Booking Module 575.

A check for compliance with travel policy may also be implemented, for example, as indicated by steps 1020-1023 after a user confirms Trip Segment Data in step 1006. In step 1020 a computing algorithm compares Trip Segment Data to the applicable Study Travel Policy 150 (e.g., cost, whether certain services are bookable or not, and other). In Step 1021, if Trip Segment Data complies with Travel Policy 150 (indicated as "YES") the Travel Interface 500 returns to step 1007. If the algorithm result is "NO", the Travel Planning Interface 500 invokes an approval workflow 1022 (which may involve escalation to management, or other steps). If the approval workflow 1022 results in approval in step 1023, the Travel Interface 500 advances to step 1007. If workflow 1022 results in a rejection in step 1023, Travel Interface 500 returns to step 1006 allowing the user to modify or input new Trip Segment Data.

Upon completion of booking a trip, Trip Planning Interface 500 generates an itinerary 475, and provides user controls 481 (e.g., to send the itinerary) allowing a user to transmit Itinerary 475 according to information from Traveler Contact Information 308 and Site Contact Information 202. For privacy and security reasons, user control 481 to send an itinerary 475 only allows itinerary 475 to be sent to pre-authorized recipients provided in Traveler Contact Information 308 and Site Contact Information 202.

GUI 43 may allow a user to utilize user control 482 to initiate the Travel Planning Interface 500. Travel Planning Interface 500 receives initial Trip Segment Data 501 from Database 2 and/or input device 41, and displays it in the Travel Planning Interface 500. The system also provides user controls that can be utilized to correct, enter, customize, and confirm information in Trip Segment Data 501 for each trip segment and for each participant. A coordinator may utilize the user controls to personalize trip Segment Data 501 for each participant, to add specific notes, detailed directions, personalized requests, and advice to make the patient experience as pleasant as it can be for a patient in a medical study.

While the invention has been described with reference to exemplary embodiments, it will be understood by those skilled in the art that various changes, omissions, and/or additions may be made and equivalents may be substituted for elements thereof without departing from the spirit and scope of the invention. In addition, many modifications may be made to adapt a particular situation or material to the teachings of the invention without departing from the scope thereof. Therefore, it is intended that the invention is not limited to the embodiments disclosed as the best mode contemplated for carrying out this invention, but that the invention will include all embodiments falling within the scope of the appended claims. Moreover, unless specifically stated, any use of the terms first, second, etc. do not denote any order or importance, but rather the terms first, second, etc. are used to distinguish one element from another.

We claim:

1. A privacy enabled system for managing clinical study participant travel comprising:
- a private cloud comprising:
  - a database configured to organize, store, and retrieve encrypted data about a clinical study;
  - a server in secure data communication with the database solely within the private cloud; and,
  - a network security system securing access to the private cloud;
- a remote workstation external to the private cloud; and,
- a GUI configured to receive the encrypted data from the server for visualization on the remote workstation;
- wherein the private cloud is configured to provide a secure computing environment for managing the encrypted data;
- wherein the network security system is configured to authenticate users and permit only the authenticated users to access the private cloud using a secure encrypted protocol, wherein the secure encrypted protocol utilizes end-to-end encryption, and, wherein the authenticated users comprise a coordinator;
- wherein the server and the remote workstation are configured to communicate through the network security system over a public internet using the secure protocol for all data transmissions, ensuring secure delivery of a traveler profile and de-identified patient personal data to the coordinator;
- wherein the remote workstation is configured to:
  - utilize the GUI to visualize the data received from the server over the secure encrypted protocol and transmit input data from an input device to the server over the secure encrypted protocol;
  - prevent caching of the traveler profile and the de-identified patient personal data to non-volatile storage; and,
  - use only volatile computer memory to display the traveler profile and the de-identified patient personal data;
- wherein the encrypted data comprise:
  - a plurality of participant datasets comprising the de-identified patient personal data about clinical study participants assigned to a coordinator, wherein the plurality of participant datasets comprises a traveler dataset, and, wherein the traveler dataset comprises de-identified traveler personal data about a traveler who is a study participant assigned to the coordinator;
  - the traveler profile comprising one or more of a traveler origin location, a traveler full name, traveler documentation, and traveler preferences;
  - a participant ID, wherein the participant ID is an anonymous identifier associated with the traveler and the clinical study, wherein the participant ID is utilized as a traveler ID;
  - a unique identifier, wherein the unique identifier is a randomly generated anonymous code associated with the traveler ID to enable de-identification of the traveler personal data utilizing one or more pseudonyms selected from the unique identifier, a second unique identifier, and the traveler ID;
  - a clinical site dataset associated with a current visit for the traveler, wherein the clinical site dataset comprises a site appointment location for the current visit and a site contact;
  - a visit schedule comprising the current visit, wherein the current visit comprises a current visit number, an appointment procedure, and an appointment schedule;
  - a study travel policy comprising travel policy rules;
  - a trip dataset; and,
  - a coordinator id associated with the coordinator and the plurality of participant datasets;
- wherein the database is further configured to:
  - enable anonymous storage and retrieval of personal data through the network security system that restricts access based on user roles, wherein the personal data comprises patient personal data and the traveler personal data;
  - employ an encryption key management service (KMS) to secure encryption keys separately from the encrypted data to prevent exposure of the personal data;
  - protect the traveler personal data by associating data records with the unique identifier;
  - utilize a lookup table to associate the unique identifier with the data records of the traveler personal data;
  - generate the unique identifier and associate it with the traveler ID;
  - store the unique identifier in a lookup table associated with the traveler ID to facilitate de-identified access to the traveler personal data;
  - restrict access to the traveler ID so that it can be retrieved only by utilizing the unique identifier;
  - use the unique identifier and the traveler ID for retrieval of the traveler personal data from the traveler profile in the encrypted data to avoid referencing actual record values of the traveler personal data and maintain privacy through de-identification;
  - restrict access to the traveler profile such that it can only be retrieved by utilizing the traveler ID accessed using the unique identifier, with access permissions restricted to the coordinator authenticated by the network security system;
  - associate the traveler dataset with the unique identifier, with encryption applied and by the coordinator authenticated by the network security system; and,
  - associate the current visit with the traveler ID, wherein the current visit is retrievable using the traveler ID accessed using the unique identifier, with access permissions restricted to the coordinator authenticated by the network security system;

wherein the network security system is further configured to:

receive login credentials from a user using the input device at the remote workstation;

authenticate the user as the coordinator by validating the login credentials against user data in the encrypted data; and, restrict the coordinator to only access the participant datasets associated with the coordinator;

wherein the Encryption Key Management Service (KMS) is configured to:

implement encryption keys; and, store the encryption keys on separately from the encrypted data they are used to encrypt;

wherein the database is configured to decrypt the traveler personal data using the encryption keys only when the traveler personal data is accessed utilizing the unique identifier;

wherein the server is configured to:

securely process the encrypted data by accessing the personal data from the database solely within the private cloud using encryption and with access permissions restricted to the coordinator;

perform a compliance check to validate trip segments data against study travel policies using a computing algorithm with the travel policy rules; and, transmit the encrypted data among the database, the GUI on the remote workstation, and a travel booking module to facilitate secure management of clinical study participant travel and generation of the trip dataset and booking request data;

wherein responsive to the network security system authenticating the user as the coordinator, the server is configured to:

retrieve from the database the coordinator ID using the login credentials validated through network security system;

transmit to the GUI at the remote workstation only the plurality of participant datasets assigned to the coordinator;

restrict the GUI at the remote workstation to only access the plurality of participant datasets assigned to the coordinator based on the coordinator id; and, receive trip segment data from the GUI for storage in the database;

wherein the GUI comprises a travel planning interface configured to enable the coordinator to plan and coordinate a trip for the traveler according to the traveler profile, the visit schedule, the clinical site dataset, and the study travel policy, displaying de-identified traveler personal data accessible through the unique identifier to prevent exposure of the travel personal data;

wherein the GUI is configured to enable the coordinator to utilize the input device a to request to view the plurality of participant datasets assigned to the coordinator, restricting access to de-identified patient personal data to prevent exposure of the patient personal data;

wherein responsive to the coordinator requesting to view the plurality of participant datasets, the GUI is configured to:

transmit, to the database, a coordinator request comprising the coordinator ID over the secure protocol with end-to-end encryption;

receive from the database the plurality of participant datasets the traveler dataset, and the unique identifier, ensuring all data remains de-identified; and, display the plurality of participant datasets in association with a participant selection control linked to the unique identifier enabling the coordinator to select the traveler by utilizing the participant selection controls;

wherein responsive to the coordinator utilizing the participant selection control to select the traveler, the GUI is configured to:

transmit to the database over the secure internet protocol a traveler selection request comprising the unique identifier;

receive from the database and display on the remote workstation the current visit number from the database maintaining de-identification of all displayed information; and, enable the coordinator to confirm the current visit; by utilizing a confirmation control visually associated with the current visit number received from the database;

wherein responsive to the coordinator confirming the current visit, the GUI is configured to:

transition to the travel planning interface, wherein the travel planning interface is configured to display information from the trip dataset filtered based on the traveler profile, visit schedule, clinical site dataset, and study travel policy;

transmit to the database the unique identifier and the current visit number over the secure internet protocol; and, receive from the database the traveler profile, the appointment schedule, and the site appointment location, displaying de-identified traveler personal data to maintain privacy;

wherein responsive to receiving the coordinator request, the database is configured to:

retrieve the plurality of participant datasets associated with the coordinator ID after verifying the coordinator access level through the network security system;

retrieve the unique identifier associated with the traveler dataset in the participant datasets; and, transmit to the GUI the plurality of participant datasets and the unique identifier maintaining encryption during transmission;

wherein responsive to receiving from the GUI the traveler selection request and unique identifier, the database is configured to:

retrieve the current visit number from the current visit using the traveler ID accessed through the unique identifier: with decryption enabled by the encryption keys managed by the KMS; and, transmit the current visit number to the GUI, maintaining encryption during transmission;

wherein responsive to receiving the unique identifier and the current visit number, the database is configured to:

retrieve the traveler profile using the traveler ID accessed via the unique identifier, with decryption enabled by the encryption keys managed by the KMS;

retrieve the site contact and the site appointment location associated with the current visit by accessing the clinical site dataset using the current visit, with the site contact and the site appointment location de-identified; and, retrieve the appointment schedule from the current visit, ensuring it remains encrypted until decrypted by an authorized key;

wherein responsive to receiving a booking request and the unique identifier, the database is configured to:

retrieve the trip dataset and the traveler profile using the traveler ID accessed using the unique identifier, with decryption enabled by the encryption keys managed by the KMS; and, transmit the trip dataset and the traveler profile to the travel planning interface, maintaining encryption and accessible only to the authenticated coordinator;

wherein responsive to receiving from the database the traveler profile, the appointment schedule and the site appointment location, the travel planning interface is configured to:

set a trip origin as the traveler origin location and a trip destination as the site appointment location, displaying only de-identified data linked to the unique identifier to prevent exposure of traveler personal data;

cause the database to generate the trip dataset, wherein the trip dataset comprises the traveler ID, the trip origin, the trip destination and the trip segments data, wherein the trip segments data comprise one or more trip segments, one or more segment start locations, one or more segment end locations, and one or more segment schedules, wherein the trip segments data is automatically checked for compliance with the study travel policy through the compliance check;

cause the database to store the trip dataset after the compliance check confirms compliance with study travel policy in association with the current visit, wherein the trip dataset is encrypted and accessible by the coordinator only through the unique identifier by its association with the traveler ID;

display the one or more trip segments in a segment sequence visualizing a trip for the traveler, wherein the segment sequence comprises visual representations of the one or more trip segments ordered according to the one or more segment schedules;

display segment user controls visually associated with a first trip segment from the one or more trip segments enabling the coordinator to:

utilize the segment user controls to delete the first trip segment that is visually associated with the segment user controls;

utilize the segment user controls to modify the first trip segment that is visually associated with the segment user controls by using the input device to input modified trip segments data; and, utilize the segment user controls to add a new trip segment before or after the first trip segment that is visually associated with the segment user controls by using the input device to input new trip segment data;

wherein the travel planning interface is further configured to:

prevent the coordinator from utilizing the segment user controls to delete or modify a second trip segment that is not associated with the segment user controls;

cause the server to perform the compliance check of one or more of the modified trip segment data and the new trip segment data to reject non-compliant modified trip segment data and non-compliant new trip segment data and return the coordinator to utilizing the segment user controls to correct the non-compliant modified trip segment data or the non-compliant new trip segment data and prevent the coordinator from submitting inputting non-compliant modified trip segment data and non-compliant new trip segment data; and, enable the coordinator to request booking of the trip for the traveler;

wherein the one or more trip segments are selected from the group consisting of an appointment segment, a flight segment, an ambulance segment, a bus segment, a car rental segment, a car service segment, a train segment, a ferry segment, a lodging segment, and combinations thereof;

wherein responsive to the coordinator requesting booking of the trip, the travel planning interface is configured to:

transmit to the database a booking request comprising the unique identifier;

receive from the database the traveler profile and the trip dataset;

generate booking request data comprising the traveler full name and de-identified data from the trip dataset received from the database; and, transmit the booking request data to a travel booking module over the secure protocol with end-to-end encryption;

wherein the travel planning interface is configured to automatically receive booked travel data from the travel booking module, wherein the booked travel data comprise the traveler ID; and, wherein responsive to receiving the booked travel data, the travel planning interface is configured to:

cause the database to store the booked travel data in association with the current visit;

generate an itinerary based on information from the booked travel data, the trip dataset, the traveler profile, the current visit, the site data, and combinations thereof; and, electronically transmit the itinerary to one or more of a traveler contact and the site contact.

2. The system of claim 1 further comprising:

encryption tools comprising the KMS, wherein the encryption tools are configured to encrypt the data in the database, and decrypt the encrypted data when the coordinator requests the encrypted data from the database; and, monitoring tools configured to monitor and log access to the database by one or more of the GUI, the travel planning interface, the coordinator, and the travel booking module;

wherein the server and the monitoring tools are configured to comply with the privacy regulations by generating automated audit trails for all data access events, wherein the privacy regulations comprise one or both of HIPAA and GDPR;

wherein the network security system is further configured to use an identity and access management system (IAM) to authenticate the user as the coordinator and to restrict access to the encrypted data based on the access permissions of the coordinator;

wherein the remote workstation, the network security system, and the database are configured to prevent caching of the personal data and purge personal data that is cached when it is not needed;

wherein the server is configured to receive patient enrollment information about the clinical study participants, wherein the patient enrollment information comprises the patient personal data;

wherein responsive to receiving the patient enrollment information the server is configured to:

cause the encryption tools to encrypt the patient enrollment information; and, cause the database to store the patient enrollment information; and, wherein the database is further configured to:

generate the de-identified patient data from the patient enrollment information;

generate the plurality of patient datasets from the de-identified patient data;

associate the plurality of patient datasets with a plurality of patient IDs, wherein the plurality of patient IDs are anonymous codes associated with the clinical study;

generate a plurality of patient unique identifiers associating them with the plurality of patient IDs;

store the plurality of patient unique identifiers separately from the plurality of patient IDs to protect the patient personal data;

store the patient personal data separately from the plurality of patient datasets; and, restrict access to the patient personal data such that it can only be retrieved by utilizing the plurality of patient IDs accessed using the plurality of patient unique identifiers, with access permissions restricted to authorized users authenticated by the network security system.

3. The system of claim 2 wherein the participant data set further comprises a participant consent record associated with the unique identifier;

wherein the participant consent record is selected from the group consisting of a consent provided indication and a consent not provided indication; and, wherein responsive to receiving from the GUI the traveler selection request and unique identifier the database is further configured to:

use the unique identifier to access the participant consent record;

use the unique identifier to access traveler dataset, the traveler profile, the traveler personal information, and the current visit; and, transmit the current visit to the GUI if the participant consent record is the consent provided indication.

4. The system of claim 3 wherein the study travel policy comprises a main travel policy and a specialized travel policy;

wherein the specialized travel policy is selected from the group consisting of a country travel policy, a clinical site travel policy, a visit travel policy, a custom traveler policy, and combinations thereof; and, wherein responsive to the coordinator adding one or more trip segments, the travel planning interface is configured to generate the trip segments data for the one or more trip segments based on information from the main travel policy, the specialized travel policy, the trip origin, the trip destination, a preceding trip segment trip segments data, a subsequent trip segment trip segments data, the traveler profile, and combinations thereof.

5. The system of claim 2, wherein the encrypted data further comprise a study id associated with a participant study id;

wherein the unique identifier is associated with the study id and with the participant study id;

wherein the traveler dataset and the traveler are associated with the participant study id; and, wherein the unique identifier is associated with the traveler and with the traveler dataset through the participant study id.

6. The system of claim 1, wherein the encryption keys are hardware encryption keys;

wherein the Encryption Key Management Service (KMS) is configured to store the hardware encryption keys on a device separate from the encrypted data they are used to encrypt; and, wherein the database is configured to decrypt the traveler personal data using the hardware encryption keys only when the traveler personal data is accessed utilizing the unique identifier.

* * * * *